(12) United States Patent
Michas et al.

(10) Patent No.: US 10,907,123 B2
(45) Date of Patent: Feb. 2, 2021

(54) SUB-PASCAL UNIDIRECTIONAL FLOW VALVES

(71) Applicant: Trustees of Boston University, Boston, MA (US)

(72) Inventors: Christos Michas, Allston, MA (US); Anant Chopra, Waltham, MA (US); Alice Elizabeth White, Brookline, MA (US); Christopher S Chen, Newton, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 6 days.

(21) Appl. No.: 16/508,033

(22) Filed: Jul. 10, 2019

(65) Prior Publication Data

US 2020/0017813 A1    Jan. 16, 2020

Related U.S. Application Data

(60) Provisional application No. 62/844,471, filed on May 7, 2019, provisional application No. 62/696,077, filed on Jul. 10, 2018.

(51) Int. Cl.
*C12M 1/00* (2006.01)
*C12M 3/06* (2006.01)
(Continued)

(52) U.S. Cl.
CPC ........ *C12M 23/16* (2013.01); *A61M 5/16881* (2013.01); *C12M 33/00* (2013.01);
(Continued)

(58) Field of Classification Search
CPC ...................................................... G01N 1/00
See application file for complete search history.

(56) References Cited

U.S. PATENT DOCUMENTS 2,644,663 A    7/1953  Klingler
3,664,371 A    5/1972  Schneider
(Continued)

FOREIGN PATENT DOCUMENTS

WO    WO 2018/022838    2/2018

OTHER PUBLICATIONS

Pearre, B. et al.; "Fast Micron-Scale 3D Printing with a Resonant-Scanning Two-Photon Microscope"; Feb. 26, 2018; arXiv:1803.07135 [physics.app-ph] (23 pages).
(Continued)

*Primary Examiner* — Jyoti Nagpaul
(74) *Attorney, Agent, or Firm* — Nixon Peabody LLP

(57) ABSTRACT

A valve includes a body including an inner bore extending between a first port and a second port, a seat, and one or more restrainers and a disk that is moveable between the seat and the one or more restrainers such that a first pressure that is less than 1 pascal and applied in a first direction causes the disk to move from a first position towards a second position to permit fluid communication between the first port and the second port. A metamaterial scaffold including a structure defining a lumen, at least a portion of an outer or non-lumen surface of the structure is coated with a plurality of biological cells, and wherein the structure is composed of a metamaterial.

20 Claims, 24 Drawing Sheets

(51) Int. Cl.
A61M 5/168 (2006.01)
G09B 23/30 (2006.01)
C12M 1/26 (2006.01)
F16K 99/00 (2006.01)
C12N 5/077 (2010.01)

(52) U.S. Cl.
CPC ........ C12N 5/0657 (2013.01); F16K 99/0009 (2013.01); F16K 99/0057 (2013.01); G09B 23/306 (2013.01); F16K 2099/0088 (2013.01)

(56) References Cited

U.S. PATENT DOCUMENTS

| | | | |
|---|---|---|---|
| 3,991,914 A * | 11/1976 | Kotuby | B05B 11/3001 |
| | | | 222/321.9 |
| 5,727,594 A | 3/1998 | Choksi | |
| 6,537,567 B1 | 3/2003 | Niklason | |
| 7,137,405 B2 | 11/2006 | Barrows | |
| 7,600,533 B2 | 10/2009 | Tai | |
| 9,669,141 B2 | 6/2017 | Parker | |
| 2005/0016596 A1 | 1/2005 | Mijers | |
| 2017/0292620 A1 | 10/2017 | Dennis | |

OTHER PUBLICATIONS

Lissandrello C. et al.; "A micro-scale printable nanoclip for electrical stimulation and recording in small nerves"; J. Neural Eng. Jun. 2017; 14(3):036006 (12 pages).
Hinson, J.T. et al.; "Titin mutations in iPS cells define sarcomere insufficiency as a cause of dilated cardiomyopatly"; Science, Aug. 28, 2015; 349(6251):982-6 (12 pages).
Hinson, J.T. et al.; "Integrative Analysis of PRKAG2 Cardiomyopathy iPS and Microtissue Models Identifies AMPK as a Regulator of Metabolism, Survival, and Fibrosis"; Cell Reports, Dec. 20, 2016;17(12). 3292-304 (25 pages).
Chopra, A. et al.: "Force Generation β-Cardiac Myosin, Titin, and α-Actinin Drives Cardiac Sarcomere Assembly from Cell-Matrix Adhesions"; Developmental Cell, Jan. 8, 2018; 44(1):87-95 (26 pages).
Keung, W. et al.; "Non-cell autonomous cues for enhanced functionality of human embryonic stem cell-derived cardiomyocytes via maturation of sarcolemmal and mitochondrial KATP channels"; Scientific Reports, Sep. 28, 2016; 6:34154 (13 pages).
Tanaka et al.; "Establishment of a confluent cardiomyocyte culture in a cylindrical microchannel"; Anal. Sci.; Sep. 2011, vol. 27, pp. 957-960 (4 pages).
Tanaka et al.; "A micro-spherical heart pump powered by cultured cardiomyocytes"; Lab on a Chip; Nov. 13, 2006; 2007, 7: 207-212; DOI: 10.1039/b612082b (6 pages).
Li et al.; "Bioengineering an electro-mechanically functional miniature ventricular heart chamber from human pluripotent stem cells"; Biomaterials; May 2018; 163:116-127; DOI: 10.1016/j.biomaterials.2018.02.024 (22 pages).
Shadrin et al.; "Cardiopatch platform enables maturation and scale-up of human pluripotent stem cell-derived engineered heart tissues"; Nature Communications 2017; 8:1825; DOI: 10.1038/s41467-017-01946-x (15 pages).
Stark, K. et al.; "Dynamic Actuation of Soft 3D Microchemical Structures Using Micro-Electromechanical Systems (MEMS)"; Adv. Mater. Technol., 3:1700293, 1-6 (2018) (6 pages).
Novak, A. et al.; "Cardiomyocytes generated from CPVTD307H patients are arrhythmogenic in response to beta-adregenic stimulation"; J. Cell. Mol. Med. 16, No. 3, pp. 468-482 (2012) (15 pages).
Nunes, S. S. et al.; "Biowire: a platform for maturation of human pluripotent stem cell-derived cardiomyocytes"; Nat. Methods 10(8):781-7 (Aug. 2013) (16 pages).
Pai, V. B. et al.; "Cardiotoxicity of Chemotherapeutic Agents"; Drug Safety 22 (4) 263-302 (Apr. 2000) (40 pages).

D'Silva, A. & Sharma, S. "Exercise-Induced Cardiac Remodeling." Circ. Cardiovasc. Imaging 8:e004277 (2015) (3 pages).
Trachsel, L. D. et al.; "Exercise-induced cardiac remodeling in non-elite endurance athletes: Comparison of 2-tiered and 4-tiered classification of left ventricular hypertrophy"; PLoS One 13(2): e0193203 (2018); retrieved from https://doi.org/10.1371/journal/pone.01932033 (12 pages).
Kenchaiah, S. et al.; "Cardiac remodeling in systemic hypertension"; Med. Clin. North Am. 88, 115-130 (2004) (16 pages).
Ma, S. P.et al.; "Tissue-Engineering for the Study of Cardiac Biomechanics"; J. Biomed. Eng. vol. 138, 021010 (2016) (14 pages).
Neves, J. S. et al.; "Acute Myocardial Response to Stretch: What We (don't) Know"; Front. PhysioL vol. 6:408; DOI: 10.3389/phys.2015.00408 (2016) (11 pages).
Toischer, K. et al.; Differential Cardiac Remodeling in Preload Versus Afterload; Circulation 7:122, 993-1003 (2010) (22 pages).
Hirt, M. N. et al.; "Increased afterload induces pathological cardiac hypertrophy: a new in vitro model"; Basic Res. Cardiol.. 107:307 (2012) (16 pages).
Mccain, M. L. et al.; "Recapitulating maladaptive, multiscale remodeling of failing myocardium on a chip"; PNAS, vol. 110, No. 24, pp. 9770-9775 (Jun. 11, 2013). doi:10.1073/pnas.1304913110/-/DCSupplemental.www.pnas.org/cgi/doi/10.1073/pnas.1304913110 (6 pages).
Song, H. et al.; "Engineered Heart Tissue Model of Diabetic Myocardium"; Tissue Eng. Part A vol. 17, Nos. 14 and 14, pp. 1869-1878 (2011) (10 pages).
De Lange, W. J. et al.; "Neonatal Mouse-Derived Engineered Cardiac Tissue a Novel Model System for Studying Genetic Heart Disease"; Circ. Res. (2011). doi:10.1161/CIRCRESAHA.111. 242354 (21 pages).
Sun, N. et al.; "Patient-Specific Induced Pluripotent Stem Cells as a Model for Familial Dilated Cardiomyopathy"; Sci. Transl. Med. 4(13): 130ra47 (2012) (20 pages).
Ovchinnikova, E. et al.; "Modeling Human Cardiac Hypertrophy in Stem Cell-Derived Cardiomyocytes"; Stem Cell Reports vol. 10, pp. 794-807 (Mar. 13, 2018) (14 pages).
Li, R. A. et al.; "Bioengineering an electro-mechanically functional miniature ventricular heart chamber from human pluripotent stem cells"; Biomaterials 163:116-127 (May 2018) (22 pages).
Thavandiran, N. et al.; "Design and formulation of functional pluripotent stem cell-derived cardiac microtissues"; Proc. Natl. Acad. Sci. U. S. A. 110, E4698-E4707 (Nov. 18, 2013) (10 pages).
Komanduri, S. et al.; "Prevalence and risk factors of heart failure in the USA: NHANES 2013-2014 epidemiological follow-up study"; J. Community Hosp. Intern. Med. Perspect. vol. 7, No. 1, 15-20 (2017) (6 pages).
Luepker, R. V. Epidemiology of heart failure. Congest. Hear. Fail. Card. Transplant. Clin. PathoL Imaging MoL Profiles 93-102 (2017). doi:10.1007/978-3-319-44577-9_6 (10 pages).
Dunlay, S. M., Weston, S. A., Jacobsen, S. J. & Roger, V. L. Risk Factors for Heart Failure: A Population-Based Case-Control Study. Am. J. Med. 122, 1023-1028 (2009). (12 pages).
Nadruz, W. Myocardial remodeling in hypertension. J. Hum. Hypertens. 29, 1-6 (2015). (7 pages).
Desai, M. Y. et al. Outcomes in Degenerative Mitre! Regurgitation: Current State-of-the Art and Future Directions. Prog. Cardiovasc. Dis. 60, 370-385 (2017). (16 pages).
Barnes, J. & Dell'Italia, L. J. The multiple mechanistic faces of a pure volume overload: Implications for therapy. Am. J. Med. Sc!. 348, 337-346 (2014). (17 pages).
Hutchinson, K. R., Stewart, J. A. & Lucchesi, P. A. Extracellular matrix remodeling during the progression of volume overload-induced heart failure. J. MoL Cell. CardioL 48, 564-569 (2010). (13 pages).
Chen, H. H. MD et al.; "Pathophysiology of volume overload in acute heart failure syndromes"; Am. J. Med. 119, 11-16 (2010) (6 pages).
Paulus, W. J. & Carabello, B. A. Aortic stenosis. Lancet 373, 956-66 (2009). (11 pages).

(56) References Cited

OTHER PUBLICATIONS

Travers, J. G., Kamal, F. A., Robbins, J., Yutzey, K. E. & Blaxall, B. C. Cardiac Fibrosis: The Fibroblast Awakens. Circ. Res. 118, 1021-40 (2016). (39 pages).

Rader, F., Sachdev, E., Arsanjani, R. & Siegel, R. J. Left ventricular hypertrophy in valvular aortic stenosis: Mechanisms and clinical implications. Am. J. Med. 128, 344-352 (2015). (9 pages).

Kundu, B. K. et al. Remodeling of glucose metabolism precedes pressure overload-induced left ventricular hypertrophy: Review of a hypothesis. CardioL 130, 211-220 (2015). (15 pages).

Oh, J. G., Kho, C., Hajjar, R. J. & Ishikawa, K. Experimental models of cardiac physiology and pathology. Heart Fail. Rev. (2019). doi:10.1007/s10741-019-09769-2 (15 pages).

Grodin, J. L. & Tang, W. H. W. Treatment strategies for the prevention of heart failure. Curr. Heart Fail. Rep. 10, 331-340 (2013). (15 pages).

Salvetti, M. et al. Changes in left ventricular geometry during antihypertensive treatment. PharmacoL Res. 134, 193-199 (2018). (7 pages).

Uriel, N., Sayer, G., Annamalai, S., Kapur, N. K. & Burkhoff, D. Mechanical Unloading in Heart Failure. J. Am. Coll. CardioL 72, 569-580 (2018). (12 pages).

Doggrell, S. Rat models of hypertension, cardiac hypertrophy and failure. Cardiovasc. Res. 39, 89-105 (2002). (17 pages).

Piene, H. & Covell, J. W. A Force-Length-Time Relationship Describes the Mechanics of Canine Left Ventricular Wall Segments during Auxotonic Contractions. Circ. Res. 49, 70-79 (1967). (10 pages).

Todica, A. et al. Monitoring of Cardiac Remodeling in a Mouse Model of Pressure-Overload Left Ventricular Hypertrophy with [18F]FDG MicroPET. MoL Imaging Biol. 20, 268-274 (2018). (7 pages).

Houser, S. R. et al. Animal models of heart failure a scientific statement from the American Heart Association. Circ. Res. 111, 131-150 (2012). (20 pages).

Schiattarella, G. G. et al. Nitrosative stress drives heart failure with preserved ejection fraction. Nature (2019). doi:10.1038/s41586-019-1100-z (46 pages).

Kazmierczak, K. et al. Remodeling of the heart in hypertrophy in animal models with myosin essential light chain mutations. Front. Physiol. 5, 1-12 (2014). (12 pages).

Milani-nejad, N. & Janssen, P. M. L. Pharmacology & Therapeutics Small and large animal models in cardiac contraction research : Advantages and disadvantages. PharmacoL Ther. 141, 235-249 (2014). (42 pages).

Kusunose, K. et al. How Similar Are the Mice to Men ? Between-Species Comparison of Left Ventricular Mechanics Using Strain Imaging. PLoS One 7, (2012). (9 pages).

Stevens, J. L. & Baker, T. K. The future of drug safety testing : expanding the view and narrowing the focus. Drug Discov. Today 14, (2009). (6 pages).

Yu, J. et al. Induced Pluripotent Stem Cell Lines Derived from Human Somatic Cells. Science (80-. ). 318, 1917-1920 (2007). (5 pages).

Takahashi, K. et al. Induction of pluripotent stem cells from adult human fibroblasts by defined factors. Cell 131, 861-872 (2007). (12 pages).

Mummery, C. L. et al. Differentiation of human embryonic stem cells and induced pluripotent stem cells to cardiomyocytes: a methods overview. Circ. Res. 111, 344-58 (2012). (28 pages).

Lian, X. et al. Robust cardiomyocyte differentiation from human pluripotent stem cells via temporal modulation of canonical Wnt signaling. 109, (2012). (10 pages).

Lan, F. et al. Abnormal calcium handling properties underlie familial hypertrophic cardiomyopathy pathology in patient-specific induced pluripotent stem cells. Cell Stem Cell 12, 101-113 (2013). (22 pages).

Itzhaki, I. et al. Modelling the long QT syndrome with induced pluripotent stem cells. Nature 471, 225-230 (2011). (6 pages).

Yazawa, M. et al. Using induced pluripotent stem cells to investigate cardiac phenotypes in Timothy syndrome. Nature 471, 230-236 (2011). (11 pages).

Santos, M. & Shah, A. M. Alterations in cardiac structure and function in hypertension. Curr. Hypertens. Rep. 16, (2014). (18 pages).

Zhang, M. et al. Recessive cardiac phenotypes in induced pluripotent stem cell models of Jervell and Lange-Nielsen syndrome: Disease mechanisms and pharmacological rescue. Proc. Natl. Acad. Sci. 111, E5383-E5392 (2014). (10 pages).

Hashem, S. et al. Brief Report: Oxidative Stress Mediates Cardiomyocyte Apoptosis in a Human Model of Danon Disease and Heart Failure. Stem Cells 2833-2841 (2013). doi:10.1002/stem.1445 (17 pages).

Ma, D. et al. Generation of patient-specific induced pluripotent stem cell-derived cardiomyocytes as a cellular model of arrhythmogenic right ventricular cardiomyopathy. Eur. Heart J. 34, 1122-1133 (2013). (12 pages).

Jung, C. B. et al. Dantrolene rescues arrhythmogenic RYR2 defect in a patient-specific stem cell model of catecholaminergic polymorphic ventricular tachycardia. EMBO MoL Med. 4, 180-191 (2012). (12 pages).

Moretti, A. et al.; Patient-Specific Induced Pluripotent Stem-Cell Models for Long-QT Syndrome; N. Eng. J. Med. vol. 363, No. 15, pp. 1397-1409 (2010) (13 pages).

Brendão, K. 0., Tabel, V. A., Atsma, D. E., Mummery, C. L. & Davis, R. P. Human pluripotent stem cell models of cardiac disease: from mechanisms to therapies. Dis. Model. Mech. 10, 1039-1059 (2017). (21 pages).

Bellin, M. & Mummery, C. L. Inherited heart disease—what can we expect from the second decade of human iPS cell research? FEBS Lett. 590, 2482-2493 (2016). (12 pages).

Ma, D. et al. Modeling type 3 long QT syndrome with cardiomyocytes derived from patient-specific induced pluripotent stem cells. Int. J. Cardio!. 168, 5277-5286 (2013). (12 page).

Kim, C. et al. Studying arrhythmogenic right ventricular dysplasia with patient-specific iPSCs. Nature 494, 105-110 (2013). (19 pages).

Kolanowski, T. J., Antos, C. L. & Guan, K Making human cardiomyocytes up to date: Derivation, maturation state and perspectives. Int. J. Cardio!. 241, 379-386 (2017). (8 pages).

Ronaldson-bouchard, K. et al. Advanced maturation of human cardiac tissue grown from pluripotent stem cells. Nature (2018). doi:10.1038/s41586-018-0016-3 (30 pages).

DeLaughter, D. M. et al. Single-Cell Resolution of Temporal Gene Expression during Heart Development. Dev. Cel139, 480-490 (2016). (25 pages).

Ivanovitch, K., Esteban, I. & Torres, M. Growth and Morphogenesis during Early Heart Development in Amniotes. J. Cardiovasc. Dev. Dis. 4, 20 (2017). (12 pages).

Goenezen, S., Rennie, M. & Rugonyi, S. Biomechanics of early cardiac development. Biomech. Model echanobiology 11, 1187-1204 (2012). (30 pages).

Liang, X., Evans, S. M. & Sun, Y. Development of cardiac pacemaker. Cell MoL Life Sc!. 74, 1247-1262 (2017). (21 pages).

Pavesi, A. et al. Controlled electromechanical cell stimulation on-a-chip. ScL Rep. 5, 11800 (2015). (12 pages).

Sidorov, V. Y. et al. I-Wire Heart-on-a-Chip I : Three-dimensional cardiac tissue constructs for physiology and pharmacology. Acta Biomater. 48, 68-78 (2017). (22 pages).

Morgan, K. Y. & Black, L. D. Mimicking Isovolumic Contraction with Combined Electromechanical Stimulation Improves the Development of Engineered Cardiac Constructs. Tissue Eng. Part A 20, 1654-1667 (2014). (14 pages).

Maidhof, R. et al. Biomimetic perfusion and electrical stimulation applied in concert improved the assembly of engineered cardiac tissue. J. Tissue Eng. Regen. Med. 4, 524-531 (2012). (21 pages).

Brown, M. A. Pulsatile Perfusion Bioreactor for Cardiac Tissue Engineering. 907-920 (2008). doi:10.1021/bp.11 (14 pages).

Bursac, N. et al.; "Cardiomyocyte Cultures With Controlled Macroscopic Anisotropy A Model for Functional Electrophysiological Studies of Cardiac Muscle"; Circ. Res. 91, 45-54 (2002); retrieved from https://www.ahajournals.org/doi/10.1161/01.RES.0000047530.88338.EB on Aug. 9, 2019 (26 pages).

(56) References Cited

OTHER PUBLICATIONS

Ma, Z. et al. Three-dimensional filamentous human diseased cardiac tissue model. Biomaterials 35, 1367-1377 (2014). (20 pages).
Tanaka, Y. et al. An actuated pump on-chip powered by cultured cardiomyocytes. Lab Chip 6, 362-368 (2006). (7 pages).
Macqueen, L. A. et al. A tissue-engineered scale model of the heart ventricle. Nat. Biomed. Eng. (2018). doi:10.1038/s41551-018-0271-5 (15 pages).
Takeuchi, R. et al. In vivo vascularization of cell sheets provided better long-term tissue survival than injection of cell suspension. 700-710 (2016). doi:10.1002/term (11 pages).
Li, L. & Fourkas, J. T. Multiphoton polymerization. Mater. Today 10, 30-37 (2007). (8 pages).
Fatkullin, N. et al.; "NMR 3D Analysis Photopolymerization"; ISSN: 0065-3195, DOI 10.1007/b12766 (Springer, 2004) (301 pages).
Bauhofer, A. A. et al.; "Harnessing Photochemical Shrinkage in Direct Laser Writing for Shape Morphing of Polymer Sheets"; Adv. Mater. 1703024, 1-6 (2017). (6 pages).
Guney, M. G. & Fedder, G. K. Estimation of line dimensions in 3D direct laser writing lithography. (2016). doi:10.1088/0960-1317/26/10/105011 (11 pages).
Buckmann, T. et al. Tailored 3D mechanical metamaterials made by dip-in direct-laser-writing optical lithography. Adv. Mater. 24, 2710-2714 (2012). (5 pages).
Cheng, D. et al. Studies of 3D directed cell migration enabled by direct laser writing of curved wave topography. Biofabrication 11, 021001 (2019). (10 pages).
Deforest, C. A. & Anseth, K. S. Cytocompatible click-based hydrogels with dynamically tunable properties through orthogonal photoconjugation and photocleavage reactions. 3, 925-931 (2011). (18 pages).
Zieger, M. M., Mueller, P., Quick, A. S., Wegener, M. & Barner-kowollik, C. Cleaving Direct-Laser-Written Microstructures on Demand. 5625-5629 (2017). doi:10.1002/anie.201701593 (5 pages).
Serien, D. & Takeuchi, S. Multi-Component Microscaffold With 3D Spatially Defined Proteinaceous Environment. ACS Biomater. Sci. Eng. 3, 487-494 (2017). (8 pages).
Koroleva, A. et al. Two-photon polymerization-generated and micromolding-replicated 3D scaffolds for peripheral neural tissue engineering applications for peripheral neural tissue engineering. Biofabrication 4, (2012). (12 pages).
Fairbanks, B. D., Singh, S. P., Bowman, C. N. & Anseth, K. S. Photodegradable, Photoadaptable Hydrogels via Radical-Mediated Disulfide Fragmentation Reaction. 2444-2450 (2011). doi:10.1021/ma200202w (7 pages).
Sokolovskaya, E., Berner, L., Brase, S. & Lahann, J Synthesis and On-Demand Gelation of Multifunctional Poly (ethylene glycol)-Based Polymers. 780-786 (7 pages).
Lay, C. L., Lee, Y. H., Lee, M. R., Phang, I. Y. & Ling, X. Y. Formulating an Ideal Protein Photoresist for Fabricating Dynamic Microstructures with High Aspect Ratios and Uniform Responsiveness. ACS Appl. Mater. Interfaces 8, 8145-8153 (2016). (9 pages).
Giustina, G. Della et al. Polysaccharide hydrogels for multiscale 3D printing of pullulan scaffolds. Mater. Des. 165, 107566 (2019). (9 pages).
Ceylan, H., Yasa, I. C. & Sitti, M. 3D Chemical Patterning of Micromaterials for Encoded Functionality. Adv. Mater. 1-7 (2017). doi:10.1002/adma.201605072 (7 pages).
Deng, X., Eyster, T. W., Elkasabi, Y. & Lahann, J Bio-Orthogonal Polymer Coatings for Co-Presentation of Biomolecules. MacromoL Rapid Comminucations 33, 640-645 (2012). (6 pages).
Scheiwe, A. C., Frank, S. C., Autenrieth, T. J., Bastmeyer, M. & Wegener, M. Subcellular stretch-induced cytoskeletal response of single fi broblasts within 3D designer scaffolds. Biomaterials 44, 186-194 (2015). (9 pages).
Richter, B. et al. Guiding Cell Attachment in 3D Microscaffolds Selectively Functionalized with Two Distinct Adhesion Proteins. Adv. Mater. (2017). doi:10.1002/adma.201604342 (6 pages).
Marino, A. et al. A 3D Real-Scale, Biomimetic, and Biohybrid Model of the Blood-Brain Barrier Fabricated through Two-Photon Lithography. Small 1-9 (2018). doi:10.1002/smll.201702959 (9 pages).
Gullo, M. R., Takeuchi, S. & Paul, 0. Muscle-actuated biomimetic hydrogel-based 3D microskeleton. 2-5 (4 pages).
Worthington, K. S. et al. Two-photon polymerization for production of human iPSC-derived retinal cell grafts. Acta Biomater. 55, 385-395 (2017). (23 pages).
Spagnolo, B. et al. Three-dimensional cage-like microscaffolds for cell invasion studies. Nat. Publ. Gr. 1-10 (2015). doi:10.1038/srep10531 (10 pages).
Jayne, R. K., Stark, T. J., Reeves, J. B., Bishop, D. J. & White, A. E. Dynamic Actuation of Soft 3D Micromechanical Structures Using Micro-Electromechanical Systems (MEMS). Adv. Mater. TechnoL 3, 1-6 (2018). (6 pages).
Meza, L. R., Das, S. & Greer, J. R. Strong, Lightweight and Recoverable Three-Dimensional Ceramic Nanolattices. Science (80-.). 345, 1322-1327 (2014). (6 pages).
Maggi, A., Li, H. & Greer, J. R. Three-dimensional nano-architected scaffolds with tunable stiffness for efficient bone tissue growth. Acta Biomater. 63, 294-305 (2017). (25 pages).
Meza, L. R. et al. Resilient 3D hierarchical architected metamaterials. Proc. Natl. Acad. Sci. 112, 11502-11507 (2015). (6 pages).
Thiel, M., Kadic, M., Schittny, R. & Wegener, M. An elastomechanical unfeelability cloak made of pentamode metamaterials. 1-6 (2014). doi:10.1038/ncomms5130 (6 pages).
Au, A. K., Lai, H., Utela, B. R. & Folch, A. Microvalves and micropumps for BioMEMS. Micromachines 2, (2011). (42 pages).
Oh, K. W. & Ahn, C. H. A review of microvalves. (2006). doi:10.1088/0960-1317/16/5/R01 (28 pages).
Ou, K. & Chiao, M. A passive check valve using microspheres for low pressure and low flow rate applications. 2011 16th Int. Solid-State Sensors, Actuators Microsystems Conf. TRANSDUCERS' 11 1785-1788 (2011). doi:10.1109/TRANSDUCERS.2011.5969456 (4 pages).
International Search Report and Written Opinion of International Patent Application No. PCT/US2019/041224, dated Nov. 18, 2019 (12 pages).

\* cited by examiner

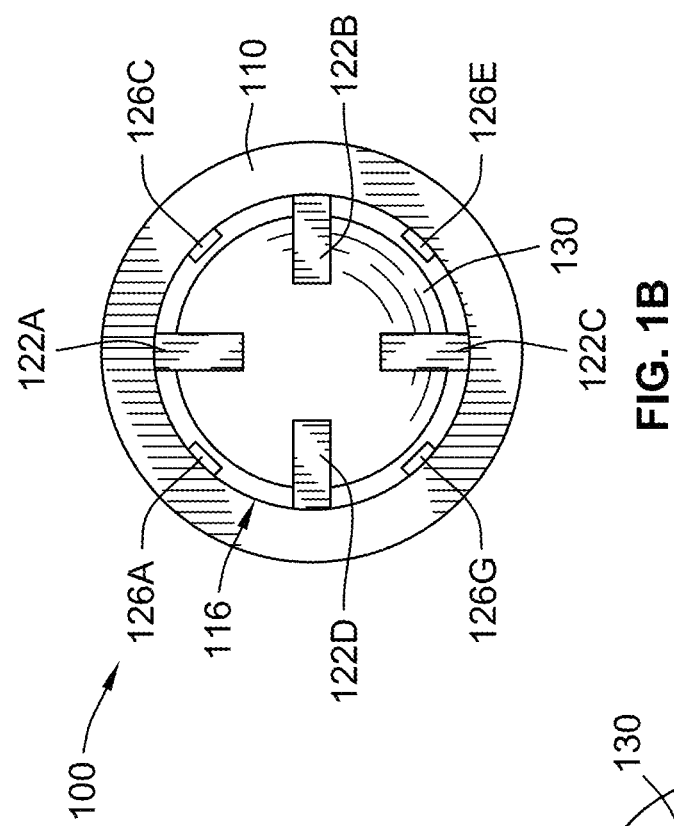
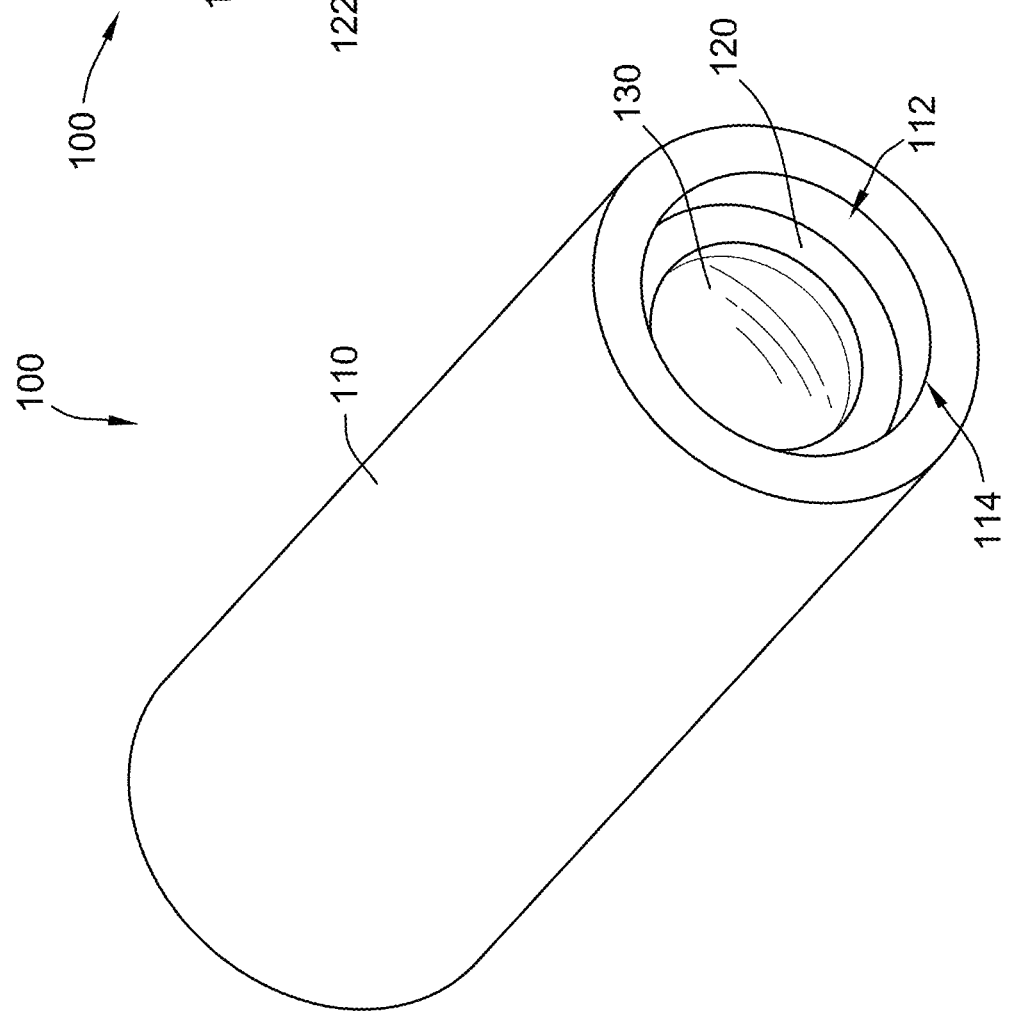

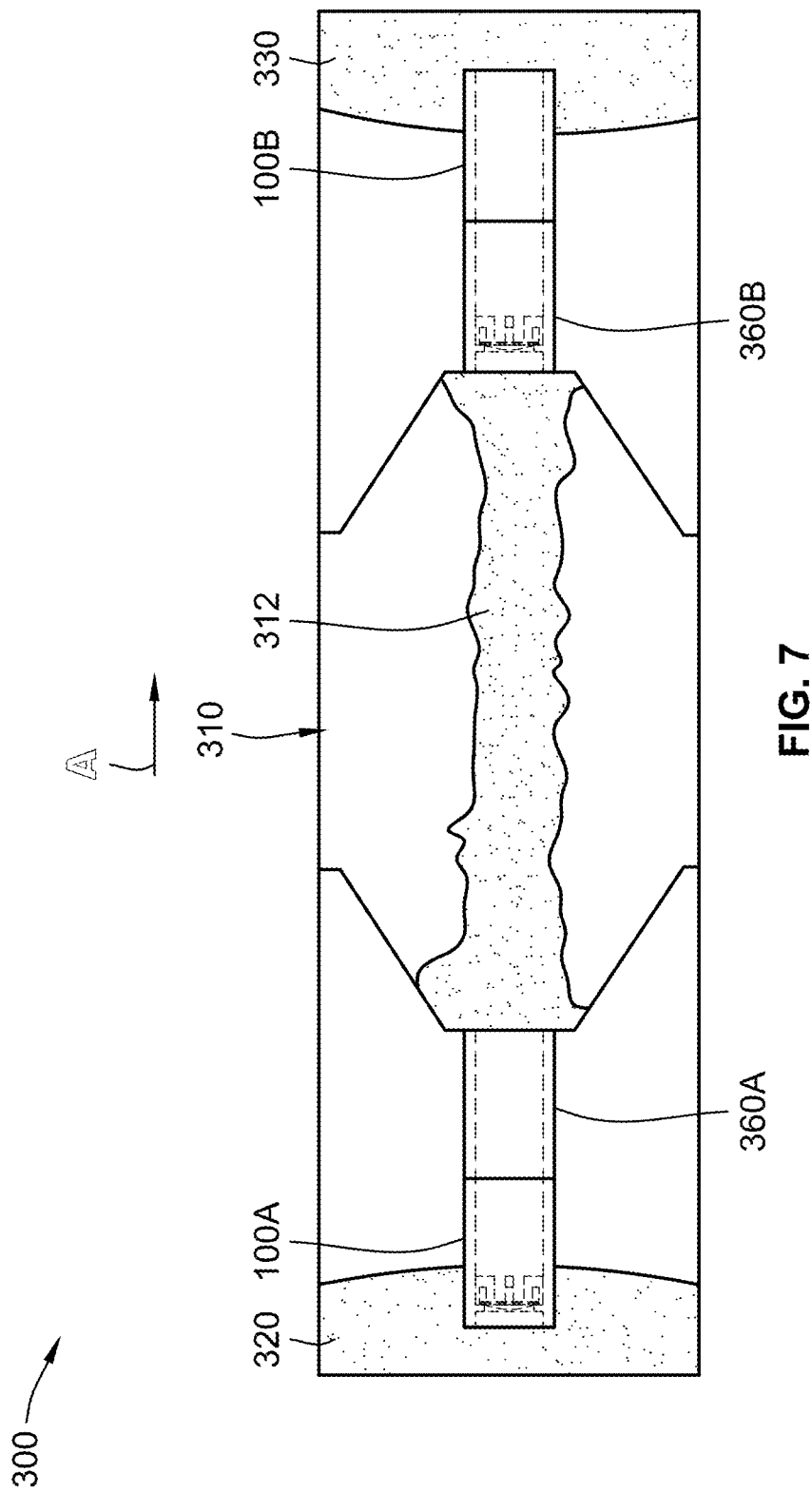

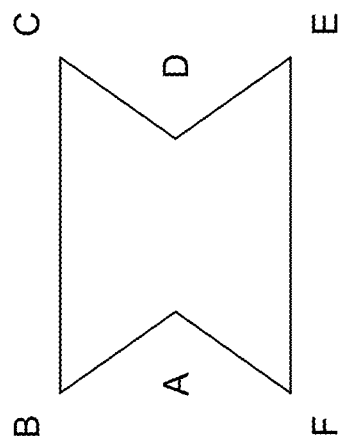
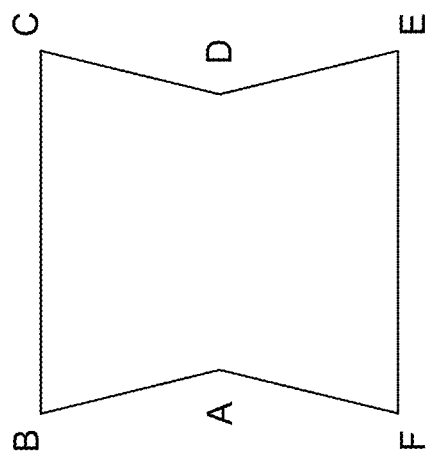
FIG. 12A
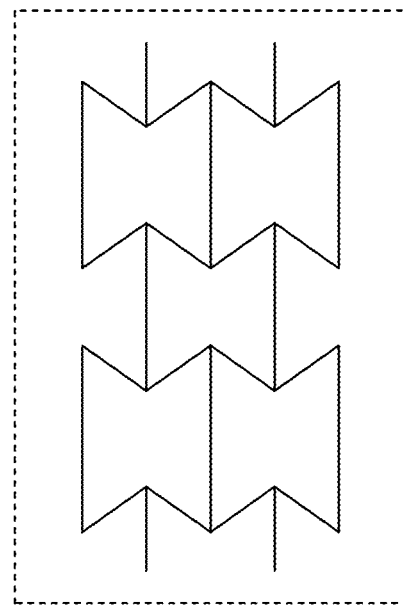
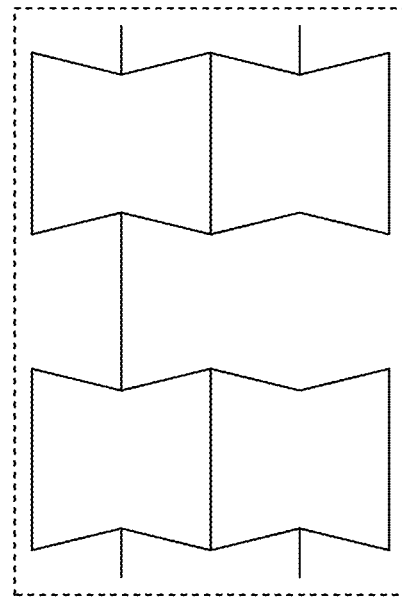
FIG. 12B

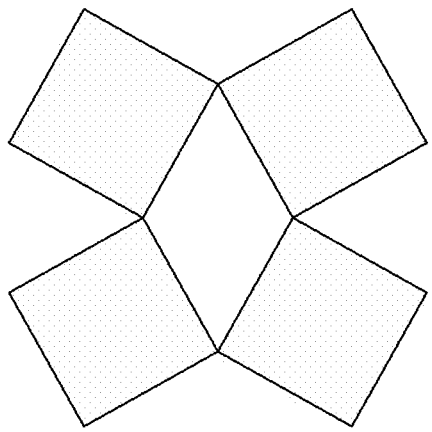
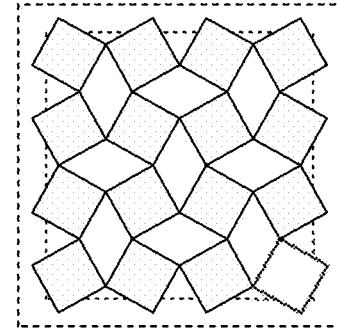
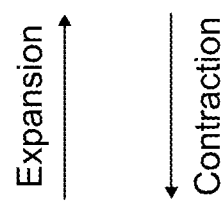
FIG. 12C
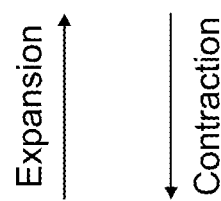
FIG. 12D
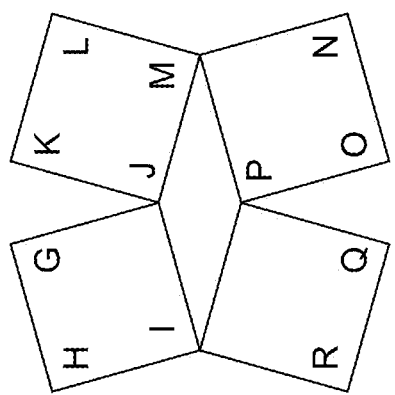
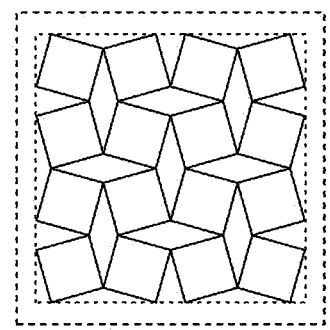

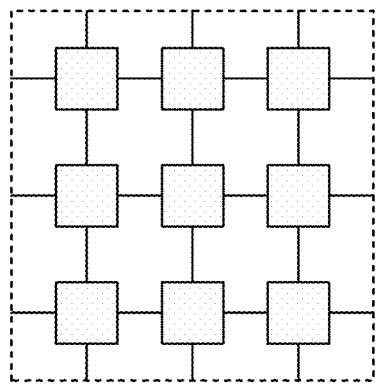
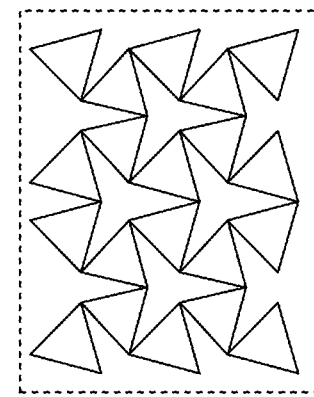
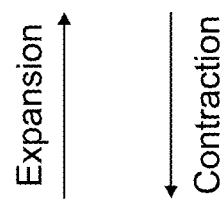
FIG. 12E
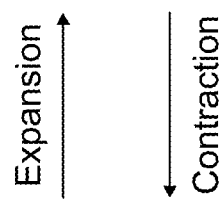
FIG. 12F
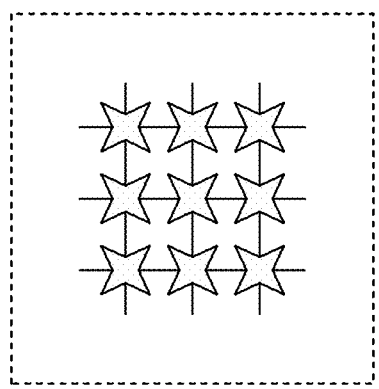
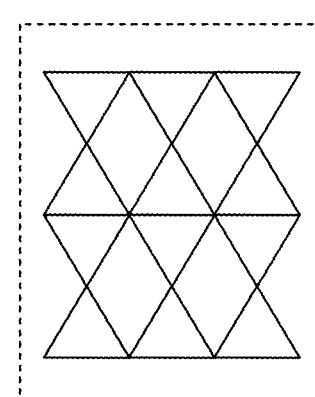

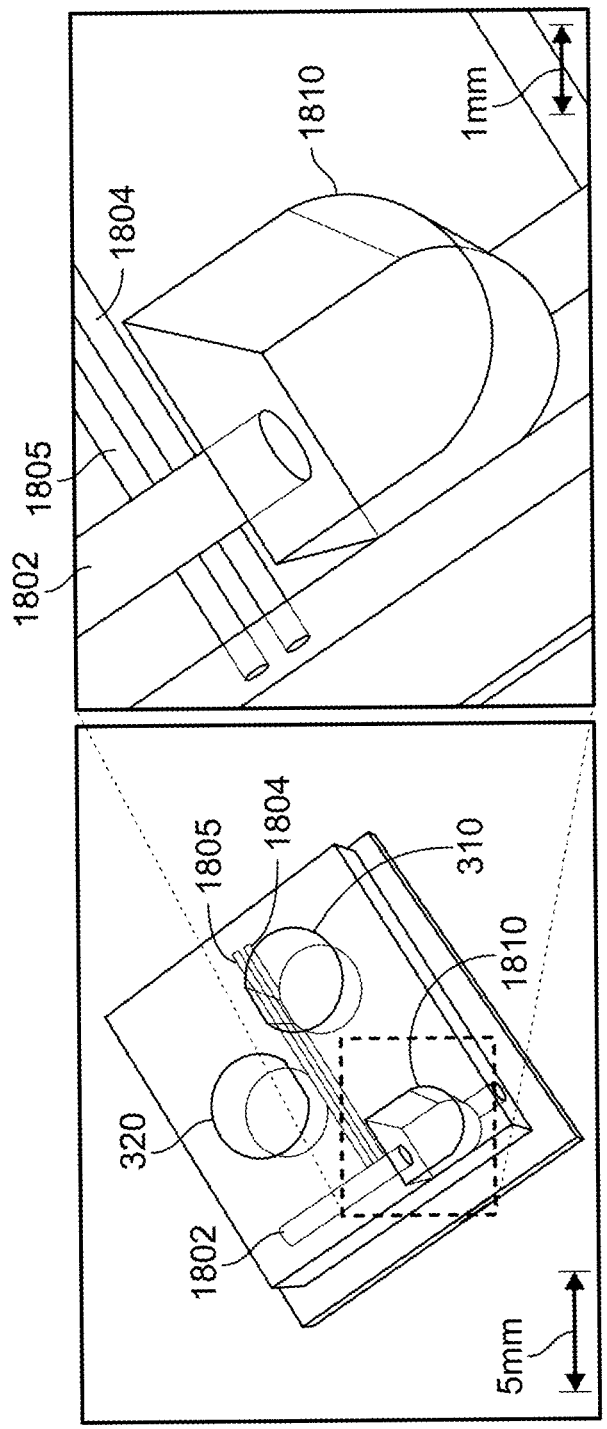

SUB-PASCAL UNIDIRECTIONAL FLOW VALVES

CROSS-REFERENCE TO RELATED APPLICATIONS

This application claims the benefit of and priority to U.S. Provisional Application No. 62/696,077, filed on Jul. 10, 2018, and U.S. Provisional Application No. 62/844,471, filed on May 7, 2019, each of which is hereby incorporated by reference herein in its entirety.

STATEMENT REGARDING FEDERALLY SPONSORED RESEARCH

This invention was made with government support under Grant No. EEC-1647837 awarded by the National Science Foundation. The government has certain rights in the invention.

TECHNICAL FIELD

The present disclosure relates generally to valves, and more particularly, to valves for use with fluidic systems or devices.

BACKGROUND

Some fluidic systems or devices operate at low pressures. These systems or devices often use a valve to control the flow (e.g., unidirectional flow) of fluid to freely permit fluid flow, completely inhibit fluid flow, or achieve a predetermined flow rate. While some valves, such as check valves, automatically open and close responsive to application of a predetermined pressure in a given direction, these valves cannot operate at low pressures because the low pressure is insufficient to cause movement of the internal plug or disk that controls flow. Thus, in fluid flow systems or devices operating at low pressures (e.g., less than 1 pascal), valve(s) typically need to be controlled manually such that the valve(s) open/close responsive to an input (e.g., a signal from a controller) rather than open/close automatically in response to application of a predetermined pressure.

The structural organization and mechanical properties of the extracellular environment can critically affect cellular properties and tissue organization. This is emphatically the case for cardiac tissue, where the highly anisotropic extracellular matrix can affect the alignment, the contractile performance and the cellular and intracellular structure of cardiomyocytes. Nevertheless, attempts to control and exploit the extracellular environment to enhance tissues in vitro fall short primarily due to the lack of techniques that can produce such environment with sufficient resolution The present disclosure is directed to solving these and other problems.

SUMMARY

According to some implementations of the present disclosure, a valve comprises a body including an inner bore extending between a first port and a second port, a seat, and one or more restrainers and a disk that is moveable between the seat and the one or more restrainers such that (i) a first pressure that is less than 1 pascal and applied in a first direction causes the disk to move from a first position towards a second position to permit fluid communication between the first port and the second port and (ii) a second pressure that is less than 1 pascal and applied in a second opposing direction causes the disk to move from the second position towards the first position to inhibit fluid communication between the first port and the second port.

According to some implementations of the present disclosure, a valve for use in a microfluidic system comprises a body including an inner bore extending between a first port and a second port, a seat having an opening and being disposed within the inner bore, and a plurality of restrainers positioned between the seat and the second port, and a disk that is moveable relative to the seat and the plurality of restrainers such that application of a first predetermined pressure that is between about 0.05 pascals and 1 pascal causes the disk to move from a first position towards a second position to permit fluid communication between the first port and the second port.

According to other implementations of the present disclosure, a metamaterial scaffold comprises (i) a structure defining a lumen; (ii) at least a portion of an outer or non-lumen surface of the structure comprises a layer of biological cells, and wherein the structure is composed of a metamaterial.

According to additional implementations of the present disclosure, a microfluidic device comprises the cylindrical metamaterial scaffold and the valve described herein.

The above summary is not intended to represent each embodiment or every aspect of the present invention. Additional features and benefits of the present invention are apparent from the detailed description and figures set forth below.

BRIEF DESCRIPTION OF THE DRAWINGS

FIG. 1A is a perspective view of a valve according to some implementations of the present disclosure;

FIG. 1B is a top view of the valve of FIG. 1A according to some implementations of the present disclosure;

FIG. 7 is a top view of a micro-cardiac device, a first valve, and a second valve according to some implementations of the present disclosure;

FIG. 12A shows a unit cell of an inverted hexagon in contraction (left) and expansion (right) according to some implementations of the present disclosure;

FIG. 12B shows an interconnected inverted hexagon lattice forming an auxetic structure in contraction (left) and expansion (right) according to some implementations of the present disclosure;

FIG. 12C shows a rotating square unit cell in contraction (left) and expansion (right) according to some implementations of the present disclosure;

FIG. 12D shows an interconnected rotating square lattice forming an auxetic structure in contraction (left) and expansion (right) according to some implementations of the present disclosure;

FIG. 12E shows a star based auxetic lattice in contraction (left) and expansion (right) according to some implementations of the present disclosure;

FIG. 12F shows a rotating triangle auxetic lattice in contraction (left) and expansion (right) according to some implementations of the present disclosure;

FIG. 18A shows an initial microfluidic device without the metamaterial scaffold according to some implementations of the present disclosure;

FIG. 18 B shows a detailed view of the microfluidic device according to some implementations of the present disclosure;

FIG. 18C shows the placement of an auxetic construct in the microfluidic device according to some implementations of the present disclosure;

FIG. 18D shows the insertion of a needle into the microfluidic device according to some implementations of the present disclosure;

FIG. 18E shows the addition of cell containing liquid to the microfluidic device according to some implementations of the present disclosure;

Figure 1C:
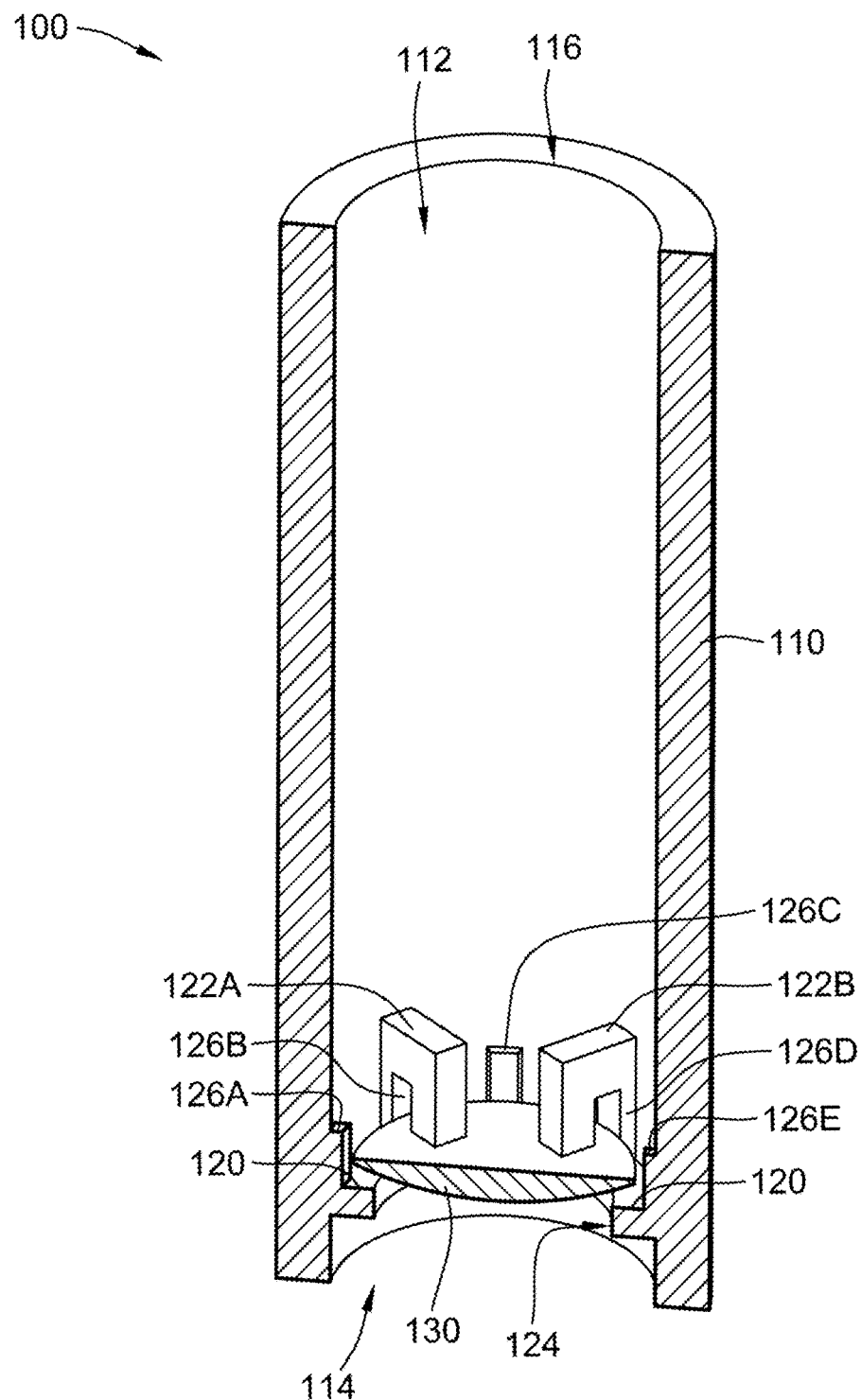
FIG. 1C is a perspective cross-sectional view of the valve of FIG. 1A according to some implementations of the present disclosure.

While the disclosure is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Many fluidic systems or devices, including micro-fluidic systems or devices (e.g., that operate at sub-millimeter scales), operate at low pressures such as, for example, pressures that are less than 1 pascal, pressures between about 0.5 pascals and about 0.05 pascals, etc. These systems and devices often use one or more valves to control the flow of fluid within the system or device. For example, the valve(s) can be used to inhibit or prevent fluid flow, freely permit fluid flow, or to precisely control the flow rate. Some valves (e.g., check valves) include an internal disk or plug that automatically opens to permit fluid flow responsive to a first predetermined pressure being applied in a first direction and automatically closes to inhibit fluid flow responsive to a second predetermined pressure being applied in a second opposing direction. However, these valves cannot operate at low pressures (e.g., less than 1 pascal) because the pressure is insufficient to cause movement of the internal plug or disk.

Referring generally to FIGS. 1A-1C, a valve 100 includes a body 110 and a disk 130. As described in further detail herein, the disk 130 is moveable relative to the body 110 responsive to application of a predetermined pressure that is, for example, less than 1 pascal. The valve 100 can generally be used, for example, in a fluidic (e.g., microfluidic) system to control fluid flow direction and rectification.

The body 110 has a generally cylindrical shape and includes an inner bore 112 extending therethrough. More specifically, as shown in FIG. 1C, the inner bore 112 extends between a first port 114 and a second port 116. As described in further detail herein, fluid can flow through the inner bore 112 between the first port 114 and the second port 116 when the disk 130 is an open position. The inner bore 112 is generally cylindrical and has an inner diameter that is less than an outer diameter of the body 110 (e.g., such that a ratio of the inner diameter to the outer diameter is ¾). While the body 110 and the inner bore 112 are both shown and described herein as being cylindrical, more generally, the body 110 and/or the inner bore 112 can have any other suitable shape or profile (e.g., a rectangular profile, a square profile, a triangular profile, or a polygonal profile).

As shown in FIG. 1C, the body 110 includes a seat 120 that is disposed within the inner bore 112. The seat 120 has an annular shape and protrudes or extends from an inner surface of the inner bore 112. The seat 120 has an opening 124 with a diameter that is less than the diameter of the inner bore 112. The opening 124 permits fluid flow between the first port 114 and the second port 116 through the seat 120. The body 110 also includes a plurality of restrainers 122A-122D that extend or protrude from the inner bore 112 and are positioned between the opening 124 of the seat 120 and the second port 116. As shown, each of the plurality of restrainers 122A-122D have a general "L" or "gamma" shape. Given their relative position in the inner bore 112, the plurality restrainers 122A-122D restrict or inhibit movement of the disk 130 such that the disk 130 is only moveable between the opening 124 of the seat 120 and the plurality of restrainers 122A-122D during operation of the valve 100. While the plurality of restrainers 122A-122D is shown as including four restrainers, the body 110 can more generally include any suitable number of restrainers (e.g., one, two, three, six, ten, etc.) and shapes to inhibit disk 130 from moving towards the second port 116 during operation of the valve 100.

In some implementations, the body 110 also includes a plurality of alignment members 126A-126H (FIGS. 1B and 1C) protruding or extending from the inner bore 112. Each of the plurality of alignment members 126A-126H are interspersed or positioned between a pair of the plurality of restrainers 122A-122D or is positioned directly underneath the plurality of the restrainers 122A-122D. For example, as shown in FIGS. 1B and 1C, a first alignment member 126A is positioned between a first restrainer 122A and a fourth restrainer 122D, a second alignment member 126B is positioned under the first restrainer 122A, a third alignment member 126C is positioned between the first restrainer 122A and a second restrainer 122B, a fourth alignment member 126D is positioned under the second restrainer 122B, a sixth alignment member 126E is positioned between the second restrainer 122B and the third restrainer 122C, a sixth alignment member 126F is positioned under the third restrainer 122C, a seventh alignment member 126G is positioned between the third restrainer 122C and the fourth restrainer 122D, and an eight alignment member 126H is positioned under the fourth restrainer 122D. The plurality of alignment members 126A-126H generally aid in positioning (e.g., centering) the disk 130 over the opening 124 of the seat 120 so that the disk 130 can inhibit flow through the inner bore 112 between the first port 114 and the second port 116 during operation of the valve 100 responsive to the disk 130 being a closed position. As shown in FIG. 1C, each of the plurality of alignment members 126A-126H have a generally rectangular shape, although other shapes and/or profiles are contemplated (e.g., triangular, circular or semi-circular, polygonal, etc.). Moreover, while the plurality of alignment members 126A-126D is shown as having four alignment members (e.g., the same as the number of the plurality of restrainers 122A-122D), the plurality of alignment members 126A-126H can more generally include any suitable number of alignment members for aligning (e.g., centering) the disk 130 during operation of the valve 100 (e.g., one, two, three, six, ten, etc.)

As shown in FIG. 1C, the disk 130 is generally positioned between the seat 120 and the plurality of restrainers 122A-122D. As described herein, the disk 130 is moveable relative to the rest of the valve 100. Because the disk 130 has a diameter that is greater than the diameter of the opening 124 of the seat 120, and because of the relative position of the plurality of restrainers 122A-122D, the disk 130 cannot move past the seat 120 and/or the plurality of restrainers 122A-122D during operation of the valve 100. That is, movement of the disk 130 is confined to a predetermined area or portion of the valve 100 defined by the seat 120 and the plurality of restrainers 122A-122D. The plurality of alignment members 126A-126H aid in aligning (e.g., centering) the disk 130 over the opening 124 of the seat 120 during operation of the valve 100.

Figure 2A:
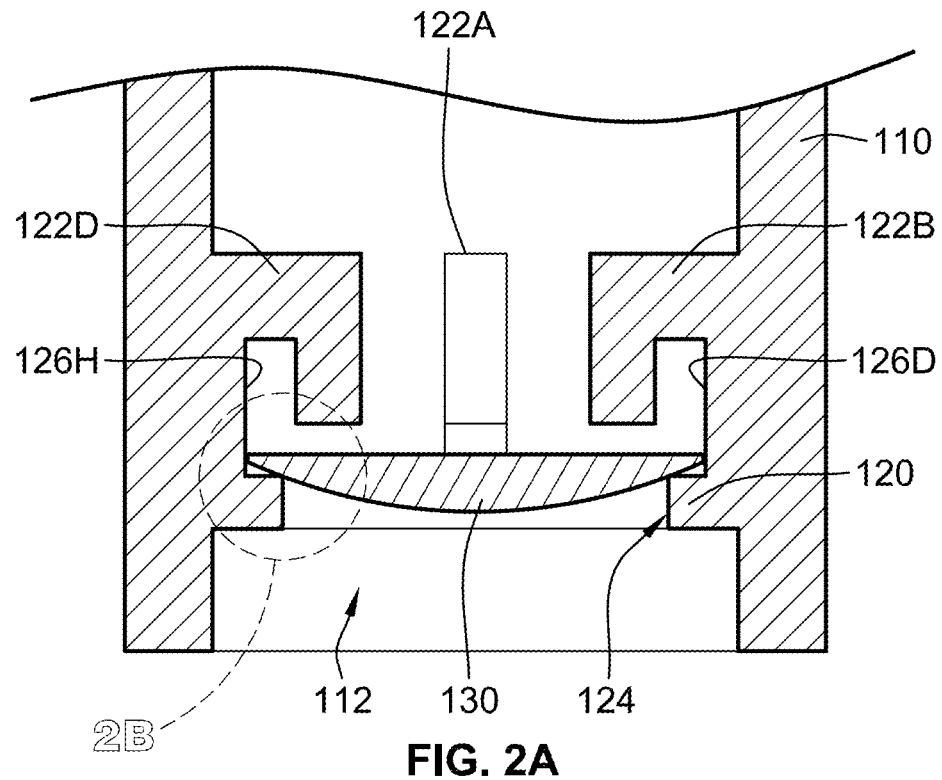
FIG. 2A is a partial cross-sectional side view of the valve of FIG. 1A with a disk in a first position according to some implementations of the present disclosure
Figure 2B:
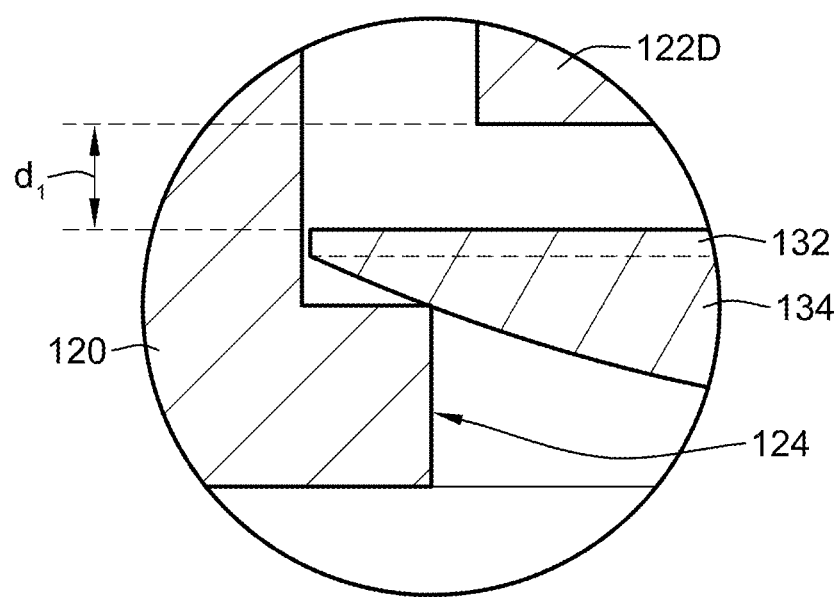
FIG. 2B is a zoomed-in view showing portions of the disk and seat of the valve of FIG. 2A according to some implementations of the present disclosure

Referring to FIGS. 2A and 2B, the disk 130 is shown in a first or closed position. As shown, in the first position, a portion of the disk 130 contacts the seat 120 (e.g., covers the opening 124 and/or extends or protrudes into the opening 124) such that fluid cannot flow from the first port 114 past the disk 130. As shown in FIG. 2B, the disk 130 includes a cylindrical portion 132 and a spherical portion 134. A portion of the spherical portion 134 is disposed within or protrudes into the opening 124 of the seat 120 to inhibit fluid from flowing past the disk 130 in either direction through the inner bore 112. The shape of the spherical portion 134 aids in maintaining sufficient contact between the seat 120 and the disk 130 to inhibit fluid flow in case of lateral displacement of the disk 130 relative to the opening 124. In the first position, an upper surface of the cylindrical portion 132 of the disk 130 is spaced from a lower surface of each of the plurality of restrainers 122A-122D (e.g., restrainer 122D as shown in FIG. 2B) by a first distance $d_1$.

Figure 2C:
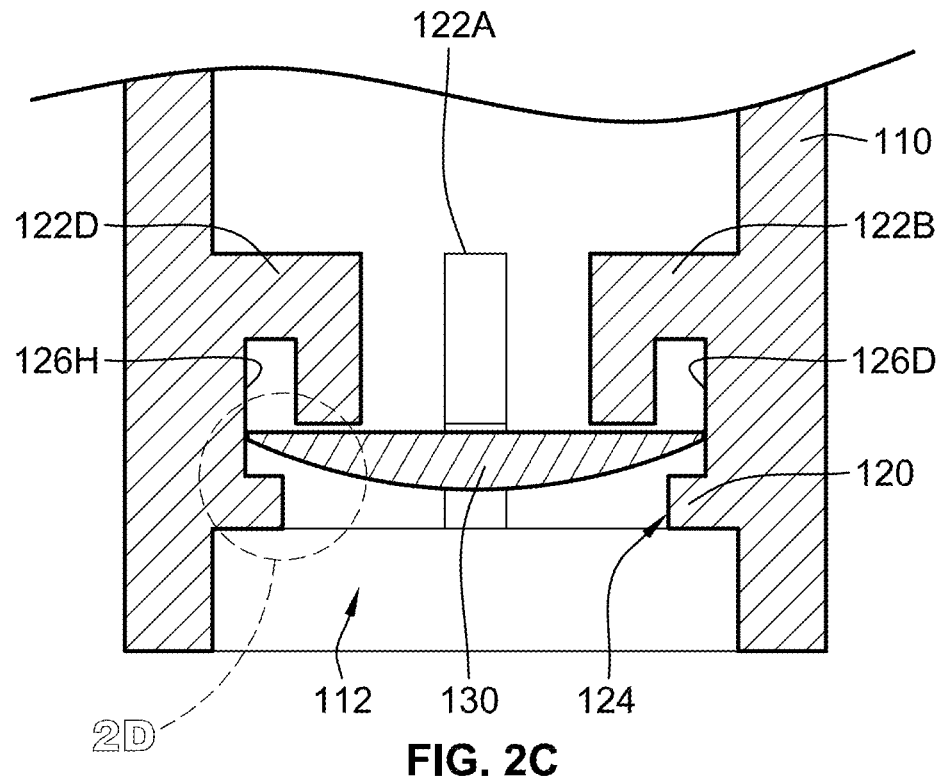
FIG. 2C is a partial cross-sectional side view of the valve of FIG. 1A with a disk in a second position according to some implementations of the present disclosure.
Figure 2D:
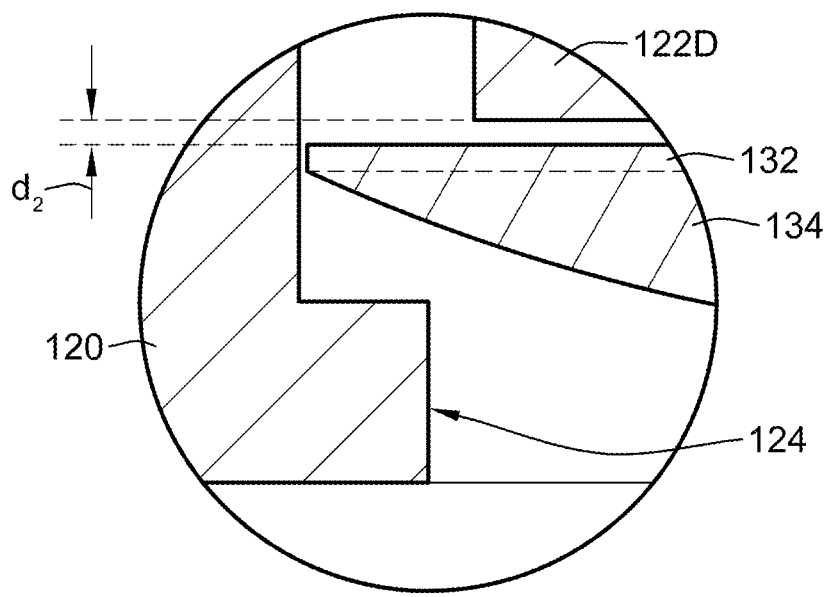
FIG. 2D is a zoomed-in view showing portions of the disk and seat of the valve of FIG. 2C according to some implementations of the present disclosure.

Referring to FIGS. 2C and 2D, the disk 130 is shown in a second or open position. As shown, in the second position, the disk 130 is spaced from the seat 120 such that fluid can flow through the opening 124 and past the disk 130 (e.g., such that fluid can flow from the first port 114 to the second port 116 through the inner bore 112. In the second position, the upper surface of the cylindrical portion 132 of the disk 130 is spaced from a lower surface of each of the plurality of restrainers 122A-122D (e.g., restrainer 122D as shown in FIG. 2B) by a second distance $d_2$ that is less than the first distance $d_1$. While the disk 130 is shown as being spaced from both the seat 120 and the plurality of restrainers 122A-122D in the second (open) position in FIGS. 2C and 2D, in some implementations, the upper surface of the disk 130 is in contact with the lower surface of the plurality of restrainers 122A-122D when the disk 130 is in the second position.

The disk 130 automatically moves during operation of the valve 100 from the first position (FIG. 2A) to the second position (FIG. 2C) in response to application of a first predetermined pressure in a first direction (e.g., from the first port 114 towards the second port 116), which causes a pressure differential between the first port 114 and the second port 116, to permit fluid to flow through the inner bore 112 between the first port 114 and the second port 116. Similarly, the disk 130 of the valve 100 automatically moves during operation of the valve 100 from the second position (FIG. 2C) to the first position (FIG. 2A) in response to application of a second predetermined pressure in a second opposing direction (e.g., from the second port 116 towards the first port 114), which causes a pressure differential between the first port 114 and the second port 116, to inhibit or prevent fluid flow through the inner bore 112 between the first port 114 and the second port 116. In some implementations, the first predetermined pressure and/or the second predetermined pressure are less than about 1 pascal. Generally, the first predetermined pressure and/or the second predetermined pressure can be between about 0.01 pascals and about 1 pascal, between about 0.05 pascals and 0.75 pascals, between about 0.05 pascals and about 0.5 pascals, etc. The absolute value of the first predetermined pressure can be the same as, or different than, the absolute value of the second predetermined pressure. For example, the absolute value of the first predetermined pressure can be greater than the absolute value of the second predetermined pressure, or vice versa.

Figure 3A:
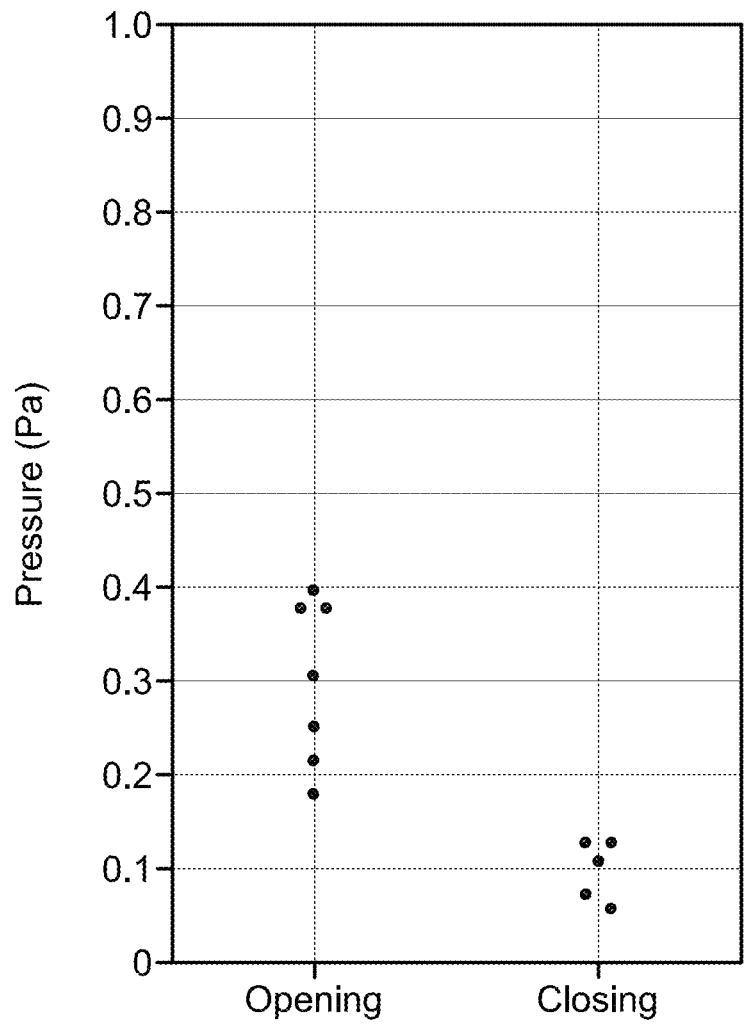
FIG. 3A is a graph showing exemplary pressure values for causing the valve of FIGS. 1A-2D to move from the first position to the second position and vice versa according to some implementations of the present disclosure.

Referring to FIG. 3A, a graph showing exemplary first/second predetermined pressure differential values for causing the disk 130 to move from the first position (FIG. 2A) to the second position (FIG. 2C) or vice versa according to one implementation of the valve 100 is shown. In the example of FIG. 3A, the first predetermined pressure (pressure differential) for causing the disk 130 to move from the first position (FIG. 2A) to the second position (FIG. 2C) (e.g., to permit fluid flow) is between about 0.4 pascals and about 0.8 pascals (e.g., about 0.4 pascals, about 0.38 pascals, about 0.31 pascals, about 0.25 pascals, about 0.22 pascals, about 0.18 pascals, etc.). As shown, the second predetermined pressure, for causing the disk 130 to move from the second position (FIG. 2C) to the first position (FIG. 2A) (e.g., to inhibit fluid flow), is less than the first predetermined pressure values and is generally between about, for example, 0.13 pascals and about 0.06 pascals (e.g., about 0.13 pascals, about 0.11 pascals, about 0.08 pascals, about 0.06 pascals, etc.)

Figure 3B:
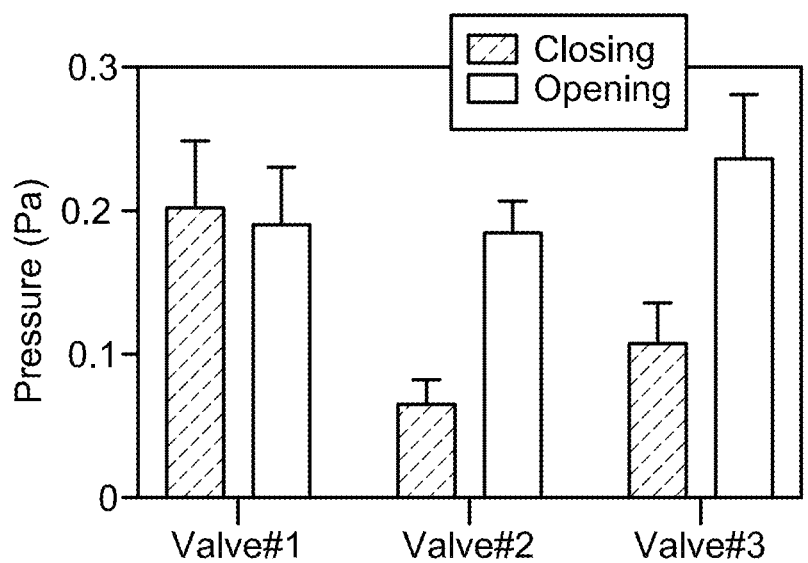
FIG. 3B is a graph showing alternative exemplary pressure values for causing the valve of FIGS. 1A-2D to move from the first position to the second position and vice versa according to some implementations of the present disclosure.

Referring to FIG. 3B, a graph showing alternative exemplary first/second predetermined pressure differential values for causing the disk 130 to move from the first position (FIG. 2A) to the second position (FIG. 2C) or vice versa according to some implementations of the valve 100 is shown. In a first implementation of the valve 100, the first predetermined pressure and the second predetermined pressure are both about 0.2 pascals. In a second implementation of the valve 100, the first predetermined pressure is about 0.2 pascals and the second predetermined pressure is about 0.08 pascals. In a third implementation of the valve 100, the first predetermined pressure is about 0.23 pascals and the second predetermined pressure is about 0.13 pascals.

Figure 4A:
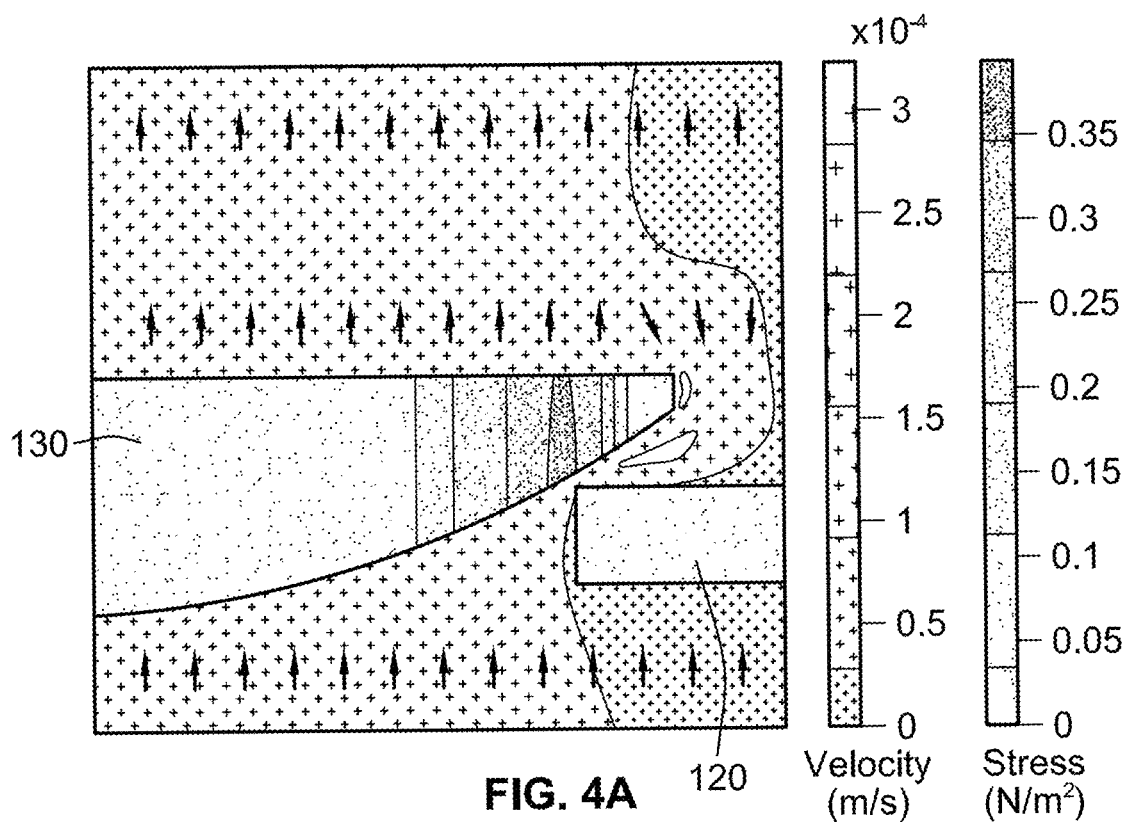
FIG. 4A illustrates exemplary simulated von Mises stress and fluid velocity values during movement from the first position (FIGS. 2A-2B) to the second position (FIGS. 2C-2D) according to some implementations of the present disclosure.
Figure 4B:
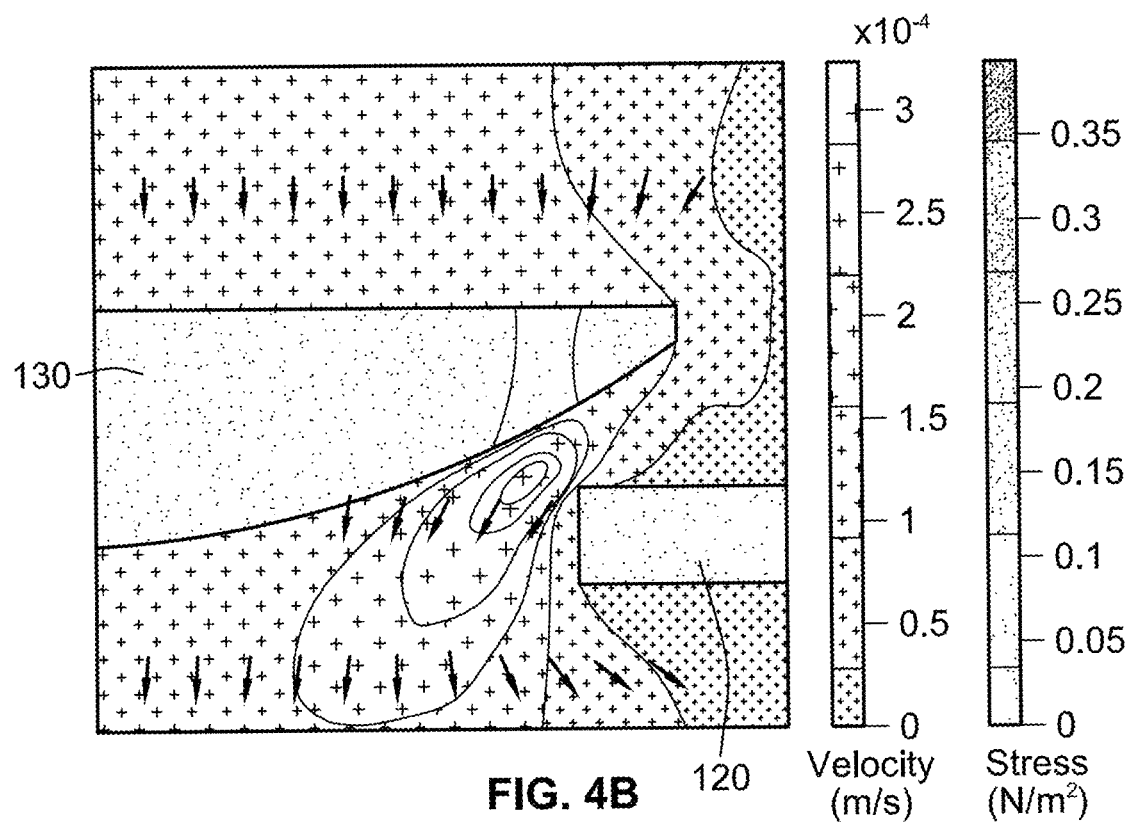
FIG. 4B illustrates exemplary simulated von Mises stress values and fluid velocity during movement from the second position (FIGS. 2C-2D) to the first position (FIGS. 2A-2B) according to some implementations of the present disclosure.

Referring to FIG. 4A, an image showing exemplary von Mises stress and fluid velocity values during movement of the disk 130 from the first position (FIGS. 2A-2B) to the second position (FIGS. 2C-2D) according to one exemplary, non-limiting implementation of the valve 100 is shown. In the example of FIG. 4A, a 0.1 pascal pressure differential is applied to open the valve 100 (move the disk 130 from the first position towards the second position) and the disk 130 automatically stops moving towards the second position after traveling a distance of about 20 microns. Referring to FIG. 4B, a graph showing exemplary von Mises stress values and fluid velocity values during movement of the disk 130 from the second position (FIGS. 2C-2D) to the first position (FIGS. 2A-2B) according to one exemplary, non-limiting implementation of the valve 100 is shown. In the example of FIG. 4B, a −0.1 pascal pressure differential (applied in the opposite direction as the 0.1 pascal pressure in FIG. 4A) causes the valve 100 to close (move the disk 130 from the second position towards the first position) with the disk 130 starting about 20 microns away from the seat 120.

The dimensions of one or more of the components of the valve 100 can be selected to adjust the properties and/or performance of the valve 100. For example, an outer diameter of the body 110 and a diameter of the inner bore 112 can be selected to provide a sufficient thickness of the body 110 for mechanical robustness. As another example, a distance between the first port 114 and a lower surface of the seat 120 (FIG. 1C) can be selected to minimize the distance between the disk 130 and the pressure source. As a further example, a thickness or height of the cylindrical portion 132 (FIG. 2B) of the disk 130 and/or a degree of curvature of the spherical portion 134 (FIG. 2B) of the disk 130 can be selected to improve contact (e.g., coaptation) between the disk 130 and the seat 120 when the disk 130 is in the first position (FIG. 2A) and/or mechanical robustness of the disk 130. A diameter of the disk 130 (that will be less than the diameter of the inner bore 112) can be selected to improve contact (e.g., coaptation) between the disk 130 and the seat 120 when the disk 130 is in the first position (FIG. 2A) and/or minimize resistance to fluid flow when the disk 130 is in the second position (FIG. 2C). A distance between the upper surface of the seat 120 and a lower surface of each of the plurality of restrainers 122A-122D can be selected to permit sufficient fluid flow when the disk 130 is in the first position (FIG. 2A) and to permit short transition times. For another example, a distance between the outer surface of opposing ones of the plurality of alignment members 126A-126D (e.g., between alignment members 126A and 126C or between alignment members 126B and 126D) can be selected to minimize spacing to improve alignment (e.g., centering) of the disk 130. In some implementations, a diameter of the opening 124 of the seat 120 is equal to twice the diameter of the disk 130 minus the diameter of the inner bore 112.

In one non-limiting, exemplary implementation of the valve 100, the outer diameter of the body 110 is 400 microns, the length or height of the body 110 is 1100 microns, the diameter of the inner bore 112 is 300 microns, the distance between the first port 114 and the lower surface of the seat 120 is 100 microns, the degree of curvature of the spherical portion 134 (FIG. 2B) of the disk 130 is 50 degrees, the thickness or height of the cylindrical portion 132 (FIG. 2B) of the disk 130 is 7 microns, the diameter of the cylindrical portion 132 of the disk 130 is 260 microns, the height of the spherical portion 134 (FIG. 2B) of the disk 130 is 29 microns, the distance between the upper surface of the seat 120 and the lower surface of each of the plurality of restrainers 122A-122D is 65 microns, and the distance between opposing ones of the plurality of alignment members 126A-126D is 275 microns.

While the disk 130 has been shown and described herein as having a cylindrical portion 132 and a spherical portion 134 (FIG. 2B), more generally, the disk 130 can have any suitable shape (or a combination of shapes) for inhibiting flow through the opening 124 of the seat 120 when the disk 130 is in the first position (FIGS. 2A and 2B). For example, in some implementations, the disk 130 does not include the cylindrical portion 132. As another example, in other implementations, the disk 130 has a generally conical portion that is disposed within or protrudes into the opening 124 to inhibit fluid flow.

Figure 5A:
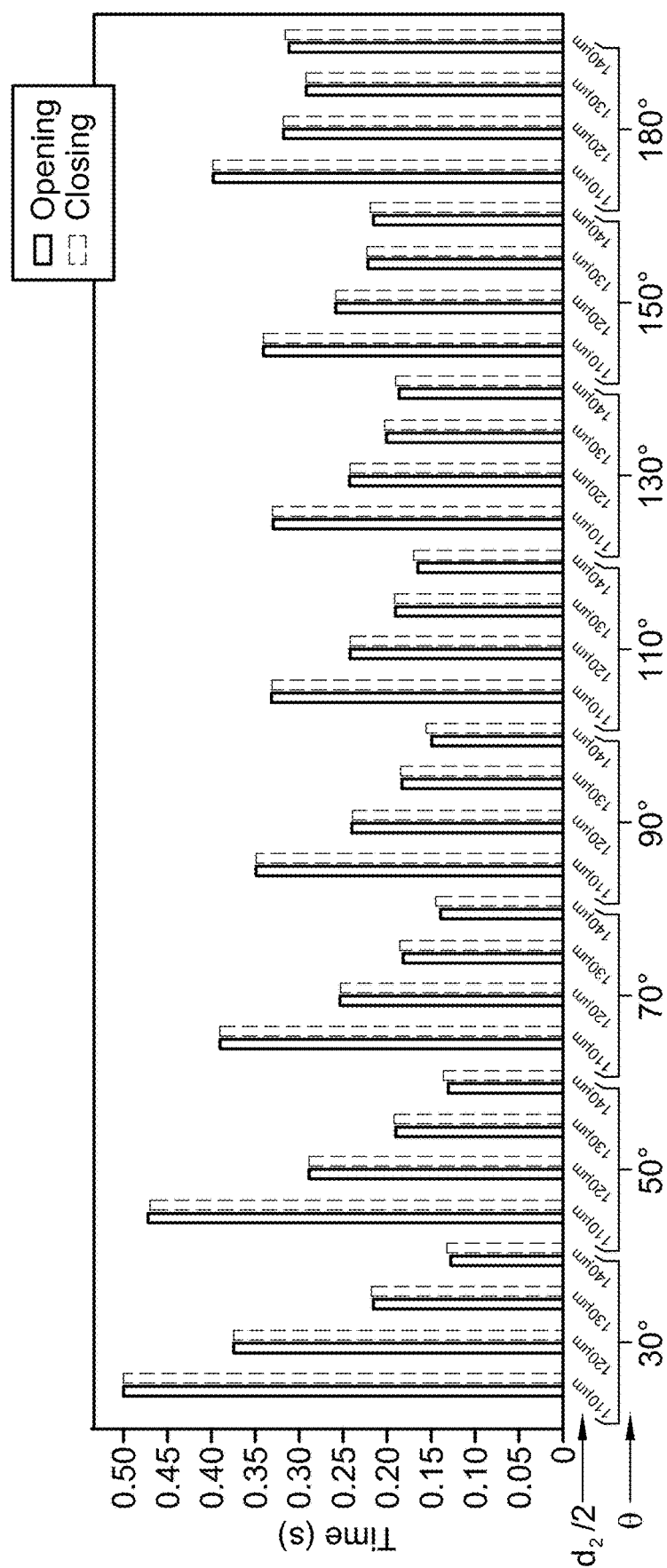
FIG. 5A is a graph showing simulated valve transition times versus different dimensional values of the disk of the valve of FIGS. 1A-2D according to some implementations of the present disclosure.
Figure 5B:
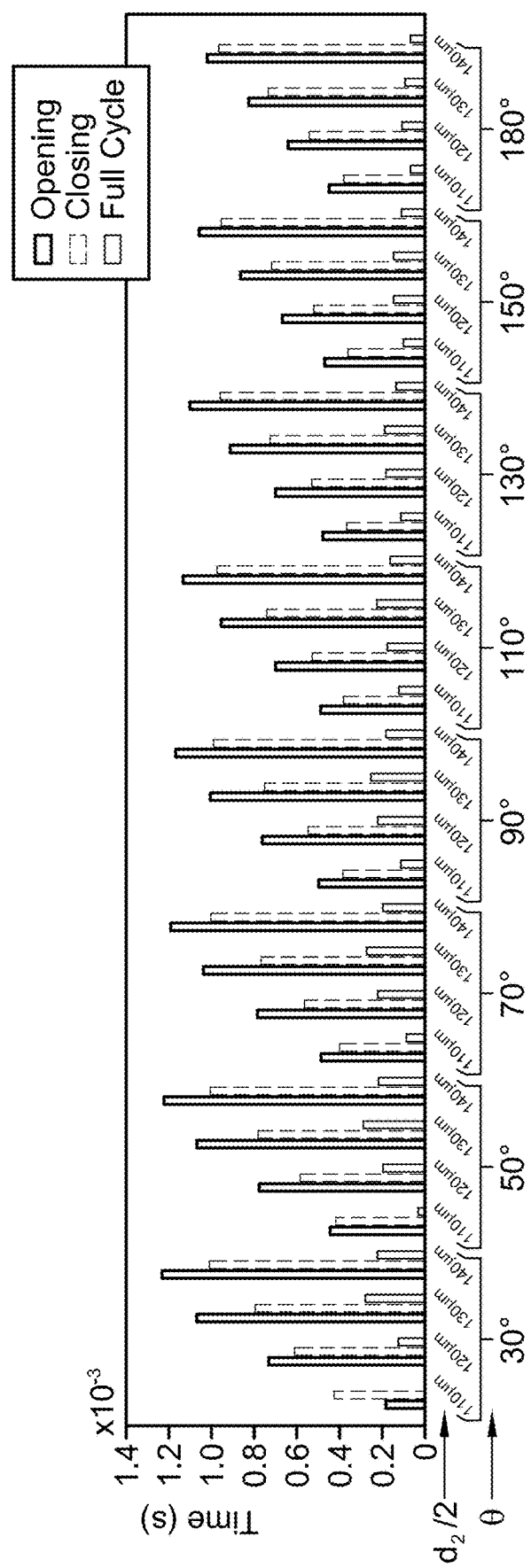
FIG. 5B is a graph showing simulated displaced volume per cycle versus different dimensional values of the disk of the valve of FIGS. 1A-2D according to some implementations of the present disclosure.

Referring generally to FIGS. 5A and 5B, a series of simulation of the function of valve 100 under bipolar pulsatile pressure (1 Hz, 0.1 Pa) using different dimensions are illustrated. FIG. 5A illustrates valve transition time (seconds) versus different values for the degree of curvature (θ) of the spherical portion 134 (FIG. 2B) of the disk 130 and the radius ($d_2/2$) of the cylindrical portion 132 (FIG. 2B) of the disk 130. The opening valve transition time is the time that it takes for the disk 130 to move from the first position (FIG. 2A) to the second position (FIG. 2C). Conversely, the closing valve transition time is the time that it takes for the disk 130 to move from the second position (FIG. 2C) to the first position (FIG. 2A). As shown, these opening/closing valve transition times were simulated for various values for the degree of curvature θ of the spherical portion 134 (e.g., 30°, 50°, 70°, 90°, 110°, 130°, 150°, 180°) and various values of the radius ($d_2/2$) of the cylindrical portion 132 (e.g., 110 microns, 120 microns, 130 microns, 140 microns). FIG. 5B illustrates displaced volume per cycle (μL) versus different values for the degree of curvature (θ) of the spherical portion 134 (FIG. 2B) of the disk 130 and the radius ($d_2/2$) of the cylindrical portion 132 (FIG. 2B) of the disk 130.

Figure 10:
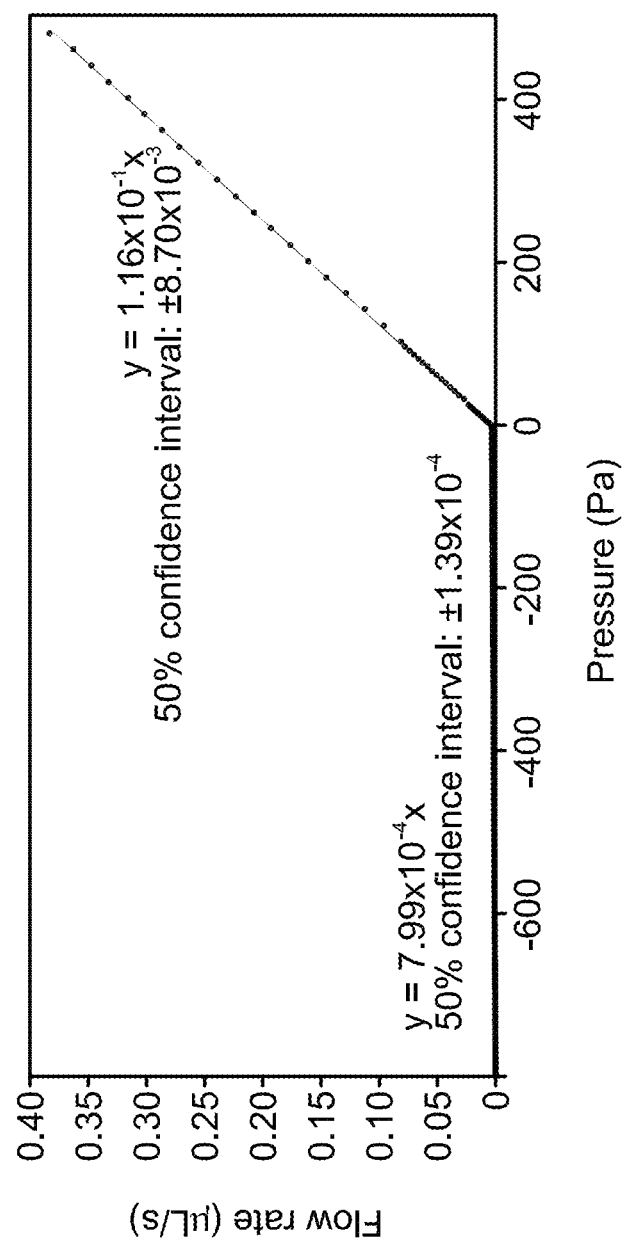
FIG. 10 is a graph showing exemplary flow rate values versus exemplary pressure values for the valve of FIGS. 1A-2D according to some implementations of the present disclosure.

Referring to FIG. 10, a graph illustrating exemplary flow rate values (μL/s) versus exemplary pressure differential values (Pa) for the valve 100 under a range of positive (opening the valve) and negative (closing the valve) pressure differential values is shown. The dots represent the acquired data and the black line represents a linear fit using a least squares method. The graph of FIG. 10 illustrates that the closed state (e.g., when the disk 130 of the valve 100 is in the first position (FIG. 2A)) exhibits two orders of magnitude higher resistance to fluid flow.

Figure 11B:
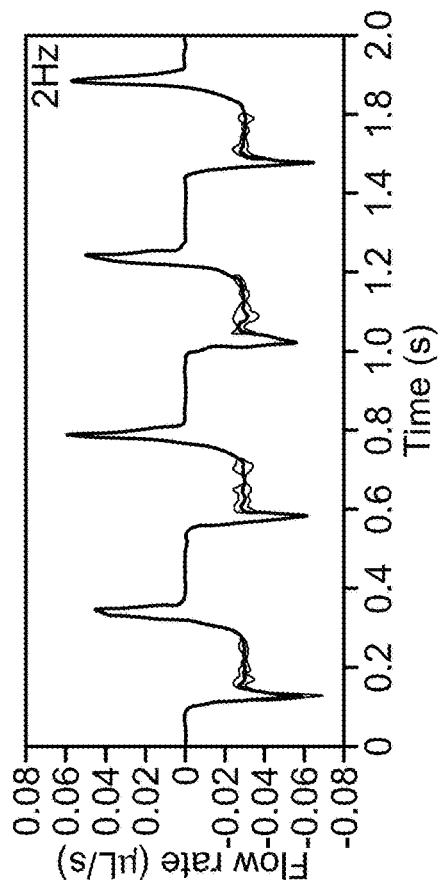
FIG. 11B is a graph showing exemplary flow rate values versus times for the valve of FIGS. 1A-2D at a second pulsatile cross-valve pressure frequency according to some implementations of the present disclosure.
Figure 11D:
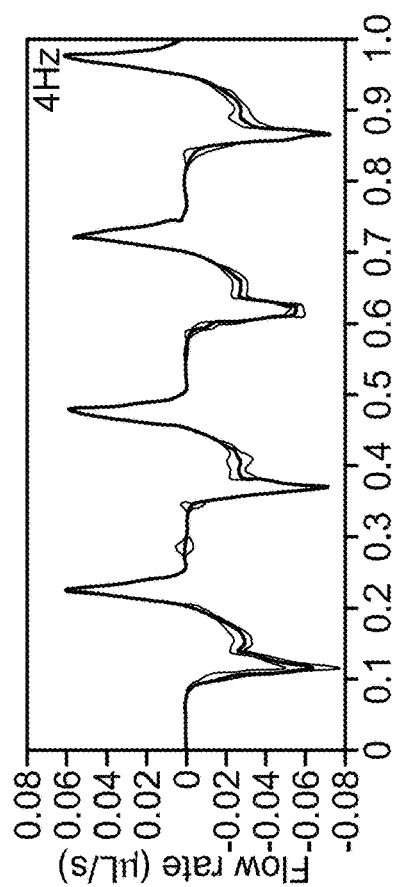
FIG. 11D is a graph showing exemplary flow rate values versus times for the valve of FIGS. 1A-2D at a fourth pulsatile cross-valve pressure frequency according to some implementations of the present disclosure.
Figure 11A:
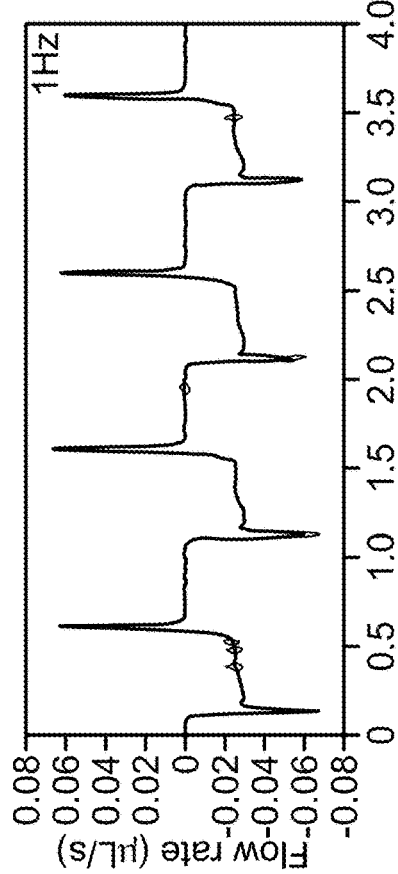
FIG. 11A is a graph showing exemplary flow rate values versus times for the valve of FIGS. 1A-2D at a first pulsatile cross-valve pressure frequency according to some implementations of the present disclosure.
Figure 11C:
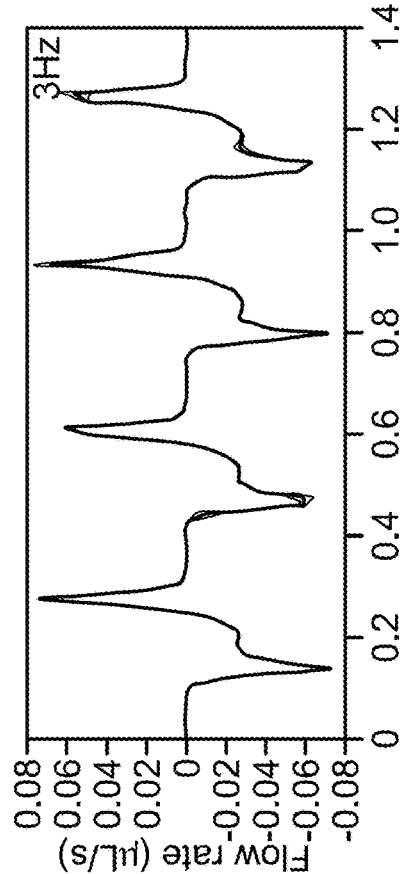
FIG. 11C is a graph showing exemplary flow rate values versus times for the valve of FIGS. 1A-2D at a third pulsatile cross-valve pressure frequency according to some implementations of the present disclosure.

Referring generally to FIGS. 11A-11D, a series of graphs illustrating exemplary flow rate values (Ws) versus time (seconds) for a plurality of frequencies are shown. FIGS. 11A-11D show the temporal profile of the flow rate of fluid (e.g., water) through an exemplary implementation of the valve 100 (FIGS. 1A-2D) described herein. A pulsatile cross-valve pressure in the form of a square pulse between −50 Pa and 50 Pa was applied at different frequencies across FIGS. 11A-11D. In FIG. 11A, frequency value is 1 Hz. In FIG. 11B, the frequency value is 2 Hz. In FIG. 11C, the frequency value is 3 Hz. In FIG. 11D, the frequency value is 4 Hz. The graphs show that the fluid flow is rectified towards negative values in all frequencies, with transition times less than 100 ms.

Figure 6A:
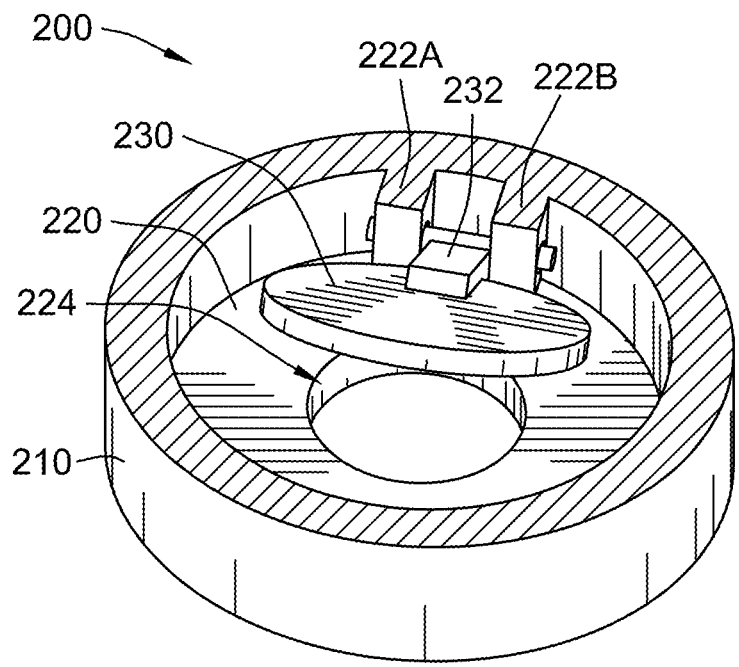
FIG. 6A is a cross-sectional view of a valve including a hinge according to some implementations of the present disclosure.
Figure 6B:
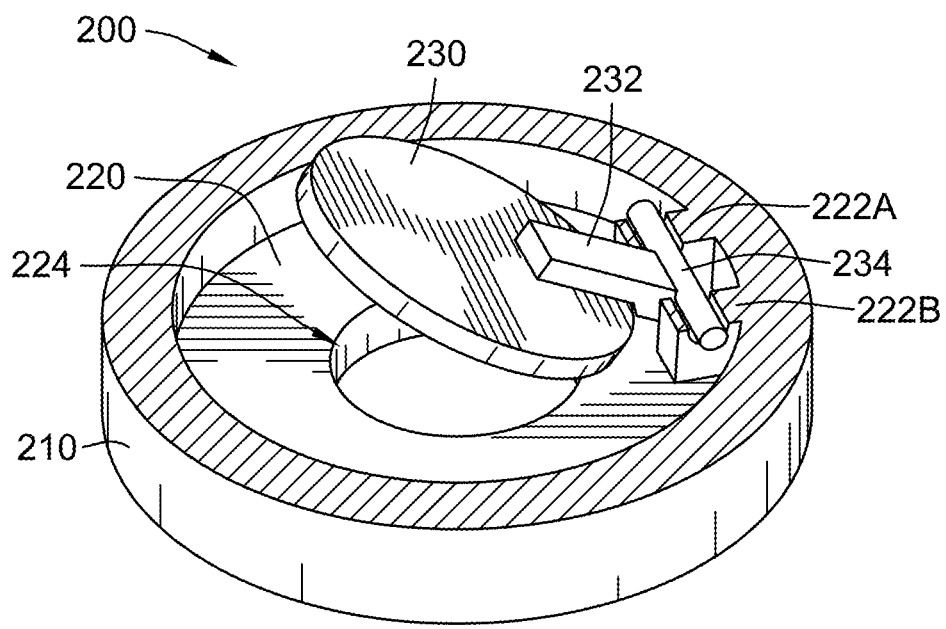
FIG. 6B is another cross-sectional view of the valve of FIG. 6A showing a pin of the hinge according to some implementations of the present disclosure.

Referring to FIGS. 6A and 6B, a valve 200 that is similar to the valve 100 (FIGS. 1A-2D) described herein is shown. The valve 200 is similar to the valve 100 in that the valve 200 includes a body 210 and a disk 230 that are similar to the body 110 and the disk 130 described herein. The body 210 includes a seat 220 with an opening 224 that is the same as, or similar to, the seat 120 and the opening 124 of the valve 100. While the disk 230 is shown and described herein as having a generally cylindrical or generally circular shape, other shapes that are suitably for covering the opening 224 are contemplate (e.g., rectangular, square, oval, triangular, polygonal, etc.)

The disk 230 differs from the disk 130 of the valve 100 in that the disk 230 includes a hinge 232 that is coupled to a first mounting portion 222A and a second mounting portion 222B of the seat 220. The hinge 232 rotates about a horizontal axis to cause the disk 230 to move relative to the opening 224 of the seat 220. Specifically, as shown in FIG. 6B, the hinge 232 includes a cylindrical pin 234 that is received within an aperture in each of the first mounting portion 222A and the second mounting portion 222B of the seat 220 to permit rotation of the hinge 232 relative to the seat 220. As shown in FIGS. 6A and 6B, the disk 230 is a second position that is similar to the second position of the disk 130 described herein (FIG. 2C) in that the disk 230 being in the second position permits fluid to fluid through the opening 224 in either direction. To inhibit or prevent fluid from flowing through the opening 224, the disk 230 is moveable to a first or closed position that is the same as or similar to the first position of the disk 130 (FIG. 2A) in that the in the first position, the disk 230 inhibits fluid flow through the opening 224.

Like the disk 130 of the valve 100 (FIGS. 1A-2D), the disk 230 is moveable between the first position and the second position responsive to a pressure differential across the opposing ends of the disk 230. That is, the disk 230 is moveable from the first position towards the second position responsive to application of a first predetermined pressure differential in a first direction, and moveable from the second position towards the first position responsive to application of a second predetermined pressure differential in a second opposing direction. The first predetermined pressure differential and/or the second predetermined pressure differential for the valve 200 can be the same as, or different than, the first and/or second predetermine pressures of the valve 100 described herein.

Exemplary Fabrication Methods

The valves described herein (e.g., valve 100 or valve 200) can generally be manufactured or fabricated using any suitable technique or method, such as, for example, photolithography, two-photon laser lithography, stereolithography, or reactive ion etching. While techniques like photolithography and stereolithography have higher throughput, these techniques generally have lower resolution than two-photon laser lithography techniques.

Two-photon direct laser writing (TDPLW) can reliably and reproducibly generate features with resolution of less than 1 micron, and it allows the valves described herein to be fabricated as a single process even in embodiments where the disk is not physically tethered to the body (e.g., like the disk 130 of the valve 100). That is, in implementations utilizing two-photon laser lithography, all of the components of the body 110 of the valve 100 are unitary and/or monolithic, and the disk 130 is manufactured concurrently or simultaneously with the body 110. The two-photon laser lithography process can use, for example, IP-Dip photoresist available from Nanoscribe GmbH of Stutensee, Germany, which allows for high printing resolution, high elastic modulus, high yield stress and high mechanical resilience even at high fluid pressures and impact forces.

As described above, in some implementations, the disk 130 includes a spherical portion 134 (FIG. 2B). To fabricate the spherical portion 134 with a high throughput, droplets of the desired material can be cast on a flat substrate (e.g., a silicon wafer). Electrowetting or coating (e.g., silanization, spin coating, vapor deposition, etc.) of the flat substrate can be used to control the contact angle between the monomer solution and the flat substrate to reproducibly define the degree of curvature of the spherical portion 134. The volume or amount of cast material solution can control the overall size of the final radius or degree of curvature and the size of the plate. The material droplets are then solidified to form the final part. As described in further detail herein, additional layers or bulk blocks of a different type of material can be added on the substrate and be encapsulated by the cast liquid droplet, or can be deposited (e.g., using vapor deposition, electroplating, sputtering, coating, etc.) on the solidified droplet. The independent fabrication of the disk allows access to materials not compatible with standard photolithography requirements and that would be eroded by the processes in photolithography protocols, and also allows processing of the disk without affecting the other features of the valve.

As a further alternative method, reactive ion etching can be used to fabricate the components of the valve (e.g., valve 100 and/or valve 200), where each component can be fabricated using the choice of a suitable eroding mask.

Exemplary Valve Component Materials

In addition to the materials described above (e.g., IP-Dip photoresist), the valves described herein (valve 100 and/or valve 200) can comprise one or more materials that provide additional functionality. For example, in some implementations, the disk 130 can comprise a piezoelectric material (e.g., a piezoelectric disk, a piezoelectric disk stack, a bimorph, etc.) that cam modify, in situ, the geometry of the disk 130 responsive to application of an external signal (e.g., an external electric field). Modification of the geometry of the disk 130 using a piezoelectric material can be used to, for example:

modify the flow resistance of the valve by changing the lateral and vertical spacing of the valve as a function of the external signal (e.g., as a function of an external electrical field intensity)

modify the efficacy of the contact (e.g., coaptation) between the disk 130 and the seat 120 modify the transition time, dead volume, and/or transition pressure between the open (first position) and closed (second position) states inhibit (e.g., completely prevent) fluid flow even when the disk 130 is in the open state (second position) and as an implementation of a close switch permit fluid flow even when the disk 130 in the closed state (first position) as an implementation of an open switch by, for example, impairing the coaptation efficiency between the disk and the seat In some implementations, the valves described herein can comprise a magnetic material (e.g., magnetic nanoparticles scattered within the disk 130, a piece(s) of magnetic material embedded in or completely making up the disk 130, magnetic coating deposited/developed on the disk, etc.) External magnetic actuators (e.g., permanent magnets or electromagnets) can be used to induce a magnetic field to, for example:

Dynamically actuate the disk 130 between the first position and the second position, rendering the valve an active valve (e.g., similar to a solenoid valve) instead of a passive pressure check valve Apply a predetermined force to the disk 130, biasing its position towards the closed state (first position) or open state (second position), and thus modifying the transition pressure In some implementations, the valves described herein can comprise a light modulated material (e.g., completely making up or coating consisting an appended piece on the disk 130) to modify the geometry of the disk 130 in the same or similar manner as described above for the piezoelectric material implementations. In some implementations, the valves described herein can comprise a swelling material (e.g., pH or osmotically induced swelling) to control the geometry of the disk, or to modify the stiffness of the disk 130. In some implementations, the valves described herein can comprise a degradable material (e.g., induced by pH, a chemical reagent added within medium, etc.) to modify the geometry or stiffness of the disk 130. In other implementations, the valves described herein can comprise a thermally expanding material to modify the geometry of the disk 130.

In some implementations, the valves described herein can include one or more materials that coat or fully comprise the disk 130, the seat 120, the plurality of alignment members 126A-H, and/or the plurality of restrainers 122A-D to modify the mechanical and/or chemical properties of the valve. For example, the seat 120, the plurality of restrainers 122A-D and/or the disk 130 can comprise a soft elastic material to improve coaptation efficiency and diodicity of the valve, as well as resilience to chronic wear, deformation, high pressures and impact forces between the disk 130, the seat 120 and the plurality of restrainers 122A-D upon closing (transition to first position) and opening (transition to second position) of the valve. Such soft elastic materials include, for example, conformal coating (e.g., parylene), kPa-MPa elastic modulus hydrogels and elastomers (e.g., polyethylene glycol based polymers or 4-hydroxybutyl acrylate). Using these soft elastic materials can decouple the coaptation efficiency from the geometrical resolution of the fabrication technique, and thus permit lower resolution fabrication methods (e.g., stereolithography, extrusion printing).

Similarly, in some implementations, the surface of any or all of the valve components can be coated with a hydrophilic or a hydrophobic layer to improve interaction with the hydrophilic or hydrophobic fluid, or to inhibit or reduce adhesion of contaminants in the fluid to the valve. These hydrophilic or hydrophobic coatings can be applied using, for example, chemical vapor deposition (e.g. silanization), physical vapor deposition, electroplating, or sputtering. In other implementations, the surface of any or all of the valve components can be coated with a chemically inert material to prevent degradation of the valve due to prolonged exposure to the medium or to reduce reactivity with the fluid. Similarly, the surface of any or all of the valve components can be coated with an insulating layer to inhibit or prevent contact of the valve materials with the fluid and prevent the release of toxic agents from the components of the valve (e.g., if the fluid includes or interfaces with a biological material).

In some implementations, the plurality of restrainers 122A-122D of the valve can be fabricated using a deformable material. The deformation can be passive, deforming as a function of the pressure applied on the restrainers 122A-122D by the disk 130 in the open state (second position). Alternative, the deformable material of the plurality of restrainers 122A-122D can be active, using any of the type of material and actuation mechanisms described above. Deformation of the plurality of restrainers 122A-122D can be used to, for example, increase mechanical resilience of the valve through passive bending of the restrainers 122A-122D under increased forward pressures or decrease the flow resistance of the valve under high forward pressures by increasing the vertical spacing when the restrainers 122A-122D passively bend. An actively deformable material can also be used to bias the position of the disk to the closed state (first position) or open state (second position), which would adjust the required forward or reserve pressure exerted by the fluid to induce transition between the open and the closed states. Active actuation can be used to control the value of the transition pressure.

EXEMPLARY APPLICATIONS

The valves (e.g., valve 100 and/or valve 200) described herein can be used in a variety of applications. For example, the valve 100 and/or the valve 200 can be used with (e.g., connected in series with) any fluidic system or device to induce unidirectional flow within all or portion(s) of the system. The valve 100 and/or the valve 200 can induce unidirectional flow either passively through actuation of differences in pressure of the medium, or actively using any of the actuation materials or methods described herein, to control the flow rate in portions(s) of the system (e.g. as a flow resistor) and to control the fluid communication between distinct portions (e.g., compartments) of the system.

In some implementations, the valve 100 and/or the valve 200 can be used in flow chemistry applications to physically isolate the reactants and terminate a reaction in the flow chamber. A passive implementation of the valve 100 and/or the valve 200 can be used, using reverse pressure to seal the valve; or an active instance, using the external actuating stimulus to seal the valve.

In some implementations, the valve 100 and/or the valve 200 can be used as a passive or active valve when integrated in microfluidic robotics systems to control the configuration and/or motion of the robot.

In some implementations, the valve 100 and/or the valve 200 can be used for generation of microfluidic droplets of arbitrary size and number in a multiphase system. In such implementations, the valve separates a reservoir of the droplet medium and a reservoir of formed droplets within the encapsulating medium. A passive valve can be used to rectify the flow of the droplet medium when the droplet medium reservoir is actuated by a periodic pressure or flow actuator. When the valve is in the open state, the droplet medium is ejected through the valve forming a droplet, while when the valve enters the closed state, the droplet is formed and is released into the formed droplet reservoir. The flow rate and opening frequency of the valve are controlled to allow the droplet medium to pass through the valve at the intended volume. With an active valve, the valve is externally set to open and close at the desired flow rate and frequency using the actuating stimulus under potentially constant cross-valve pressure.

In some implementations, the valves described herein can be used as a valve with a non-zero transition pressure. Any of the geometry altering and actuation materials or techniques described above can be used to exert a controllable force on the disk and push it towards the closed state (first position) or open state (second position). The controllable force can be fixed or dynamically controlled by the actuation stimulus and can dictate the value of the non-zero transition pressure.

In some implementations, the valves described herein can be used as an ultrasensitive flow-based pressure sensor. In such implementations, the valve is placed between an externally controlled pressure and a microfluidic system. If the valve opens and flow is detected, the cross-valve pressure in the system has exceeded the transition pressure. In a valve instance with active control over the transition pressure, the transition pressure value can be used to sweep the transition pressure of the valve. The system would have minimal dead volumes, and its accuracy would depend on the accuracy of passive or active mechanism that dictates the transition pressure of the valve.

In some implementations, the valves described herein can be used as an ultrasensitive pressure/vacuum relief valve. In such implementations, the valve 100 and/or the valve 200 is placed at the output line of a system whose pressure is within a predetermined range bounded by a predefined threshold. In such implementations, the valve is fabricated with a transition pressure matching the threshold of the system. If the system pressure crosses the predefined threshold, the valve opens, restoring the pressure to the desirable pressure range. An actively controlled valve can be used to dynamically regulate the predefined threshold and the pressure of the system.

In some implementations, the valves described herein can be used as an implantable valve (e.g. to substitute failing venous valves). The valve can be placed as-is within blood vessels, or with structural additions on the outer side of a hollow body to improve adhesion and stability within the vessel. In such implementations, biocompatible materials are used to fabricate or coat the valve components.

In some implementations, the valves described herein can be used as a valvular component of generalized flow rectifier. The valve serves to induce unidirectional flow when a cross-valve pressure actuation of dynamic and arbitrary polarity is applied.

In some implementations, the valves described herein can be used with organ-on-a-chip or other cell-containing technologies involving flow, to control the flow rate of media and/or to rectify the flow profile to enable pulsatile flow. The flow can be externally induced (e.g. using a pump or gravitational force), or it could be generated by contracting cells (skeletal muscle cells, smooth muscle cells, cardiomyocytes).

In some implementations, the valves described herein can be used as a drug switch in drug perfusion chambers, for example, in miniaturized implanted in-vivo drug delivery systems. The valve allows unidirectional ejection of the drug to the adjacent tissue/organ/circulation to prevent contamination of the drug stock. The valve resistance can be adjusted to minimize the ejected volume, allowing for higher drug concentrations and longer lasting drug stock. The small size and compact nature of the valve allows miniaturization of the system.

In some implementations, the valves described herein can be used as a valvular component of a wirelessly actuated system. The active valve material components described above can be used with a stimulus generator (e.g., electrical, optical, thermal, magnetic, etc.). A coupled antenna within the system can be used for electrical, magnetic and thermal actuation, an external light source can be used for optical actuation, and external heat generators or heating light sources can be used for thermal actuation.

In some implementations, the valves described herein (e.g., valve 100) can be used within a fluid network having any suitable purpose and function, including organ-on-a-chip applications where the pump comprises one component of multiple components connected in series, each containing a different type of tissue.

Cardiac Applications

One specific example of a micro-fluidic device that can be used with the valves described herein is a micro-cardiac device, which can be used to study cardiac function. The micro-cardiac device can be used, for example, to model the effect of hemodynamic load changes on cardiac function and the progression of ventricular cardiomyopathies as observed in vivo on a tissue, cellular and/or subcellular level. This modeling can be used to study, for example, the myocardial response to pathologically increased loading conditions, and how it correlates to changes in cellular morphology, subcellular architecture, gene expression and calcium handling. The micro-cardiac device acts as a cyclic pulsatile pressure generator to produce pumping action causing a unidirectional flow.

Referring to FIG. 7, a microfluidic system includes a first valve 100A, a second valve 100B, and a micro-cardiac device 300. The micro-cardiac device 300 includes a heart tube chamber 310, a first well 320, and a second well 330. A first channel portion 360A permits fluid communication between the first well 320 and the heart tube chamber 310 and a second channel portion 360B permits fluid communication between the heart tube chamber 310 and the second well 330. The heart tube chamber 310 includes cardiac tissue 312. The cardiac tissue 312 includes cardiomyocytes (cardiac muscle cells), though other suitable cell types (e.g., endothelial cells, fibroblasts, pacemaker cells, perivascular cells) can also be included.

The cardiac tissue 312 can self-generate contractions to apply pressure on fluid within the micro-cardiac device 300 and induce fluid flow. As shown in FIG. 7, the first valve 100A is positioned between the first well 320 and the heart tube chamber 310 and the second valve 100B is positioned between the heart tube chamber 310 and the second port 330. The first valve 100A and the second valve 100B are the same as, or similar to, the valve 100 (FIGS. 1A-2D) described herein. Alternatively, the valve 100A and/or the valve 200 can be the same as, or similar to, the valve 200 (FIGS. 6A-6B) described herein.

The cardiac tissue 312 is isolated from the rest of the fluid network through the first valve 100A and the second valve 100B. This allows fluid to enter cavity of the cardiac tissue 312 in the direction of arrow A from the first well 320 towards the cardiac tissue 312 through the first valve 100A during relaxation of the cardiac tissue 312, while at the same time the second valve 100B inhibits flow from the second port 330 and the cardiac tissue 312 in the direction opposite of arrow A. Conversely, during contraction of the cardiac tissue 312, the first valve 100A prevents fluid flow in the opposite direction of arrow A from the cardiac tissue 312 towards the first well 320, while the second valve 100B permits fluid flow in the direction of arrow A from the cardiac tissue 312 towards the second well 330. In other words, the first valve 100A and the second valve 100B cause unidirectional flow through the micro-cardiac device 300. While the microfluidic system in FIG. 7 is shown as including two valves (the first valve 100A and the second valve 100B), in other implementations, the microfluidic system can include any suitable number of valves that are the same as, or similar to, the first valve 100A and the second valve 100B (e.g., four valves).

Exemplary applications of the microfluidic system of FIG. 7 include modeling cardiac physiology and pathology in response to variation of blood pressure levels. In such applications, the liquid pressure in the input port of the first well 320 (preload pressure) and the pressure in the output port of the second well 30 (afterload pressure) can be different (e.g., the afterload pressure is higher). In this case, the pressure within the cardiac tissue 312 can oscillate between the preload and afterload pressures when the valves 100A and 100B rectify the fluid flow (e.g., the valves 100A and 100B open and close). This process mimics the function of the cardiac ventricles and their exposure to a cyclic oscillating level of blood pressure. Varying the preload and afterload pressure can model the effect of blood pressure changes on cardiac function.

Other exemplary applications of the microfluidic system of FIG. 7 includes use as a platform for drug screening regarding cardiotoxicity, where the pumping performance of the cardiac tissue 312 is used as one of the metrics of cardiac health. Additionally, the microfluidic system of FIG. 7 can be used as a platform for drug screening regarding the efficacy on pharmacological targets for cardiac disease, including hypertrophic and dilated cardiomyopathy, arrhythmia, cardiac inflammation, fibrosis, recovery from ischemic shocks, or any combination thereof. The system can also be used in organ-on-a-chip applications.

All aforementioned exemplary applications can be used in conjunction with specific cell lines of cardiac tissue that are derived from patients (e.g., either as primary cells or produced from induced pluripotent stem cells) as a tool of "personalized medicine" to study the behavior of the cardiac tissue of the specific patient.

Figure 8A:
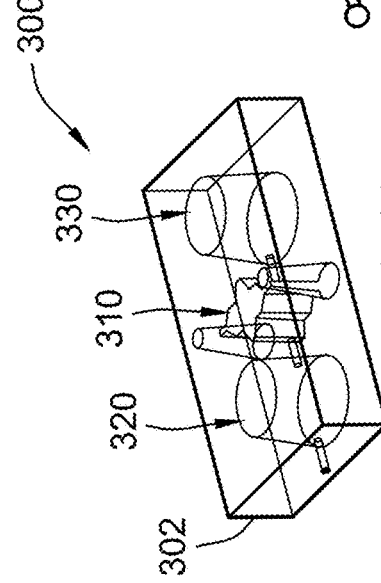
FIG. 8A is a perspective view of the micro-cardiac device of FIG. 7 during a first fabrication step according to some implementations of the present disclosure.

Referring now to FIGS. 8A-8F, an exemplary process for fabricating the micro-cardiac device 300 is illustrated. As shown in FIG. 8A, the fabrication process begins with a rectangular shaped body 302 comprising a material that is biocompatible with the heart tissue, such as, for example, Polydimethylsiloxane (PDMS). As described above, the micro-cardiac device 300 includes the heart tube chamber 310, the first well 320, and the second well 330, which are in fluid communication with one another via channels within the body 302. While the micro-cardiac device 300 is shown as having two wells (first well 320 and second well 330), in other implementations, the micro-cardiac device 300 can include any suitable number of wells.

Figure 8B:
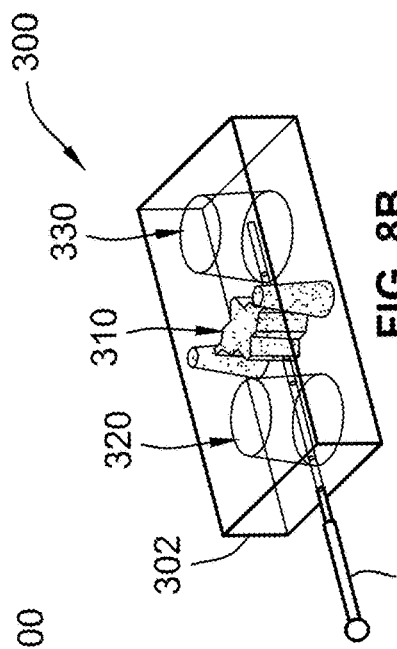
FIG. 8B is a perspective view of the micro-cardiac device of FIG. 7 during a second fabrication step according to some implementations of the present disclosure.
Figure 8C:
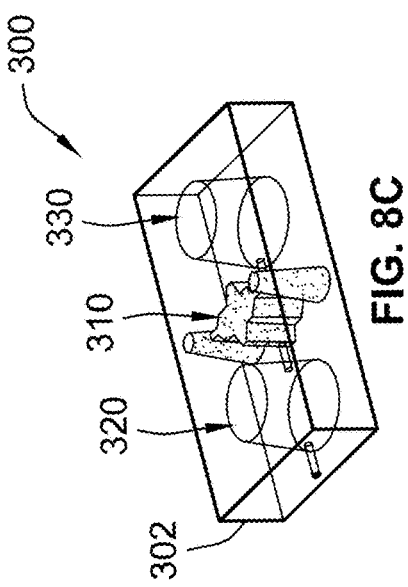
FIG. 8C is a perspective view of the micro-cardiac device of FIG. 7 during a third fabrication step according to some implementations of the present disclosure.

As shown in FIG. 8B, a first needle 340 is fit into the channels of the body 302, such that the first needle 340A extends into the heart tube chamber 310. A gel that provides structure support for the cardiac tissue (e.g., collagen) is inserted into the tube chamber 310 via the first needle 340A. After the gel is set (e.g., after gelation of the collagen) the needle 340 is removed from the body 302, leaving a hollow channel in the gel (e.g., collagen) in the heart tube chamber 310, as shown in FIG. 8B.

Figure 8D:
FIG. 8D is a perspective view of the micro-cardiac device of FIG. 7 during a fourth fabrication step according to some implementations of the present disclosure.

Next, as shown in FIG. 8D, a first needle guide 350A is inserted between the first well 320 and the heart tube chamber 310 and a second needle guide 350B is inserted between the heart tube chamber 310 and the second well 330. In some implementations, the needle guides 350A and/or 350B are fabricated using the same or similar methods as the valves described herein (e.g., the valve 100 and/or the valve 200). A second needle 340B is inserted into the channel of the body 302, crossing the heart tube chamber 310. The first and second needle guides 350A and 350B aid in guiding the second needle 340B through the channel made by the first needle 340A (FIG. 8B).

Figure 8E:
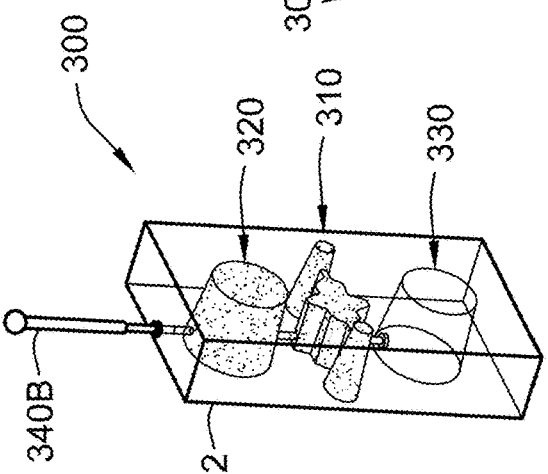
FIG. 8E is a perspective view of the micro-cardiac device of FIG. 7 during a fifth fabrication step according to some implementations of the present disclosure.
Figure 8F:
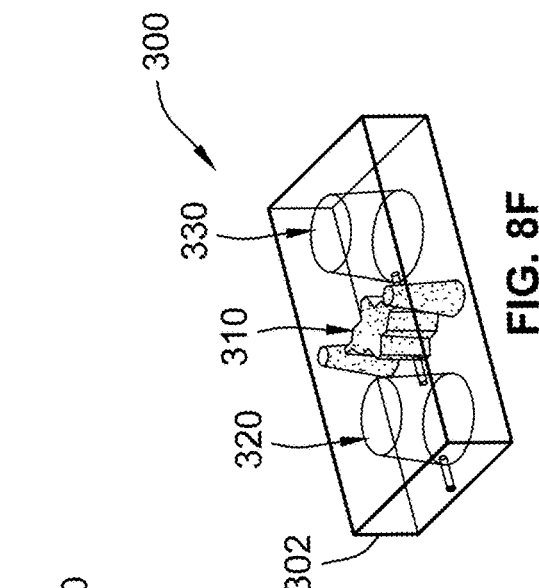
FIG. 8F is a perspective view of the micro-cardiac device of FIG. 7 during a sixth fabrication step according to some implementations of the present disclosure.

Thereafter, as shown in FIG. 8E, a mixture of cardiac cells, stromal cells and extracellular matrix (ECM) proteins (e.g., fibrin, collagen, Matrigel, other ECM proteins, or any combination thereof) is added to the first well 320 and the body 302 is tilted so that the cells precipitate through the channel into the hollow space in the heart tube chamber 310. After the aforementioned mixture is added, the second needle 340B, the plugs 350A and 350B, and the remainder of the gelled mixture that is not contained within the heart tube chamber 310 are removed, leaving behind a hollow channel in the heart tube chamber 310 lined with cardiac tissue, as shown in FIG. 8F.

Figure 9B:
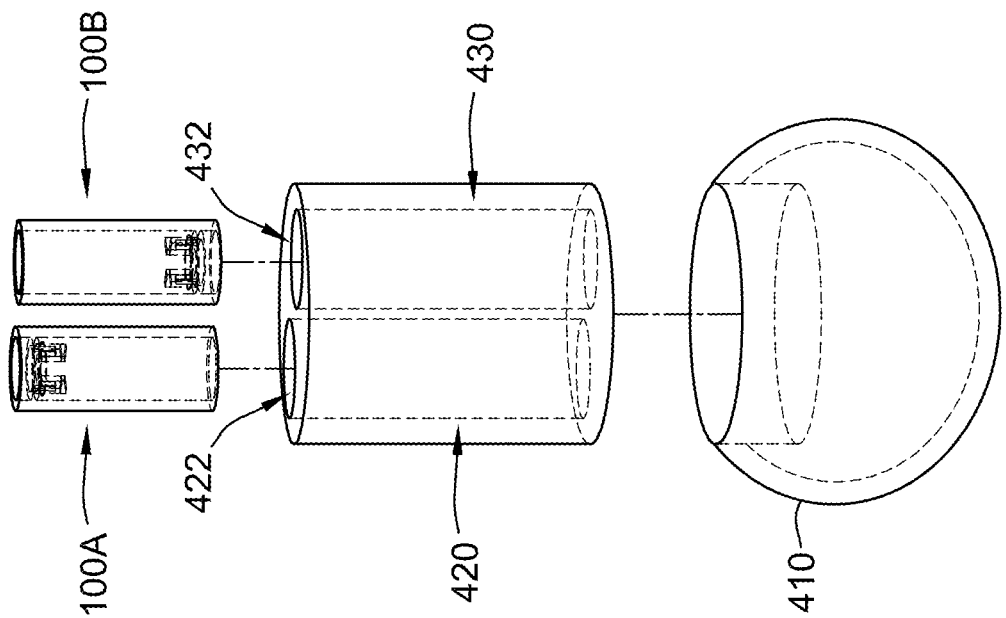
FIG. 9B is a perspective exploded view of the micro-cardiac device, first valve, and second valve of FIG. 9A according to some implementations of the present disclosure.
Figure 9A:
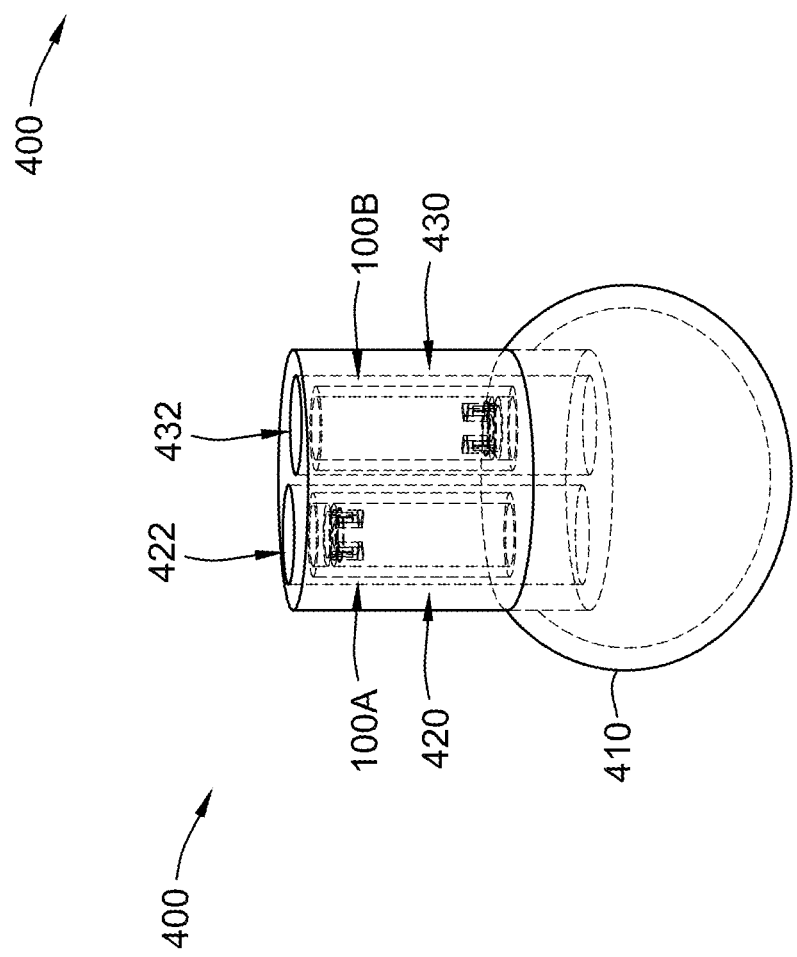
FIG. 9A is a perspective assembled view of a micro-cardiac device, a first valve, and a second valve according to some implementations of the present disclosure.

Referring generally to FIGS. 9A and 9B, an alternative microfluidic system 400 includes a concave cardiac tissue portion 410, a first port 420, a second port 430, the first valve 100A, and the second valve 100B. The first valve 100A and the second valve 100B are the same as, or similar to, the first valve 100A and the second valve 100B, respectively, in FIG. 7. The first port 420 has an inlet 422 and the second port 430 has an outlet 432. The concave cardiac tissue portion 410 is similar to the cardiac tissue 312 (FIG. 7) in that the concave cardiac tissue portion 410 can contract and relax to induce fluid flow through the system 400 and simulate cardiac function. In system 400, fluid enters through the inlet 422 of the first port 420 and exits through the outlet 432 of the second port 420.

In some implementations, metamaterial scaffolds are used to modulate the mechanical environment of living tissue. For example, the metamaterial is used as a mechanical stimulus to direct cellular growth, and tissue architecture. Accordingly, in another aspect provided herein is a scaffold composed of a metamaterial. The metamaterial scaffold comprises a structure defining a lumen. The outer surface of the structure comprises biological cells seeded thereon. For example, at least a portion of the outer surface, e.g., non-lumen surface of the structure can comprise a layer of biological cells.

The design and functionality of the scaffold depend on the type of organ or organ function one wishes to mimic. Thus, as noted above, the metamaterial scaffold can be of any shape or form that defines a lumen. For example, the structure defining a lumen can have a plain geometry. Some exemplary plain geometries include, but are not limited to tubular, sphere, hemisphere, bending tube and the like. The metamaterial scaffold can also be of geometry that resembles the native structure of a tissue or organ, e.g., a blood vessel. In some implementations, the metamaterial scaffold comprises a tubular structure defining first and seconds ends, and a lumen. In some implementations, the metamaterial scaffold is a tubular structure defining first and seconds ends, and the lumen. Generally, the first and second ends are open such that a fluid flow can occur through the tubular structure from the first end to the second end or vice versa. In some implementations, one of the first or second end is closed, i.e., a fluid flow does not occur through the closed end.

As used herein, a "metamaterial" is an assembly of multiple individual elements. These elements are fashioned from conventional materials such as metals or plastics, but the materials are usually arranged in specific periodic patterns. Therefore, metamaterials gain their properties not only from their composition, but also from their structures. Metamaterials have properties that are not found in the bulk materials, which can include electromagnetic radiation, sound waves, electrical properties and mechanical properties. Mechanical metamaterials are metamaterials which have mechanical properties that can be designed to have properties not found in nature.

In some implementations, the metamaterials are made using additive manufacturing methods. In some embodiments, the additive manufacturing method is TPDLW.

Exemplary mechanical metamaterials include "auxetic" materials, which are materials that exhibit a Negative Poisson's Ratio. Therefore, when an auxetic material is stretched by an applied force in a first direction, it becomes larger in a second direction perpendicular to the first direction. Alternatively, if an auxetic material is compressed by an applied force in the first direction, it becomes smaller in a second direction which is perpendicular to the first direction. The expansion in the second direction is not necessarily linearly related to expansion in the first direction due to the applied force, it is the general direction of expansion/contraction that defines an auxetic material. This is not a behavior that is generally found in nature where compression, for example, in one direction generally leads to an expansion of the material in a second direction.

It is noted that references to auxetic material herein include materials which are intrinsically auxetic and materials which have been rendered auxetic. Further, the auxetic, material may be a synthetic auxetic material and may have a macroscopic or microscopic auxetic structure. The auxetic material may be polymeric. The auxetic, material forming the scaffold may comprise a biodegradable polymer or polymers.

In some embodiments, scaffold uses a geometry of inverted hexagons in order to effect auxetic properties in the metamaterial scaffold which would otherwise not be auxetic. These "inverted hexagons" are not "regular" hexagons and instead essentially comprise a hexagon having first and second sides opposite and generally parallel to one another, and then third, fourth, fifth and sixth inwardly-inclined sides joining them. By linking chains of such inverted hexagons together via their third, fourth, fifth and/or sixth sides, then an auxetic structure can be created. Obviously, it is possible to incorporate into such structures inverted hexagons which are linked together via the vertices of their first and second sides, although this may result in non-auxetic regions whilst still retaining the overall auxetic properties.

FIG. 12A illustrates an "inverted hexagon" unit cell for an exemplary auxetic structure. FIG. 12B shows how the "inverted hexagon" unit cells can be interconnected to form the auxetic structure (e.g., lattice or mesh). The FIGS. 12A and 12B show how expansion in the vertical and horizontal direction are coupled. The dotted lines in FIG. 12B outline the expanded dimensions for the four-unit lattice and show how in the contracted state, the lattice dimensions are reduced in both horizontal and vertical directions.

As shown in FIG. 12A, the inverted hexagon unit cell comprises a set of six points A, B, C, D, E, and F, which are interconnected by six straight or curved members as follows: a first member interconnecting points A and B; a second member interconnecting points B and C; a third member interconnecting points C and D; a fourth member interconnecting points D and E; a fifth member interconnecting points E and F; and a sixth member interconnecting points F and A. In some implementations, the connections are beams of rectangular cross-section with 4×4 um size, the angle of the inverted hexagon (angle ABC in FIG. 12A) is 35 degrees, length of the member interconnecting points B and C is 240 um long, and the distance between points B and F in the relaxed state is 240 um The unit cells of inverted hexagons form the auxetic structure shown in FIG. 12B by connection of each unit cell to adjacent ones forming a mesh or 2D lattice. As shown, point D of a first unit cell is connected by a member (which can be curved or straight) to point A of an adjoining unit cell, a member BC of the first unit cell and member FE of adjoining unit cells are condensed forming a connection. Here "condensed" denotes that the two members become or form a single indistinguishable member and can refer to a straight or curved member, or to a point or vertex.

In some implementations, a cylindrical metamaterial scaffold is made by connection of rows where point D of a first unit cell is connected to an adjacent unit cell at point A until completing a band, forming a tubular structure. In another embodiment, a metamaterial scaffold is made by condensing of a member BC of a first unit cell with a member FE of another unit cell until completing a band and forming a structure.

FIGS. 12C and 12D illustrate another implementation of an auxetic structure, a "rotating square" structure. Here the unit cell can be described as comprising four squares as shown in FIG. 12C which are interconnected at vertices to form the auxetic structure. FIGS. 12C and 12D show how expansion in the vertical and horizontal direction are coupled, where the individual squares rotate (e.g., about and axis perpendicular to the plane containing the squares) to provide the expansion and contraction. The dotted lines in FIG. 12D outline the expanded dimensions for the lattice and show how in the contracted state, the lattice dimensions are reduced in both horizontal and vertical directions.

As shown in FIG. 12C, the rotating square unit cell can be described four squares with vertices which are labeled as G, H, I, J, K, L, M, N, O. P, Q and R, and which are interconnected by sixteen straight or curved members as follows: a first member interconnecting points G and H; a second member interconnecting points H and I; a third member interconnecting points I and J; a fourth member interconnecting points J and G; a fifth member interconnecting points J and K; a sixth member interconnecting points K and L; a seventh member interconnecting point L and M; an eight member interconnecting points M and J; a ninth member interconnecting points M and N; a tenth member interconnecting points N and O; an eleventh member interconnecting points O and P; a twelfth member interconnecting points P and M; a thirteenth member interconnecting points P and Q; a fourteenth member interconnecting points Q and R; a fifteenth member interconnecting points R and I; and sixteenth member interconnecting points I and P.

The rotating square unit cells form the auxetic structure shown in FIG. 12D by connection of each unit cell to adjacent ones forming a mesh or 2D lattice. As shown, in the horizontal direction, a point or vertices L from a first unit cell is condensed with point H of an adjacent cell, and a point N of the first unit cell is condensed with point R of the adjacent unit cell. In the vertical direction, the point G of the first unit cell is condensed with point Q of an adjacent unit cell, and the point K of the first unit cell is condensed with the point O of the adjacent unit cell.

In some implementations, a cylindrical metamaterial scaffold is made by connection of rows where point L from a first unit cell is condensed with point H of an adjacent cell, and a point N of the first unit cell is condensed with point R of the adjacent unit cell until completing a band, forming a tubular structure. In another embodiment, a cylindrical metamaterial scaffold is made wherein the point G of the first unit cell is condensed with point Q of an adjacent unit cell, and the point K of the first unit cell is condensed with the point O of the adjacent unit cell until completing a band and forming a tubular structure.

FIGS. 12E and 12F show additional implementations of auxetic structures. FIG. 12E shows a "star" structure, in a compressed form on the left and expanded form on the right. FIG. 12F shows a "rotating triangle" structure, compressed form on the left and expanded form on the right. The dashed lines indicate the approximate expanded dimensions and are added to help guide the eyes and show the effect of expansion and contraction. The rotating triangle unit cells form the auxetic structure shown in FIG. 12F by connection of each unit cell to adjacent ones forming a mesh or 2D lattice. As shown, each triangle unit cell is connected to three other each triangle unit cells. Each vertex is shared by two triangle unit cells.

In some implementations, the cylindrical metamaterial scaffold is made by connecting the lattice shown in FIG. 12B, FIG. 12D, FIG. 12E or FIG. 12F in directions other than the horizontal or vertical direction. For example, the lattice can form a band in a direction diagonal to the lattice or any angle between horizontal and vertical.

In some implementations, the auxetic structure of the scaffold comprises a plurality of unit cells, each unit cell comprising a set of eight points interconnected with eight straight or curved members as follows: a first member interconnecting points A and B; a second member interconnecting points B and C; a third member interconnecting points C and D; a fourth member interconnecting points C and E; a fifth member interconnecting points E and F; a sixth member interconnecting points F and G; a seventh member interconnecting points G and H; and an eighth member interconnecting points G and A. The unit cells form the auxetic structure by connection of each unit cell to adjacent ones forming a mesh or 2D lattice. For example, point D of first unit cell is connected by a member (which can be curved or straight) to point H of an adjoining unit cell and/or line AB of a first unit cell is condensed with EF of an adjoining cell.

To form the tubular structure, the unit cells are connected in rows until completing a band and forming a tubular structure. For example, the unit cells are connected in rows with the point D of one cell being connected to point H of an adjoining cell until completing a band, thereby forming the tubular structure. In this example, the unit cells can also be connected in columns along the length of the tubular structure with the line AB of one cell being condensed to line EF of an adjoining cell until spanning the length of the tubular structure.

In another example, the unit cells are connected in rows with the line AB of one cell being condensed to line EF of an adjoining cell until completing a band, thereby forming the tubular structure. In this example, the unit cells can also be connected in columns along the length of the tubular structure with the point D of one cell being connected to point H of an adjoining cell until spanning the length of the tubular structure.

In some implementations, the auxetic structure of the scaffold comprises a plurality of unit cells, each unit cell comprising a set of four points interconnected with four straight or curved members as follows: a first member interconnecting points I and J; a second member interconnecting points J and K; a third member interconnecting points K and L; and a fourth member interconnecting points L and I. The unit cells form the auxetic structure by connection of each unit cell to adjacent ones forming a mesh or 2D lattice. For example, point K of first unit cell is condensed to point I of an adjoining unit cell and/or point L of first unit cell is condensed to point J of an adjoining unit cell.

To form the tubular structure, the unit cells are connected in rows until completing a band and forming a tubular structure. For example, the unit cells are connected in rows with the point K of one cell being condensed to point I of an adjoining cell until completing a band and thereby forming the tubular structure. In this example, the unit cells can also be connected in columns along the length of the tubular structure with the point L of one cell being condensed to point J of an adjoining cell until spanning the length of the tubular structure.

In another example, the unit cells are connected in rows with the point L of one cell being condensed to point J of an adjoining cell until completing a band and thereby forming the tubular structure. In this example, the unit cells can also be connected in columns along the length of the tubular structure with the point K of one cell being condensed to point I of an adjoining cell until spanning the length of the tubular structure.

In some implementations, the auxetic structure of the scaffold of the present invention comprises a plurality of unit cells, each unit cell comprising a set of twelve points interconnected with twelve straight or curved members as follows: a first member interconnecting points A and B; a second member interconnecting points B and C; a third member interconnecting points B and D; a fourth member interconnecting points D and E; a fifth member interconnecting points E and F; a sixth member interconnecting points E and G; a seventh member interconnecting points G and H; an eighth member interconnecting points H and I; a ninth member interconnecting points H and J; a tenth member interconnecting points J and K; an eleventh member interconnecting points K and L; and a twelfth member interconnecting points K and A. The unit cells form the auxetic structure by connection of each unit cell to adjacent ones forming a mesh or 2D lattice. For example, point F of first unit cell is connected to point L of an adjoining unit cell and/or point C of first unit cell is connected to point I of an adjoining unit cell To form the tubular structure, the unit cells are connected in rows with the point F of one cell being connected to point L of an adjoining cell until completing a band and thereby forming the tubular structure. In this example; the unit cells can also be connected in columns along the length of the tubular structure with the point L of one cell being connected to point F of an adjoining cell until spanning the length of the tubular structure.

Alternatively, the unit cells are connected in rows with the point C of one cell being connected to point I of an adjoining cell until completing a band and thereby forming the tubular structure. In this example, the unit cells can also be connected in columns along the length of the tubular structure with the point C of one cell being connected to point I of an adjoining cell until spanning the length of the tubular structure.

While the above describe the case where the band of unit cells is vertical to the axial direction of the tubular structure by repeating the unit cell along the cell's horizontal or vertical direction, it is noted a cylindrical metamaterial scaffold can also be made by connecting the lattices and unit cells shown in FIGS. 12A-12F or described herein in directions other than the horizontal or vertical direction. For example, the unit cells can be connected to form a band in a direction diagonal to the lattice or any angle between horizontal and vertical.

The figures and descriptions of particular auxetic structures should not be construed as limiting embodiments since there are many known auxetic structures that can be implemented for the metamaterial scaffolds described herein. To allow for auxetic behavior, any other auxetic unit cell and structure can be used (Karnesis et al. Small Materials and Structures, 2013). In addition to two dimensional structures, the unit cells can be three dimensional. In some embodiments the combination of unit cells provides behaviors that include torsion upon compression/tension, in inhomogeneous anisotropy stiffness and can, for example, control bending when a particular force is applied. As used herein a lumen is the inside space of a tubular structure. In some embodiments, the lumen of the cylindrical metamaterial scaffold does not include any biological cells.

In some implementations, the lumen of the scaffold also comprises biological cells. In such implementations, the amount of biological cells in the lumen can be less than the amount of biological cells on the outer or non-lumen surface A skilled artisan can implant various types of cells, i.e., biological cells on the scaffold. Cells include any cell type from a multicellular structure, including nematodes, amoebas, up to mammals such as humans. Generally, cell types implanted on the scaffold depend on the type of organ or organ function one wishes to mimic, and the tissues that comprise those organs. It is noted that cells can be of single cell-type or mixture or co-culture of different types. One can also co-culture various stem cells, such as bone marrow cells, induced adult stem cells, embryonal stem cells or stem cells isolated from adult tissues on the scaffold of the invention. Exemplary cell types (e.g., human) which can be used include, but are not limited to cells of the integumentary system including but not limited to Keratinizing epithelial cells, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell); Wet stratified barrier epithelial cells, such as Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts); Exocrine secretory epithelial cells, such as Salivary gland mucous cell (polysaccharide-rich secretion). Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion), Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), pancreatic endocrine cells, Paneth cell of small intestine (lysozyme secretion), intestinal epithelial cells, Types I and II pneumocytes of lung (surfactant secretion), Clara cell of lung; hormone secreting cells, such as endocrine cells of the islet of Langerhands of the pancreas; Anterior pituitary cells, Somatotropes, Lactotropes, Thyrotropes, Gonadotropes, Corticotropes, Intermediate pituitary cell, secreting melanocyte-stimulating hormone; and Magnocellular neurosecretory cells secreting oxytocin or vasopressin; Gut and respiratory tract cells secreting serotonin, endorphin, somatostatin, gastrin, secretin, cholecystokinin, insulin, glucagon, bombesin; Thyroid gland cells such as thyroid epithelial cell, parafollicular cell, Parathyroid gland cells, Parathyroid chief cell, Oxyphil cell, Adrenal gland cells, chromaffin cells secreting steroid hormones (mineralcorticoids and gluco corticoids), Leydig cell of testes secreting testosterone, Theca interim cell of ovarian follicle secreting estrogen, Corpus luteum cell of ruptured ovarian follicle secreting progesterone, Granulosa lutein cells, Theca lutein cells, Juxtaglomerular cell (renin secretion), Macula densa cell of kidney, Peripolar cell of kidney, Mesangial cell of kidney; Metabolism and storage cells such as Hepatocyte (liver cell), White fat cell, Brown fat cell, Liver lipocyte. One can also use Barrier function cells (Lung, Gut, Exocrine Glands and Urogenital Tract) or Kidney cells such as Kidney glomerulus parietal cell, Kidney glomerulus podocyte, Kidney proximal tubule brush border cell, Loop of Henle thin segment cell, Kidney distal tubule cell, Kidney collecting duct cell; Type I pneumocyte (lining air space of lung), Pancreatic duct cell (centroacinar cell), Nonstriated duct cell (of sweat gland, salivary gland, mammary gland, etc.), principal cell, Intercalated cell, Duct cell (of seminal vesicle, prostate gland, etc.), Intestinal brush border cell (with microvilli), Exocrine gland striated duct cell, Gall bladder epithelial cell, Ductulus efferens nonciliated cell, Epididymal principal cell, Epididymal basal cell; Epithelial cells lining closed internal body cavities such as Blood vessel and lymphatic vascular endothelial fenestrated cell, Blood vessel and lymphatic vascular endothelial continuous cell, Blood vessel and lymphatic vascular endothelial splenic cell. Synovial cell (lining joint cavities, hyaluronic acid secretion), Serosal cell (lining peritoneal, pleural, and pericardial cavities), Squamous cell (lining perilymphatic space of ear), Squamous cell (lining endolymphatic space of ear), Columnar cell of endolymphatic sac with microvilli endolymphatic space of ear), Columnar cell of endolymphatic sac without microvilli endolymphatic space of ear), Dark cell (lining endolymphatic space of ear), Vestibular membrane cell (lining endolymphatic space of ear), Stria vascularis basal cell (lining endolymphatic space of ear), Stria vascular is marginal cell (lining endolymphatic space of ear), Cell of Claudius (lining endolymphatic space of ear), Cell of Boettcher (lining endolymphatic space of ear), Choroid plexus cell (cerebrospinal fluid secretion), Pia-arachnoid squamous cell, Pigmented ciliary epithelium cell of eye, Nonpigmented epithelium cell of eye, Corneal endothelial cell; Ciliated cells with propulsive function such as Respiratory tract ciliated cell, Oviduct ciliated cell (in female), Uterine endometrial ciliated cell (in female), Rete testis ciliated cell (in male), Ductulus efferens ciliated cell (in male), Ciliated ependymal cell of central nervous system (lining brain cavities); cells that secrete specialized ECMs, such as Ameloblast epithelial cell (tooth enamel secretion), Planum semilunatum epithelial cell of vestibular apparatus of ear (proteoglycan secretion), Organ of Corti interdental epithelial cell (secreting tectorial membrane covering hair cells). Loose connective tissue fibroblasts, Corneal fibroblasts (corneal keratocytes), Tendon fibroblasts, Bone marrow reticular tissue fibroblasts. Other nonepithelial fibroblasts, Pericyte, Nucleus pulposus cell of intervertebral disc, Cementoblast/cementocyte (tooth root bonelike cementum secretion), Odontoblast/odontocyte (tooth dentin secretion), Hyaline cartilage chondrocyte, Fibrocartilage chondrocyte, Elastic cartilage chondrocyte, Osteoblast/osteocyte, Osteoprogenitor cell (stem cell of osteoblasts), Hyalocyte of vitreous body of eye, Stellate cell of perilymphatic space of ear, Hepatic stellate cell (Ito cell), Pancreatic stellate cell; contractile cells, such as Skeletal muscle cells, Red skeletal muscle cell (slow), White skeletal muscle cell (fast); Intermediate skeletal muscle cell, nuclear bag cell of muscle spindle, nuclear chain cell of muscle spindle, Satellite cell (stem cell), Heart muscle cells; Ordinary heart muscle cell, Nodal heart muscle cell, Purkinje fiber cell, Smooth muscle cell (various types), Myoepithelial cell of iris, Myoepithelial cell of exocrine glands; Blood and immune system cells, such as Erythrocyte (red blood cell), Megakaryocyte (platelet precursor), Monocyte, Connective tissue macrophage (various types); Epidermal Langerhans cell, Osteoclast (in hone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell. Reticulocyte, Stem cells and committed progenitors for the blood and immune system (various types); Nervous system cells, Sensory transducer cells such as Auditory inner hair cell of organ of Corti, Auditory outer hair cell of organ of Corti, Basal cell of olfactory epithelium (stem cell for olfactory neurons), Cold-sensitive primary sensory neurons, Heat-sensitive primary sensory neurons, Merkel cell of epidermis (touch sensor), Olfactory receptor neuron, Pain-sensitive primary sensory neurons (various types); Photoreceptor cells of retina in eye including Photoreceptor rod cells, Photoreceptor blue-sensitive cone cell of eye, Photoreceptor green-sensitive cone cell of eye, Photoreceptor red-sensitive cone cell of eye, Proprioceptive primary sensory neurons (various types); Touch-sensitive primary sensory neurons (various types); Type I carotid body cell (blood pH sensor); H carotid body cell (blood pH sensor); Type I hair cell of vestibular apparatus of ear (acceleration and gravity); Type II hair cell of vestibular apparatus of ear (acceleration and gravity); Type I taste bud cell; Autonomic neuron cells such as Cholinergic neural cell (various types), Adrenergic neural cell (various types), Peptidergic neural cell (various types) in the present device. Further, sense organ and peripheral neuron supporting cells can also be used. These include, for example, inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Type I taste bud supporting cell, Olfactory epithelium supporting cell, Schwann cell, Satellite cell (encapsulating peripheral nerve cell bodies) and/or Enteric glial cell. In some embodiments, one can also use central nervous system neurons and glial cells such as Astrocyte (various types), Neuron cells (large variety of types, still poorly classified), Oligodendrocyte, Spindle neuron; Anterior lens epithelial cell and Crystallin-containing lens fiber cell; pigment cells such as melanocytes and retinal pigmented epithelial cells; and germ cells, such as Oogonium/Oocyte, Spermatid, Spermatocyte, Spermatogonium cell (stem cell for spermatocyte), and Spermatozoon; membrane nurse cells such as Ovarian follicle cell, Sertoli cell (in testis), Thymus epithelial cell; and interstitial cells such as interstitial kidney cells.

In some implementations, cells that are seeded onto the metamaterial scaffold are selected from the group consisting of cardiac, bone, skeletal muscle, smooth muscle, pulmonary (e.g., for simulating the alveoli and their expansion), esophageal and stomachal (e.g., simulating the smooth muscle contraction), intestinal (simulating the peristaltic contraction and the geometrical complexity of the villi) and vascular cells (simulating the lumen shape, its contraction and constriction during vasoconstriction and vasodilation, and its stretch under pulsatile blood pressure). In some embodiments cells that are supported by or grown onto the metamaterial scaffold are cardiomyocytes.

In some implementations, the metamaterial scaffold can be made hollow, e.g., with pores on the surface, for example, to mimic the vascular system. The hollow network within the scaffold can be connected to a different series of channels and such hollow metamaterial scaffolds can be used for perfusing the scaffold and the tissue with any medium (e.g. as a way of vascularization or drug perfusion). A homogeneous perfusion can prevent necrosis of tissue due to poor nutrient diffusion, making thicker tissues viable.

In some implementations, the lumen has a diameter between about 0.005 mm and about 50 mm, a diameter that is less than about 5 mm, a diameter that is less than about 1 mm, a diameter that is less than about 0.1 mm or a diameter that is less than about 0.01 mm. In some implementations, the lumen has a diameter between about 0.008 mm and about 25 mm. In some implementations, the lumen has a diameter of about 1 mm. In some implementations, a length of the lumen is about 1.2 mm.

The scaffolds described herein can be fabricated from a biocompatible material. As used herein, the term "biocompatible material" refers to any polymeric material that does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include derivatives and copolymers of a polyimides, poly(ethylene glycol), polyvinyl alcohol, polyethyleneimine, and polyvinylamine, polyacrylates, polyamides, polyesters, polycarbonates, and polystyrenes.

In some implementations, the scaffold can be fabricated from a material selected from the group consisting of polydimethylsiloxane, polyimide, polyethylene terephthalate, polymethylmethacrylate, polyurethane, polyvinylchloride, polystyrene polysulfone, polycarbonate, polymethylpentene, polypropylene, a poly dine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly(ethylene glycol), styrene-acrylonitrile resin, poly(trimethylene terephthalate), polyvinyl butyral, polyvinylidenedifluoride, poly(vinyl pyrrolidone), and any combination thereof.

In some implementations, the scaffolds described herein can be fabricated from a degradable material, for example, for the purpose of initially directing tissue growth until the tissue generates its own sufficient extracellular matrix to stabilize its structure (e.g., osteogenic tissue). Degradability can be achieved either by using a material that can be degraded by the cells, or where degradation is externally induced by adding a soluble component that destabilizes the material's structure.

The scaffolds described herein can generally be manufactured or fabricated using any suitable technique or method, such as, for example, photolithography, two-photon laser lithography, stereolithography, reactive ion etching, or using molding where the mold is fabricated using any appropriate technique, including the aforementioned.

The material of the scaffold can be varied depending on the application and printing technique. In some implementations, the surface properties and chemistry of the scaffold are varied, either uniformly (e.g. plasma etching, chemical vapor deposition, and silanization) or selectively at desired locations on the scaffold. Selective modification can be achieved, for example, by using TPDLW to append a second photoresist on top of the initial resist with different properties. Through selective application of the second resist, it is possible to control the affinity of cells on the scaffold and create patterns of adhesion sites on the scaffold (Richter et al. Advanced Materials, 2017). In some implementations, the chemical properties of the surface are modified through passivation/activation, thus changing the affinity of other substances on the surface (e.g., for metal deposition and fluorescent labeling—Ceylan et al. Advanced Materials, 2017). In some implementations, an electrically conductive material can be used to print the scaffold or to pattern the printed scaffold. Thus, in some implementations, electrodes are included in or on the scaffold, that can be used for electrical stimulation and/or recording.

Any suitable method can be used for seeding cells on the scaffold. For example, a needle can be inserted in the lumen and the scaffold incubated in a culture of appropriate cells. After sufficient period of time to allow the cells to adhere on the scaffold, the needle can be removed from the lumen, Also provided herein is a microfluidic device comprising a cylindrical scaffold described herein and a valve described herein in fluid communication with each other.

Figure 13:
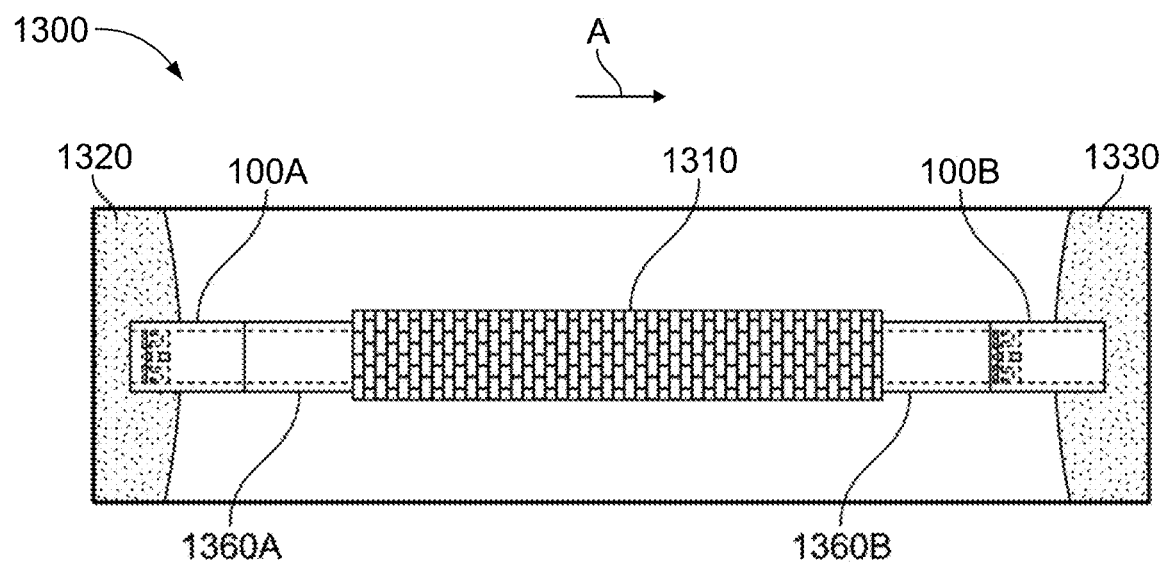
FIG. 13 is a top view of a microfluidic device comprising a first valve, a second valve and a cylindrical scaffold according to some implementations of the present disclosure.

Referring to FIG. 13, an exemplary microfluidic device 1300 includes a first valve 100A, a second valve 100B, a cylindrical scaffold 1310, a first port 1320, and a second port 1330. A first channel portion 1360A permits fluid communication between the first port 1320 and the cylindrical scaffold 1310 and a second channel portion 1360B permits fluid communication between the cylindrical scaffold 1310 and the second port 1330. In some embodiments, the cylindrical scaffold 1310 includes cardiomyocytes and, optionally, other suitable cell types, such as endothelial cells, fibroblasts, pacemaker cells, and/or perivascular cells.

The cylindrical scaffold 1310 can self-generate contractions to apply pressure on fluid within the microfluidic device 1300 and induce fluid flow. As shown in FIG. 13, the first valve 100A is positioned between the first port 1320 and the cylindrical scaffold 1310 and the second valve 100B is positioned between the cylindrical scaffold 1310 and the second port 1330. The first valve 100A and the second valve 100B are the same as, or similar to, the valve 100 (FIGS. 1A-2D) described herein. Alternatively, the valve 100A and/or the valve 200 can be the same as, or similar to, the valve 200 (FIGS. 6A-6B) described herein.

The cylindrical scaffold 1310 is isolated from the rest of the fluid network through the first valve 100A and the second valve 100B. This allows fluid to enter lumen of the cylindrical scaffold 1310 in the direction of arrow A through the first valve 100A and the first port 1320 during relaxation of the cardiomyocytes seeded on the cylindrical scaffold 1310, while at the same time the second valve 100B inhibits flow from the second port 1330 towards the cylindrical scaffold 1310 in the opposite direction of arrow A. Conversely, during contraction of the cardiomyocytes seeded on the cylindrical scaffold 1310, the first valve 100A prevents fluid flow in the opposite direction of arrow A towards the first port 1320, while the second valve 100B permits fluid flow in the direction of arrow A from cylindrical scaffold 1310 towards the second port 1330. In other words, the first valve 100A and the second valve 100B cause unidirectional flow through the micro-cardiac device 1300. While the microfluidic device in FIG. 13 is shown as including two valves (the first valve 100A and the second valve 100B), in other implementations, the microfluidic device can include any suitable number of valves that are the same as, or similar to, the first valve 100A and the second valve 100B (e.g., four valves).

Figure 14:
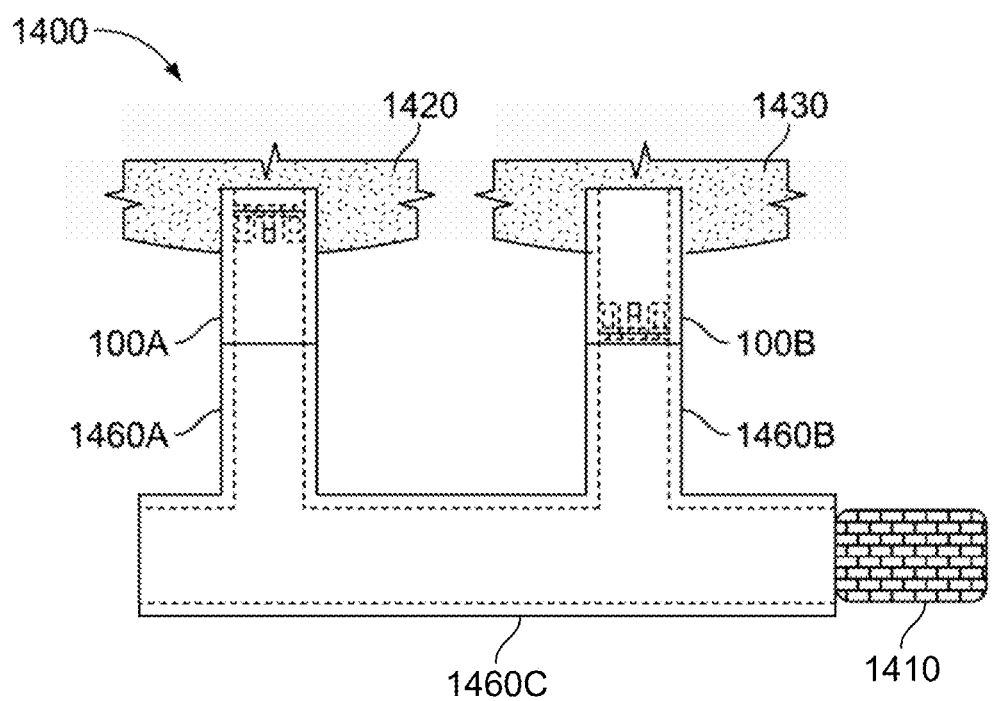
FIG. 14 is a top view of a microfluidic device comprising a first valve, a second valve and a cylindrical scaffold according to some implementations of the present disclosure.

Referring generally to FIG. 14, another exemplary microfluidic device 1400 includes a first valve 100A, a second valve 100B, a first port 1420, a second port 1430, and a cylindrical scaffold 1410. A first channel portion 1460A permits fluid communication between the first port 1420 and the cylindrical scaffold 1410 via a second channel portion 1460C. A third channel portion 1460B permits fluid communication between the second port 1430 and the cylindrical scaffold 1410 via the second channel portion 1460C. In some embodiments, the cylindrical scaffold 1410 includes cardiomyocytes and, optionally, other suitable cell types, such as endothelial cells, fibroblasts, pacemaker cells, and/or perivascular cells.

The cylindrical scaffold 1410 can self-generate contractions to apply pressure on fluid within the micro-cardiac device 1400, induce fluid flow and simulate cardiac function. In system 1400, fluid enters through the first port 1420 and exits through the second port 1430, or vice versa.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

ALTERNATIVE IMPLEMENTATIONS

Implementation 1.

A valve comprises a body including an inner bore extending between a first port and a second port, a seat, and one or more restrainers, and a disk that is moveable between the seat and the one or more restrainers such that (i) a first pressure that is less than 1 pascal and applied in a first direction causes the disk to move from a first position towards a second position to permit fluid communication between the first port and the second port and (ii) a second pressure that is less than 1 pascal and applied in a second opposing direction causes the disk to move from the second position towards the first position to inhibit fluid communication between the first port and the second port.

Implementation 2.

The valve according to implementation 1, wherein the first pressure and the second pressure are less than 0.5 pascals.

Implementation 3.

The valve according to implementations 1 or 2, wherein the first pressure is between about 0.1 pascals and about 0.5 pascals.

Implementation 4.

The valve according to any one of implementations 1-3, wherein the second pressure is between about 0.05 pascals and about 0.2 pascals.

Implementation 5.

The valve according to any one of implementations 1-4, wherein the disk is moveable such that the first pressure causes the disk to move from the first position to the second position in less than 500 milliseconds.

Implementation 6.

The valve according to any one of implementations 1-5, wherein the body is cylindrical and has a first diameter is that is 400 microns or less and a longitudinal length that is 1110 microns or less, and the inner bore is cylindrical and has a second diameter that is 300 microns or less.

Implementation 7.

The valve according to any one of implementations 1-6, wherein a distance between the disk and the one or more restrainers is between about 10 microns and about 30 microns responsive to the disk being in the second position.

Implementation 8.

The valve according to any one of implementations 1-7, wherein the body is rigid.

Implementation 9.

The valve according to any one of implementations 1-8, wherein the body is monolithic.

Implementation 10.

The valve according to any one of implementations 1-9, wherein the disk includes a cylindrical portion and a spherical portion, wherein a portion of the spherical portion contacts the seat responsive to the disk being in the first position to aid inhibiting fluid communication between the first port and the second port.

Implementation 11.

The valve according to any one of implementations 1-10, wherein the spherical portion of the disk has a degree of curvature that is between about 30 degrees and about 60 degrees.

Implementation 12.

The valve according to any one of implementations 1-11, wherein a distance between the first port and the seat is between about 5% and about 15% of a longitudinal length of the body.

Implementation 13.

A valve for use in a microfluidic system, the valve comprising a body including an inner bore extending between a first port and a second port, a seat having an opening and being disposed within the inner bore, and a plurality of restrainers positioned between the seat and the second port, and a disk that is moveable relative to the seat and the plurality of restrainers such that application of a first predetermined pressure that is between about 0.05 pascals and 1 pascal causes the disk to move from a first position towards a second position to permit fluid communication between the first port and the second port.

Implementation 14.

The valve according to implementation 13, wherein the disk inhibits fluid communication between the first port and the second port responsive to being in the first position.

Implementation 15.

The valve according to implementation 14, wherein a spherical portion of the disk is partially disposed within the opening of the seat to aid in inhibiting fluid communication between the first port and the second port responsive to the disk being in the first position.

Implementation 16.

The valve according to implementations 14 or 15, wherein the disk is moveable such that application of a second predetermined pressure causes the disk to move from the second position towards the first position to inhibit fluid communication between the first port and the second port.

Implementation 17.

The valve according to implementation 16, wherein the first predetermined pressure is different than the second predetermined pressure.

Implementation 18.

The valve according to any of implementations 13-17, wherein the disk includes a spherical portion and a cylindrical portion having a first diameter that is less than a second diameter of the inner bore.

Implementation 19.

The valve according to implementation 18, wherein a third diameter of the opening of the seat is equal to or smaller than twice the first diameter minus the second diameter.

Implementation 20.

The valve according to any one of implementations 13-19, wherein the body is monolithic.

Implementation 21.

A micro-fluidic system comprising a micro-cardiac device including a heart tube chamber containing cardiac cells, a first port, a second port, the heart tube chamber, the first port, and the second port, the first port being in fluid communication with the heart tube chamber via a first channel portion, the second port being in fluid communication with the heart tube chamber via a second channel portion; a first valve disposed in the first channel portion; and a second valve disposed in the second channel portion, wherein the first valve and the second valve are configured to cause unidirectional flow through the heart tube chamber.

Implementation 22.

A method for making a micro-cardiac device, the method comprising: inserting a first needle of a first diameter into a channel of a body such that the first need extends into a heart tube chamber disposed within the body; injecting a gel into the heart tube chamber via the first needle; removing the first needle subsequent to setting of the gel; inserting a first needle guide between a first well and the heart tube chamber; inserting a second needle guide between the heart tube chamber and a second well; inserting a second needle of a second diameter smaller than the first diameter into the channel such that the second needle extends into the heart tube chamber; injecting cells into the heart tube chamber; and removing the second needle.

Implementation 23.

The method according to claim 22, wherein the cells include cardiac cells, stromal cells, extracellular matrix (ECM) proteins, fibrin, collagen, Matrigel, or any combination thereof Implementation 24.

The method according to claim 22 or 23, wherein the gel is collagen, fibrin, Matrigel, a synthetic hydrogel, or any combination thereof.

Implementation 25.

The method according to any one of claims 22-24, wherein the body comprises polydimethylsiloxane (PDMS).

Implementation 26.

A metamaterial scaffold, comprising: (i) a structure defining a lumen; (ii) at least a portion of an outer or non-lumen surface of the tubular structure is coated with a plurality of biological cells, and wherein the structure is composed of a metamaterial.

Implementation 27.

The metamaterial scaffold according to implementation 26, wherein the structure is of a plain geometric shape.

Implementation 28.

The metamaterial scaffold according to implementation 26, wherein the structure has a shape of a native structure of a tissue.

Implementation 29.

The metamaterial scaffold according to any one of implementations 26-28, wherein the structure is a tubular structure defining first and second ends, and the lumen.

Implementation 30.

The metamaterial scaffold according to any one of implementations 26-29, wherein the structure is composed of an auxetic material.

Implementation 31.

The metamaterial scaffold according to any one of implementations 26-31, wherein the metamaterial comprises an auxetic structure.

Implementation 32.

The metamaterial scaffold of implementation 31, wherein the auxetic structure comprises a plurality of unit cells, each unit cell comprising a set of six points interconnected with six straight or curved members, including: a first member interconnecting points A and B; a second member interconnecting points B and C; a third member interconnecting points C and D; a fourth member interconnecting points D and E; a fifth member interconnecting points E and F; and a sixth member interconnecting points F and A.

Implementation 33.

The metamaterial scaffold of implementation 32, wherein the unit cells are connected in rows with the point D of one cell being connected to point A of an adjoining cell until completing a band around the tubular structure.

Implementation 34.

The metamaterial scaffold according to implementation 32 or 33, wherein the unit cells are connected in columns along the length of the structure with the line AB of one cell being connected to line EF of an adjoining cell until spanning the length of the structure.

Implementation 35.

The auxetic scaffold of implementation 31, wherein the unit cells are inverted hexagon unit cells.

Implementation 36.

The metamaterial scaffold according to any one of implementations 26-35, wherein the plurality of biological cells comprises a cell selected from the exemplary group consisting of cardiac muscle, bone, skeletal muscle, smooth muscle, pulmonary, esophageal and stomachal, intestinal cells, vascular cells, keratinizing epithelial cells, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell); Wet stratified barrier epithelial cells, such as Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts); Exocrine secretory epithelial cells, such as Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion), Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), pancreatic endocrine cells, Paneth cell of small intestine (lysozyme secretion), intestinal epithelial cells, Types I and II pneumocytes of lung (surfactant secretion), Clara cell of lung; hormone secreting cells, such as endocrine cells of the islet of Langerhands of the pancreas, Anterior pituitary cells, Somatotropes, Lactotropes, Thyrotropes, Gonadotropes, Corticotropes, Intermediate pituitary cell, secreting melanocyte-stimulating hormone; and Magnocellular neurosecretory cells secreting oxytocin or vasopressin; Gut and respiratory tract cells secreting serotonin, endorphin, somatostatin, gastrin, secretin, cholecystokinin, insulin, glucagon, bombesin; Thyroid gland cells such as thyroid epithelial cell, parafollicular cell, Parathyroid gland cells, Parathyroid chief cell, Oxyphil cell, Adrenal gland cells, chromaffin cells secreting steroid hormones (mineralcorticoids and gluco corticoids), Leydig cell of testes secreting testosterone, Theca internal cell of ovarian follicle secreting estrogen, Corpus luteum cell of ruptured ovarian follicle secreting progesterone, Granulosa lutein cells, Theca lutein cells, Juxtaglomerular cell (renin secretion), Macula densa cell of kidney, Peripolar cell of kidney, Mesangial cell of kidney; Metabolism and storage cells such as Hepatocyte (liver cell), White fat cell, Brown fat cell, Liver lipocyte; Barrier function cells (Lung, Gut, Exocrine Glands and Urogenital Tract) or Kidney cells such as Kidney glomerulus parietal cell, Kidney glomerulus podocyte, Kidney proximal tubule brush border cell, Loop of Henle thin segment cell, Kidney distal tubule cell, and/or Kidney collecting duct cell; Type I pneumocyte (lining air space of lung), Pancreatic duct cell (centroacinar cell), Nonstriated duct cell (of sweat gland, salivary gland, mammary gland, etc.), principal cell, Intercalated cell, Duct cell (of seminal vesicle, prostate gland, etc.), Intestinal brush border cell (with microvilli), Exocrine gland striated duct cell, Gall bladder epithelial cell, Ductulus efferens nonciliated cell, Epididymal principal cell, Epididymal basal cell; Epithelial cells lining closed internal body cavities such as Blood vessel and lymphatic vascular endothelial fenestrated cell, Blood vessel and lymphatic vascular endothelial continuous cell, Blood vessel and lymphatic vascular endothelial splenic cell, Synovial cell (lining joint cavities, hyaluronic acid secretion), Serosal cell (lining peritoneal, pleural, and pericardial cavities), Squamous cell (lining perilymphatic space of ear), Squamous cell (lining endolymphatic space of ear), Columnar cell of endolymphatic sac with microvilli (lining endolymphatic space of ear), Columnar cell of endolymphatic sac without microvilli (lining endolymphatic space of ear), Dark cell (lining endolymphatic space of ear), Vestibular membrane cell (lining endolymphatic space of ear), Stria vascularis basal cell (lining endolymphatic space of ear), Stria vascularis marginal cell (lining endolymphatic space of ear), Cell of Claudius (lining endolymphatic space of ear), Cell of Boettcher (lining endolymphatic space of ear), Choroid plexus cell (cerebrospinal fluid secretion), Pia-arachnoid squamous cell, Pigmented ciliary epithelium cell of eye, Nonpigmented ciliary epithelium cell of eye, Corneal endothelial cell; Ciliated cells with propulsive function such as Respiratory tract ciliated cell, Oviduct ciliated cell (in female), Uterine endometrial ciliated cell (in female), Rete testis ciliated cell (in male), Ductulus efferens ciliated cell (in male), and/or Ciliated ependymal cell of central nervous system (lining brain cavities); cells that secrete specialized ECMs, such as Ameloblast epithelial cell (tooth enamel secretion), Planum semilunatum epithelial cell of vestibular apparatus of ear (proteoglycan secretion), Organ of Corti interdental epithelial cell (secreting tectorial membrane covering hair cells), Loose connective tissue fibroblasts, Corneal fibroblasts (corneal keratocytes), Tendon fibroblasts, Bone marrow reticular tissue fibroblasts, Other nonepithelial fibroblasts, Pericyte, Nucleus pulposus cell of intervertebral disc, Cementoblast/cementocyte (tooth root bonelike cementum secretion), Odontoblast/odontocyte (tooth dentin secretion), Hyaline cartilage chondrocyte, Fibrocartilage chondrocyte, Elastic cartilage chondrocyte, Osteoblast/osteocyte, Osteoprogenitor cell (stem cell of osteoblasts), Hyalocyte of vitreous body of eye, Stellate cell of perilymphatic space of ear, Hepatic stellate cell (Ito cell), Pancreatic stellate cells; contractile cells, such as Skeletal muscle cells, Red skeletal muscle cell (slow), White skeletal muscle cell (fast), Intermediate skeletal muscle cell, nuclear bag cell of muscle spindle, nuclear chain cell of muscle spindle, Satellite cell (stem cell), Heart muscle cells, Ordinary heart muscle cell, Nodal heart muscle cell, Purkinje fiber cell, Smooth muscle cell (various types), Myoepithelial cell of iris, Myoepithelial cell of exocrine glands; Blood and immune system cells, such as Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types); Nervous system cells, Sensory transducer cells such as Auditory inner hair cell of organ of Corti, Auditory outer hair cell of organ of Corti, Basal cell of olfactory epithelium (stem cell for olfactory neurons), Cold-sensitive primary sensory neurons, Heat-sensitive primary sensory neurons, Merkel cell of epidermis (touch sensor), Olfactory receptor neuron, Pain-sensitive primary sensory neurons (various types); Photoreceptor cells of retina in eye including Photoreceptor rod cells, Photoreceptor blue-sensitive cone cell of eye, Photoreceptor green-sensitive cone cell of eye, Photoreceptor red-sensitive cone cell of eye, Proprioceptive primary sensory neurons (various types); Touch-sensitive primary sensory neurons (various types); Type I carotid body cell (blood pH sensor); Type II carotid body cell (blood pH sensor); Type I hair cell of vestibular apparatus of ear (acceleration and gravity); Type II hair cell of vestibular apparatus of ear (acceleration and gravity); and/or Type I taste bud cell; Autonomic neuron cells such as Cholinergic neural cell (various types), Adrenergic neural cell (various types), Peptidergic neural cell (various types); sense organ and peripheral neuron supporting cells, such as Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Type I taste bud supporting cell, Olfactory epithelium supporting cell, Schwann cell, Satellite cell (encapsulating peripheral nerve cell bodies), Enteric glial cells; central nervous system neurons and glial cells such as Astrocyte (various types), Neuron cells (large variety of types, still poorly classified), Oligodendrocyte, and Spindle neuron; Lens cells such as Anterior lens epithelial cell and Crystallin-containing lens fiber cells; pigment cells such as melanocytes and retinal pigmented epithelial cells; and germ cells, such as Oogonium/Oocyte, Spermatid, Spermatocyte, Spermatogonium cell (stem cell for spermatocyte), and Spermatozoon; nurse cells; Ovarian follicle cells; Setoli cell (in testis); Thymus epithelial cells; and interstitial cells such as interstitial kidney cells.

Implementation 37.

The metamaterial scaffold according to any one of implementations 26-36, wherein the plurality of biological cells comprises cardiomyocytes.

Implementation 38.

The metamaterial scaffold according to any one of implementations 26-37, wherein the lumen has a diameter between about 0.005 mm and about 50 mm.

Implementation 39.

A microfluidic device comprising a metamaterial scaffold according to any one of implementations 26-38.

Implementation 40.

The microfluidic device of implementation 36, further comprising a valve of any one of implementations 1-20 in fluid communication with the metamaterial scaffold.

Implementation 41.

The microfluidic device of implementation 39, comprising a first port and a second port, the first port being in fluid communication with the metamaterial scaffold via a first channel portion, the second port being in fluid communication with the metamaterial scaffold via a second channel portion; a first valve disposed in the first channel portion; and a second valve disposed in the second channel portion, wherein the first valve and the second valve are configured to cause unidirectional flow through the metamaterial scaffold.

Implementation 42.

The microfluidic device of implementation 39, comprising a main channel in fluid communication with the metamaterial scaffold, the microfluidic device further comprising a first port and a second port, the first port being in fluid communication with the main channel via a first channel portion, the second port being in fluid communication with the main channel via a second channel portion; a first valve disposed in the first channel portion; and a second valve disposed in the second channel portion.

It is contemplated that any element or any portion thereof from any of implementations 1-42 above can be combined with any other element or elements or portion(s) thereof from any of implementations 1-42 to form an implementation of the present disclosure.

Some of the embodiments will be more readily understood by reference to the following examples, which are included merely for purposes of illustration of certain aspects and embodiments of the present invention, and should not be construed as limiting. As such, it will be readily apparent that any of the disclosed specific constructs and experimental plan can be substituted within the scope of the present disclosure.

EXAMPLES

Scaffold-Based Ventricular Microfluidic Model

Figure 15B:
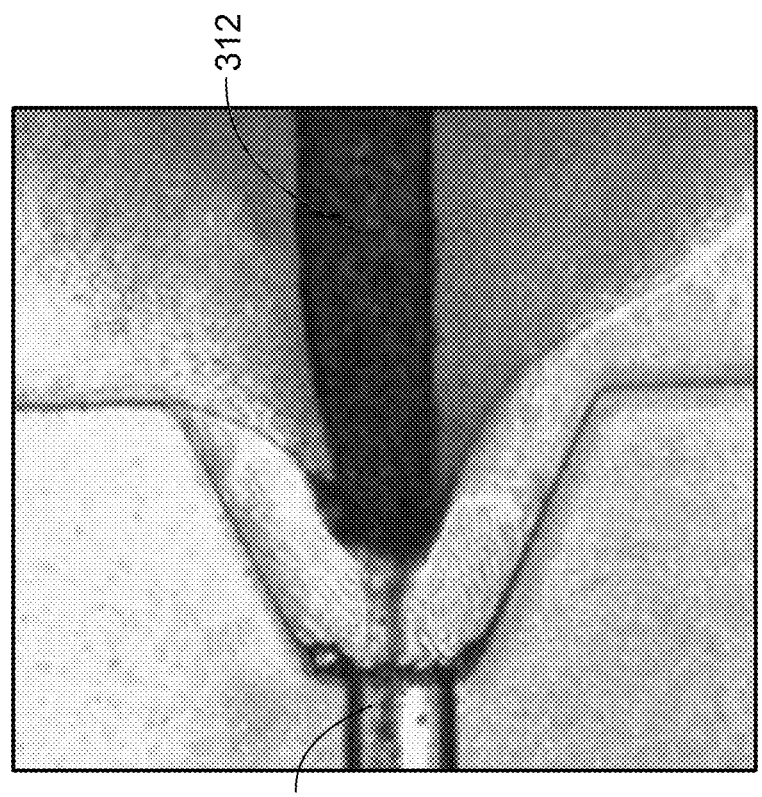
FIG. 15B shows the cardiac device of FIG. 15A seven days after seeding according to some implementations of the present disclosure.
Figure 15A:
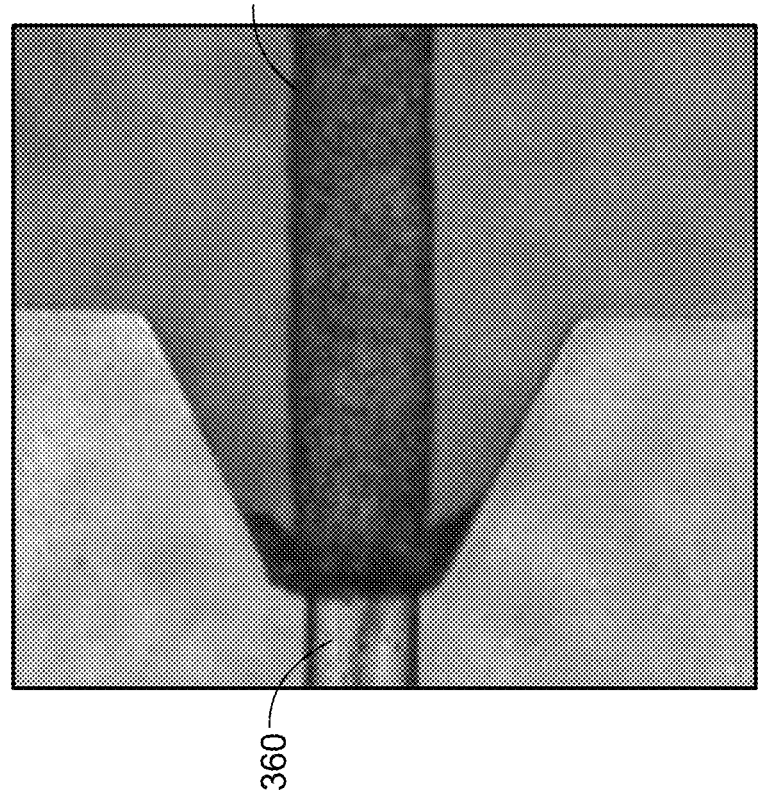
FIG. 15A shows a portion of a micro-cardiac device with cardiac tissue one day after seeding according to some implementations of the present disclosure.

An in vitro ventricular model needs to be structurally stable and to produce measurable contractile output. Structural stability of the in vivo myocardium is established by the passive tensile stress produced by its elastic extracellular matrix and by the pressure within the cardiac chambers. An in vitro scaffold should thus be able to incorporate such tensile forces. The need for such a scaffold is shown with reference to FIG. 15A and FIG. 15B which shows a channel portion 360 and cardiac tissue 312, such as a first 360A or second 360B channel portion with a cardiac tissue 312 configured as shown in FIG. 7. The heart tube model is shown one day after seeding, 15A, and 7 days, 15B, after seeding, demonstrating the effect of matrix compaction in the absence of a mechanical support. The construct began collapsing a couple of days' post seeding due to the cell-mediated compaction of the extracellular matrix, blocking the channel, halting fluid displacement upon contraction and obstructing media flow and nutrient exchange. Eventually the tissue turned necrotic and did not beat.

Moreover, the native myocardium is organized in aligned, anisotropic myocardial fibers and output maximization relies on the directional contraction of cardiomyocytes. Such anisotropy can be achieved in vitro by exposing the cardiac tissue to anisotropic ECM architecture or anisotropic mechanical stiffness, causing cardiomyocyte alignment and elongation. A mechanically anisotropic scaffold could therefore improve contractile output.

Additionally, the in vivo myocardium utilizes multiple layers of thick myocardial musculature to produce the observed powerful contractions. In vitro models cannot utilize muscular thickness to generate output, as tissues beyond 300 µm thickness require perfusion through vascularization that has yet to be achieved in in vitro cardiac tissues. Engineering scaffolds to enhance output beyond cellular anisotropy can provide sufficient, measurable cardiac output in vitro in the absence of vasculature.

To address these issues, TPDLW was used to fabricate a scaffold with (1) specified geometry to produce concave cardiac tissue, (2) specified mechanical stiffness to preserve tissue structure, (3) mechanical anisotropy to induce tissue alignment and improvement contractility and (4) auxetic properties to promote chamber volume reduction upon cellular contraction. In addition, a protocol to seed cardiac tissue on the resulting scaffold and a microfluidic system to monitor and measure the contractile performance of the seeded tissue can be implemented.

Experimental

Existing data on the µTUG (Hinson, J. T. et al. *Science* (80-.), 349, 982-986 (2015)) cardiac tissue system can be used to calculate the static force exerted by cardiac tissue and estimate an approximation of the required passive stiffness of the scaffold. Reported auxetic cell units, such as the inverted hexagon (FIGS. 12A and 12B), can be utilized to form a cylindrical auxetic scaffold. FEM simulations (COMSOL Multi-physics) can be used to calculate each scaffold design's mechanical properties and the design can then be iterated to achieve the estimated mechanical requirements. The scaffold can be printed with TPDLW to accurately replicate its simulated geometrical features. TPDLW requires submerging the printed scaffold in solvents whose surface tension might exceed the yield stress of the scaffold and therefore crush the scaffold upon drying. In such an event, Critical Point Drying (CPD) (DCP-1, Denton) can be used to dry the scaffold.

To accelerate the scaffold development cycle, results from mechanical characterization can be used to calibrate the simulation results, allowing design iteration to be accomplished largely by simulations. The photoresist IP-S(Nanoscribe GmbH) can be used, as it provides sufficient resolution to print the expected features of the scaffold, but allows a higher print speed to accelerate the printing process. Rectangular blocks of IP-S of 300×300×10 µm dimensions (L×W×H) can be printed and subjected to a compression test with nanoindentation (Hysitron Triboindenter) to measure the mechanical properties of IP-S. A tensile test on springs printed on electrostatic comb drive micro-electromechanical system (MEMS) devices can be used as previously reported (J. R. K. Stark et. al., *Adv. Mater. Technol.* 3, 1-6 (2018)) to apply strain on microscopic spring of IP-S to measure the mechanical properties of IP-S under tension. To verify the compression and tensile measurements, nanoindentation can be used to extract the stress-strain curve of an IP-S beam using a cantilever deflection test and can be compared to the curve generated by the equivalent in silico model. Finally, nanoindentation can be used to measure the force-displacement curve of the scaffold, its Poisson ratio and its resilience to fatigue, which will verify the corresponding simulation results.

PDMS molding can be used to fabricate the microfluidic system. The printed scaffold can be placed at the entrance of the microfluidic channel, and can be seeded using an adaption of the existing seeding protocols for the µTUG system. Particle Image Velocimetry can be used to estimate the volume changes of the cell-laden scaffold and the pressure fluctuations due to the tissue contractions.

Results

Figure 16A:
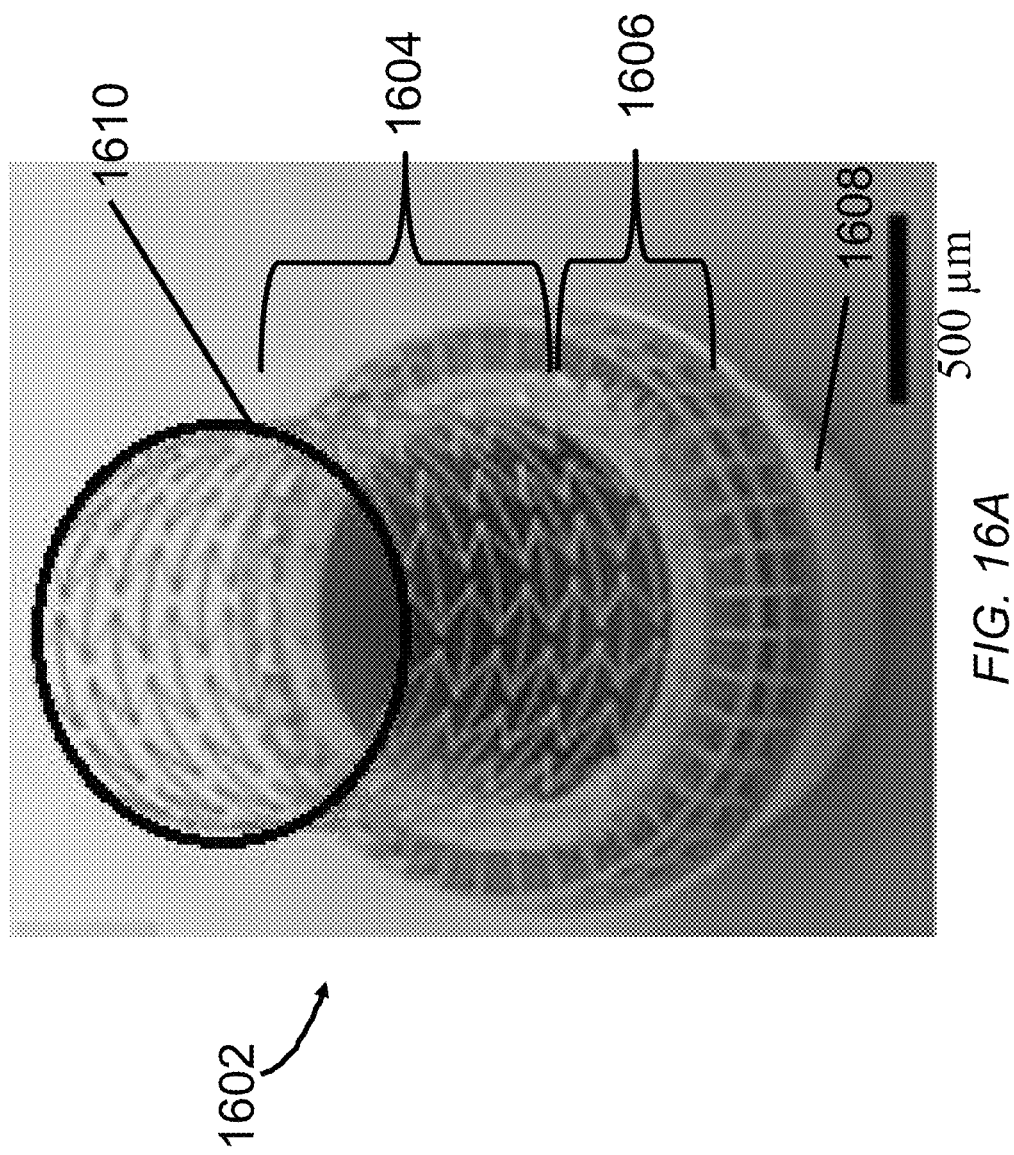
FIG. 16A shows a hollow cylindrical construct based on an inverted hexagon cell unit according to some implementations of the present disclosure.
Figure 16B:
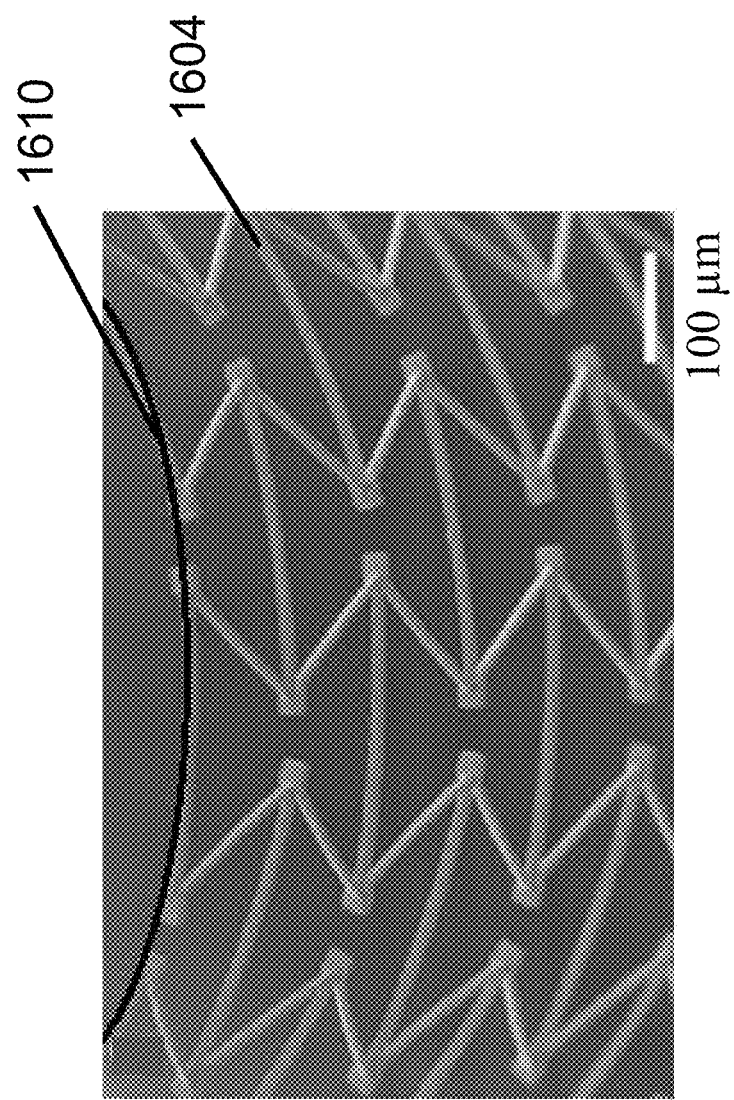
FIG. 16B shows a detailed view of the cylindrical construct of FIG. 16A according to some implementations of the present disclosure.

Scaffolds were printed with TPDLW using photoresist IP-S(Nanoscribe). A hollow cylindrical construct 1602 based on the inverted hexagon cell unit was designed and printed as shown in FIG. 16A. Region 1604 shows the auxetic scaffold, and region 1606 shows a rectangular lattice that forms part of the scaffold and is designed to serve as a fixed attachment structure for the tissue and to facilitate insertion of the construct onto a microfluidic channel by way of cylindrical stem 1608. The scale bar for FIG. 16A is 500 µm. FIG. 16B shows a detailed section of the auxetic scaffold, where the scale bar shows 100 µm. In both FIGS. 16A and 16B, the line 1610 is added to help guide the eyes, and does not necessarily form a part of the construct. FEM simulations were used to validate the auxetic behavior of the scaffold.

Figure 17A:
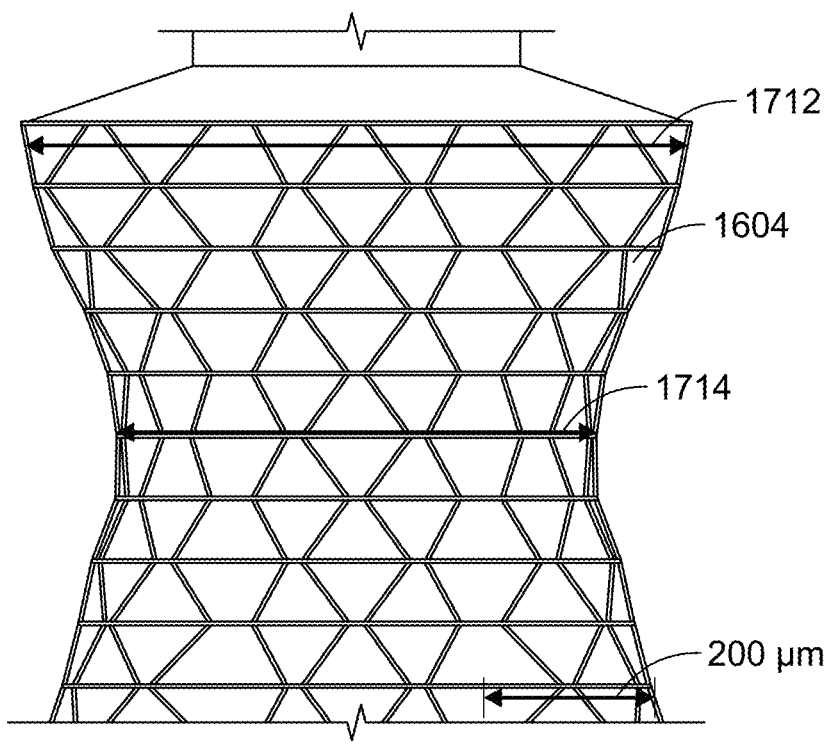
FIG. 17A shows an auxetic mesh under compression during a nanoindentation test according to some implementations of the present disclosure.
Figure 17B:
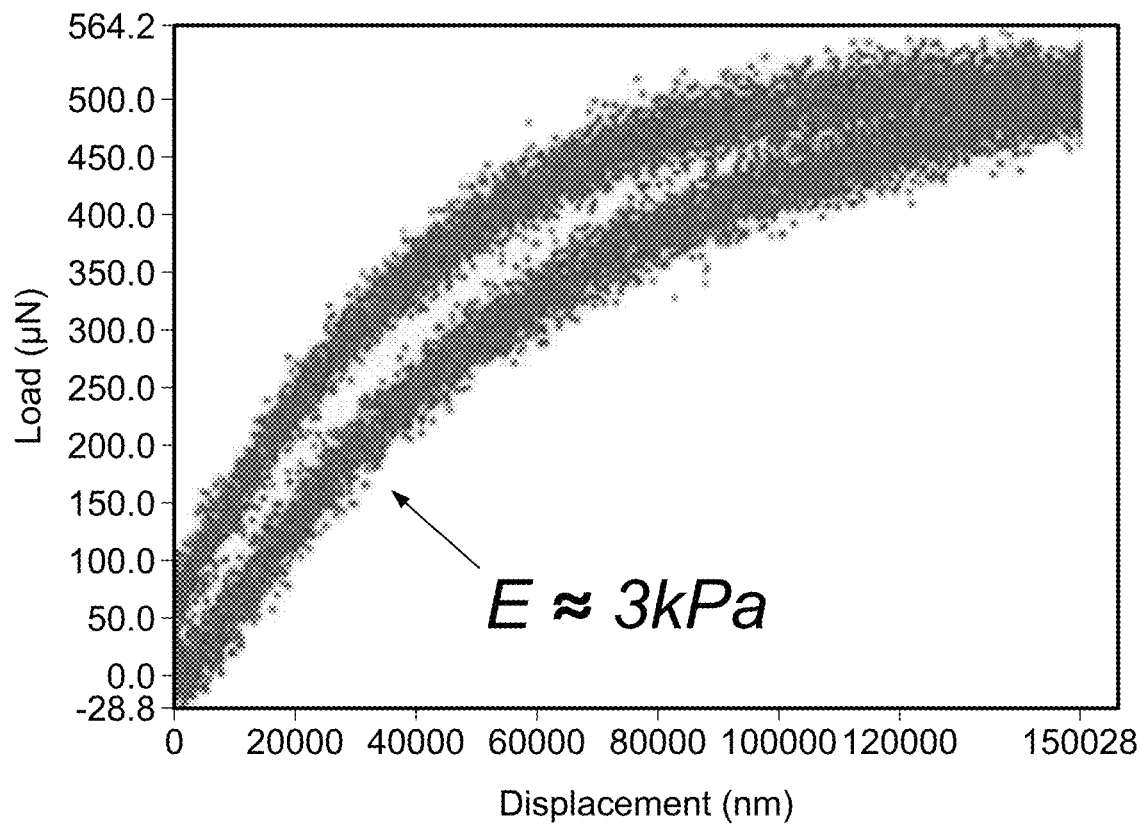
FIG. 17B shows a plot of the force-displacement data for a nanoindentation test according to some implementations of the present disclosure.

The mechanical and auxetic properties of the scaffold were also probed using nanoindentation. FIG. 17A shows the auxetic mesh under compression during a nanoindentation test, where the scale bar is 200 µm. The minimum diameter 1712 and initial diameter 1714 are indicated by double headed arrows. FIG. 17B shows the force-displacement curve for a nanoindentation test. The scaffold demonstrates non-linear stress-strain curves with an initial stiffer linear regime followed by a softer semi-linear regime. The initial linear modulus is estimated at 3 kPa. Ideally, the static compaction force should be absorbed by the stiff linear regime, and the dynamic contractile force will be exerted on the soft non-linear regime, minimizing simultaneously the volume loss due to compaction and the resistance to the contractile force.

Figure 18G:
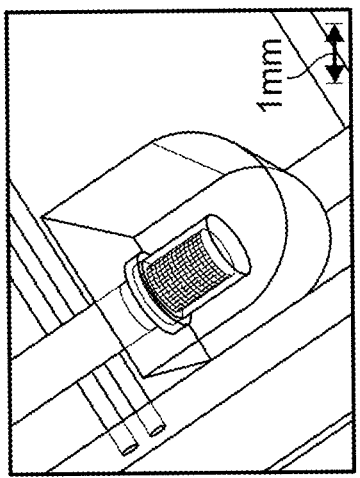
FIG. 18G shows the removal of the needle according to some implementations of the present disclosure.
Figure 18I:
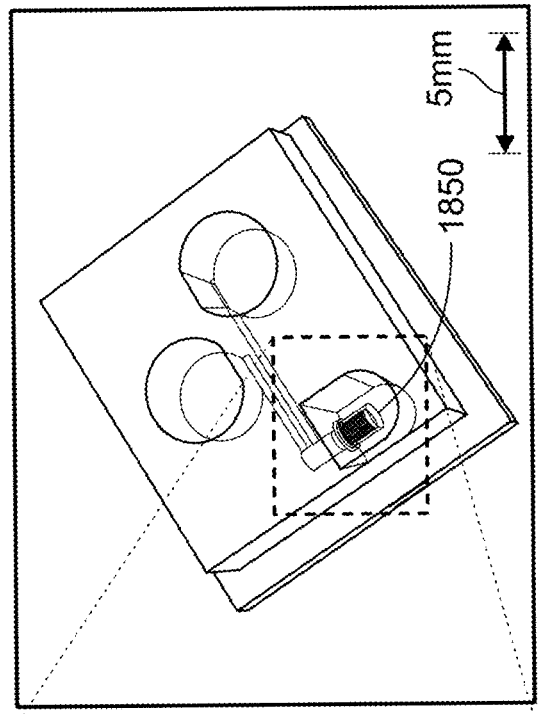
FIG. 18I shows the completed device according to some implementations of the present disclosure.

PDMS microfluidic devices were then designed and implemented as shown in FIGS. 18A-18I. FIG. 18A shows an initial microfluidic device prior to addition of the auxetic construct. A protocol to add the printed construct to the microfluidic device and seed this with cells is shown by the detailed views of FIG. 18B-18H, which creates a hollow cylindrical cap of cardiac tissue supported by the auxetic mesh and attached to the end of the main channel 1802 of the microfluidic device. The microfluidic device after addition of the auxetic construct is shown by FIG. 18I, illustrating tissue 1850 in well 1810 that is microfluidically connected to the large major channel 1802 that communicates through small minor channels 1804 and 1805 housing the valves (not shown here) with wells 320 and 310 whose hydrostatic pressure can be controlled.

Figure 18F:
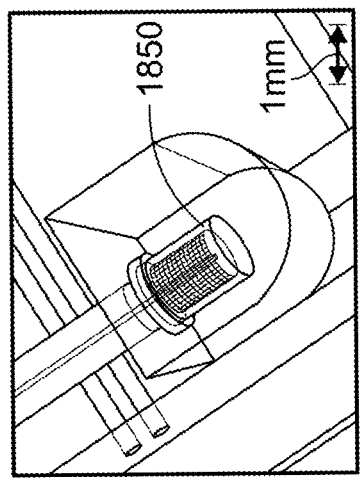
FIG. 18F shows the formation of a cell-laden layer around the needle according to some implementations of the present disclosure.
Figure 18H:
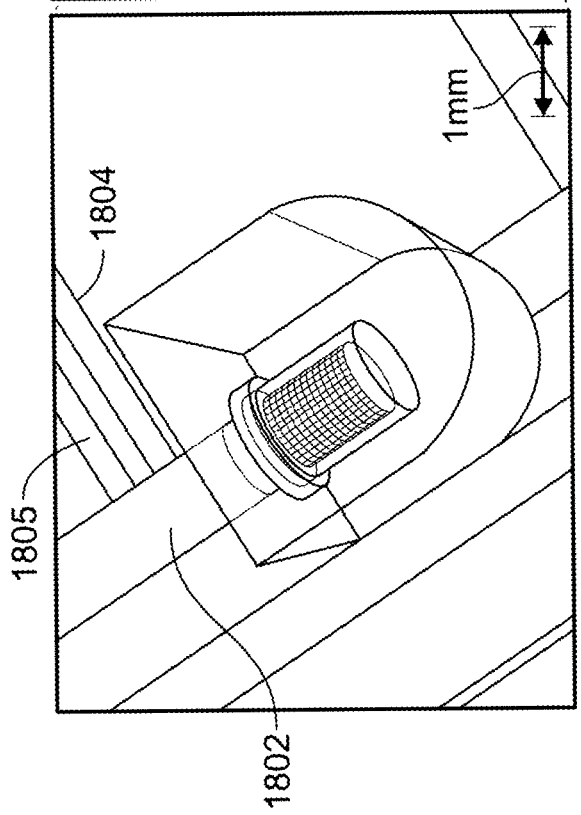
FIG. 18H shows sealing of the redundant channels in the microfluidic device according to some implementations of the present disclosure.

Therefore, in additional detail: FIGS. 18A and 18B shows the initial microfluidic PDMS device consists of a network of microfluidic channels that connect 3 wells. The first circular well 320 and second well 330 are configured to house liquid columns to regulate the pressure experienced in the third well 1810 designed as a chamber for housing the tissue 1850. In a first step, FIG. 18C, of the seeding protocol, the scaffold 1602 is inserted in the tissue well 1810 and fixed at the end of the channel 1802. FIG. 18D shows a second step where a needle 1808 is inserted to occupy the cavity of the scaffold 1602. The tissue well 1810 is in a third step filled with a liquid solution 1820 containing cells and extracellular matrix as shown by FIG. 18E. FIG. 18F shows a fourth step where the matrix gels and is compacted by the cells, forming a cell-laden layer 1850 around the needle. The needle is removed in a fifth step, leaving behind a cavity, FIG. 18G. In the final, sixth, step shown by FIG. 18H the redundant channels are sealed, producing a closed microfluidic system.

A similar seeding protocol as described here can be used to make any construct described in this disclosure. For example, the microfluidic devices as shown and described with reference to FIG. 8A-8F or FIG. 9A-9B, where the tissue is supported with an extracellular matrix such as the scaffold 1602, can be made. For example, the scaffold 1602 could further include a second rectangular mesh similar to 1606 and positioned at indicating line 1610, for attachment to a second cylindrical stem similar to cylindrical stem 1608.

Validation of Ventricular Properties and Investigation of Load-Function Relation.

Current in vitro models fail to replicate the pressure and volume conditions of the ventricle, and its derivative measures of contractility, compliance and ejection fraction. The classification of heart failure (HF) into HF with preserved ejection fraction and into HF with reduced ejection fraction is a prime example of the significance of such measures. A system that uses the valves and metamaterial supported tissues as described herein can be assembled to provide a system to recapitulate the Left Ventricular Pressure Volume Loop (PV loop). This system can recapitulate the myocardial response to established pharmacological, electrical and mechanical modulators though pressure-volume measurements. The system can also be used to probe the effect of increased preload and afterload on tissue performance and remodeling.

Experimental

The sub-pascal valves, such as valves 100 (FIGS. 1A-1C) and 200 (FIGS. 6A and 6B) can be added to the minor channels 1805 and 1804 of a microfluidic system, such as the system shown by (FIG. 18I). The ability of the tissue to regulate the valves, the emergence of unidirectional flow from one well to the other and the presence of a PV loop without the isovolumetric phases can be confirmed. Glass columns can be added to the wells to control the pressure in the wells through liquid addition and removal, thereby differentiating the preload and afterload pressures. The afterload can be increased to replicate the PV loop with all 4 phases included.

The acute response of the cardiac tissue with potent modulators of contractile performance such as isoproterenol (adrenergic agonist: Novak, A. et al. *J. Cell. Mol. Med.* 16, 468-482 (2012)) and carteolol (non-selective adrenergic antagonist), carbachol (cholinergic agonist), digoxin ($Na^+$/$K^+$ ATPase inhibitor), Verapamil/Nifedipine (L-type $Ca^{2+}$ channel inhibitor: Nunes, S. S. et al. *Nat. Methods* 10, (2013)), disopyramide/flecainide ($Na^+$ channel inhibitor)[13], caffeine (ryanodine receptor agonist) and doxorubicin (cardiotoxic chemotherapeutic agent: Pai, V. B. et. al., *Drug Sal.* 22, 263-302 (2000)) can be demonstrated. The response to such modulators through their effect on the PV loop outputs can be quantified. Furthermore, the tissues can be electrically paced with increasing frequency to demonstrate the force frequency response in the PV loop metrics. The preload pressure will also be acutely increased to demonstrate the Frank Starling mechanism.

To investigate the effects of load changes on cardiac performance, the tissues can first be allowed to mature under constant 1 Hz stimulation. µTUG data from previous experiments show that 10 days are required for the tissue output to stabilize. Therefore, starting day 11, a comparison cardiac performance under a permanently increased preload and/or afterload can be made. The performance of the tissue can be monitored daily until a statistically significant difference in ejection fraction is observed, or up to a set amount of days, such as up to 14 days. RNA sequencing can be used to quantify transcriptome. Gene expression changes can be compared to control tissues and to data from in vivo studies. In parallel, cellular shape and size through membrane staining with wheat germ agglutinin and sarcomeric structure through α-actinin2 staining can be used to evaluate the effect of load on the cells. For statistical analysis of the PV loops, gene expression, cellular and sarcomeric metrics data can be evaluated using analysis of variance (ANOVA) with significance at 95% confidence intervals, p-value <0.05.

What is claimed is:

1. A valve comprising:
a body including an inner bore extending between a first port and a second port, a seat, and one or more restrainers; and
a disk including a cylindrical portion and a spherical portion, the disk being moveable between the seat and the one or more restrainers and being configured such that (i) a first pressure that is less than 1 pascal and applied in a first direction causes the disk to move from a first position towards a second position to permit fluid communication between the first port and the second port and (ii) a second pressure that is less than 1 pascal and applied in a second opposing direction causes the disk to move from the second position towards the first position to inhibit fluid communication between the first port and the second port.

2. The valve of claim 1, wherein the first pressure and the second pressure are less than 0.5 pascals.

3. The valve of claim 1, wherein the first pressure is between about 0.1 pascals and about 0.5 pascals.

4. The valve of claim 1, wherein the second pressure is between about 0.05 pascals and about 0.2 pascals.

5. The valve of claim 1, wherein the disk is moveable such that the first pressure causes the disk to move from the first position to the second position in less than 500 milliseconds.

6. The valve of claim 1, wherein the body is cylindrical and has a first diameter is that is 400 microns or less and a longitudinal length that is 1110 microns or less, and the inner bore is cylindrical and has a second diameter that is 300 microns or less.

7. The valve of claim 1, wherein a distance between the disk and the one or more restrainers is between about 10 microns and about 30 microns responsive to the disk being in the second position.

8. The valve of claim 1, wherein the body is rigid.

9. The valve of claim 1, wherein the body is monolithic.

10. The valve of claim 1, wherein a portion of the spherical portion of the disk contacts the seat responsive to the disk being in the first position to aid inhibiting fluid communication between the first port and the second port.

11. The valve of claim 1, wherein the spherical portion of the disk has a degree of curvature that is between about 30 degrees and about 60 degrees.

12. The valve of claim 1, wherein a distance between the first port and the seat is between about 5% and about 15% of a longitudinal length of the body.

13. A microfluidic system comprising:
a valve including:
a body including an inner bore extending between a first port and a second port, a seat having an opening and being disposed within the inner bore, and a plurality of restrainers positioned between the seat and the second port; and
a disk configured to move relative to the seat and the plurality of restrainers such that application of a first predetermined pressure that is between about 0.05 pascals and 1 pascal causes the disk to move from a first position towards a second position to permit fluid communication between the first port and the second port.

14. The valve of claim 13, wherein the disk inhibits fluid communication between the first port and the second port responsive to being in the first position.

15. The valve of claim 14, wherein a spherical portion of the disk is partially disposed within the opening of the seat to aid in inhibiting fluid communication between the first port and the second port responsive to the disk being in the first position.

16. The valve of claim 14, wherein the disk is moveable such that application of a second predetermined pressure causes the disk to move from the second position towards the first position to inhibit fluid communication between the first port and the second port.

17. The valve of claim 16, wherein the first predetermined pressure is different than the second predetermined pressure.

18. The valve of claim 13, wherein the disk includes a spherical portion and a cylindrical portion having a first diameter that is less than a second diameter of the inner bore.

19. The valve of claim 18, wherein a third diameter of the opening of the seat is equal to or smaller than twice the first diameter minus the second diameter.

20. The valve of claim 13, wherein the body is monolithic.

\* \* \* \* \*